US011214768B2

(12) United States Patent
Lewis et al.

(10) Patent No.: US 11,214,768 B2
(45) Date of Patent: Jan. 4, 2022

(54) METHODS OF GENERATING FUNCTIONAL HUMAN TISSUE

(71) Applicant: PRESIDENT AND FELLOWS OF HARVARD COLLEGE, Cambridge, MA (US)

(72) Inventors: Jennifer A. Lewis, Cambridge, MA (US); Mark A. Skylar-Scott, Brookline, MA (US); David B. Kolesky, Cambridge, MA (US); Kimberly A. Homan, Somerville, MA (US); Alex H. M. Ng, Cambridge, MA (US); George M. Church, Brookline, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 318 days.

(21) Appl. No.: 15/554,963

(22) PCT Filed: Mar. 3, 2016

(86) PCT No.: PCT/US2016/020601
§ 371 (c)(1),
(2) Date: Aug. 31, 2017

(87) PCT Pub. No.: WO2016/141137
PCT Pub. Date: Sep. 9, 2016

(65) Prior Publication Data
US 2018/0030409 A1     Feb. 1, 2018

Related U.S. Application Data

(60) Provisional application No. 62/294,118, filed on Feb. 11, 2016, provisional application No. 62/250,338, (Continued)

(51) Int. Cl.
| C12N 5/00 | (2006.01) |
| A61L 27/38 | (2006.01) |
| A61K 35/545 | (2015.01) |
| C12N 5/071 | (2010.01) |
| C12N 5/0793 | (2010.01) |
| C12N 5/077 | (2010.01) |
| C12N 5/079 | (2010.01) |
| B29C 64/106 | (2017.01) |
(Continued)

(52) U.S. Cl.
CPC .......... *C12N 5/0062* (2013.01); *A61K 35/545* (2013.01); *A61L 27/38* (2013.01); *B29C 64/106* (2017.08); *C12N 5/069* (2013.01); *C12N 5/0618* (2013.01); *C12N 5/0619* (2013.01); *C12N 5/0656* (2013.01); *C12N 5/0697* (2013.01); *B29K 2089/00* (2013.01); *B29K 2105/0061* (2013.01); *B33Y 10/00* (2014.12); *B33Y 70/00* (2014.12); *B33Y 80/00* (2014.12); *C12N 2501/165* (2013.01); *C12N 2501/40* (2013.01); *C12N 2501/60* (2013.01); *C12N 2501/727* (2013.01); *C12N 2502/28* (2013.01); *C12N 2502/45* (2013.01); *C12N 2506/45* (2013.01); *C12N 2533/30* (2013.01); *C12N 2533/54* (2013.01); *C12N 2535/00* (2013.01)

(58) Field of Classification Search
CPC .. C12N 5/0062; C12N 5/069; C12N 2502/45; C12N 2506/45; C12N 2502/28
USPC ........................................................ 435/11
See application file for complete search history.

(56) References Cited

U.S. PATENT DOCUMENTS 9,617,519 B2      4/2017   Sakaguchi et al.
2011/0270412 A1*  11/2011  Bellan ................. A61L 27/3808
                                                              623/23.72
(Continued)

FOREIGN PATENT DOCUMENTS

CN    101410507 A    4/2009
CN    101410507 A    4/2009
(Continued)

OTHER PUBLICATIONS

Mohammadi, M. H. et al., Skin diseases modeling using combined tissue engineering and microfluidic technologies. Advanced Healthcare Materials, 2016 (published online: Aug. 22, 2016), vol. 5, Issue 19, pp. 2459-2480. (Year: 2016).*

(Continued)

*Primary Examiner* — Valarie E Bertoglio
(74) *Attorney, Agent, or Firm* — Crowell & Moring LLP

(57) ABSTRACT

Methods of tissue engineering, and more particularly methods and compositions for generating various vascularized 3D tissues, such as 3D vascularized embryoid bodies and organoids are described. Certain embodiments relate to a method of generating functional human tissue, the method comprising embedding an embryoid body or organoid in a tissue construct comprising a first vascular network and a second vascular network, each vascular network comprising one or more interconnected vascular channels; exposing the embryoid body or organoid to one or more biological agents, a biological agent gradient, a pressure, and/or an oxygen tension gradient, thereby inducing angiogenesis of capillary vessels to and/or from the embryoid body or organoid; and vascularizing the embryoid body or organoid, the capillary vessels connecting the first vascular network to the second vascular network, thereby creating a single vascular network and a perfusable tissue structure.

37 Claims, 41 Drawing Sheets

Related U.S. Application Data filed on Nov. 3, 2015, provisional application No. 62/127,549, filed on Mar. 3, 2015.

(51) Int. Cl.
    *B33Y 10/00*    (2015.01)
    *B33Y 70/00*    (2020.01)
    *B33Y 80/00*    (2015.01)
    *B29K 105/00*   (2006.01)

(56) References Cited

U.S. PATENT DOCUMENTS

| | | | |
|---|---|---|---|
| 2012/0058174 | A1 | 3/2012 | West et al. |
| 2013/0004469 | A1* | 1/2013 | Glazier ................ C12M 21/08 424/93.7 |
| 2013/0030548 | A1* | 1/2013 | Ling ...................... A61L 27/60 623/23.72 |
| 2013/0280807 | A1 | 10/2013 | Takezawa et al. |
| 2015/0037445 | A1 | 2/2015 | Murphy et al. |

FOREIGN PATENT DOCUMENTS

| | | |
|---|---|---|
| CN | 101534747 A | 9/2009 |
| CN | 106163581 A | 11/2016 |
| EP | 2 762 558 A1 | 8/2014 |
| JP | 2009-531067 | 9/2009 |
| WO | WO 02/078439 A2 | 10/2002 |
| WO | WO 2007/112192 A2 | 10/2007 |
| WO | WO 2008/008229 A2 | 1/2008 |
| WO | WO 2012/036225 A1 | 3/2012 |
| WO | WO 2013/096741 A2 | 6/2013 |
| WO | WO 2014/090993 A1 | 6/2014 |
| WO | WO 2014/168719 A1 | 10/2014 |
| WO | WO 2016/141137 A1 | 9/2016 |

OTHER PUBLICATIONS

International Search Report and Written Opinion received in PCT Application No. PCT/US2016/020601, dated May 31, 2016.
Mondrinos et al., "Engineering De Novo Assembly of Fetal Pulmonary Organoids," *Tissue Engineering*, Part A, 20(21-22):2892-2907 (Jun. 25, 2014).
Takebe et al., "Generation of Functional Human Vascular Network," *Transplantation Proceedings*, 44(4):1130-1133 (May 1, 2012).
Takebe et al., "Engineering of Human Hepatic Tissue with Functional Vascular Networks," *Organogenesis*, 10(2):260-267 (Jan. 22, 2014).
Extended European Search Report (EESR) with the supplementary European search report and the European search opinion received for the corresponding European Application No. 16759465.4 dated Oct. 5, 2018.
Notification Concerning Transmittal of International Preliminary Report on Patentability dated Sep. 14, 2017, International Preliminary Report on Patentability and Written Opinion of the International Searching Authority received in PCT Application No. PCT/US2016/020601.
Reporting Letter received from Japanese associate dated Jan. 31, 2020 enclosing English translation of Official Action received in Japanese Application No. JP 2017-546660 dated Jan. 2, 2020 (Japanese version included).
Reporting Letter received from Japanese associate dated Jan. 21, 2020 and Official Action received in Japanese Application No. JP 2017-546660 dated Jan. 2, 2020 (in Japanese).
Hosoe, H., et al., "Investigation of VEGF and PDGF signals in vascular formation by 3D culture models using mouse ES cells," *Stem Cell Discovery*, 2(2):70-77 (2012).
Brownfield, D., et al., "Patterned Collagen Fibers Orient Branching Mammary Epithelium through Distinct Signaling Modules," *Current Biology*, 23:703-709 (2013).
Kolesky, D., et al., "3D Bioprinting of Vascularized, Heterogeneous Cell-Laden Tissue Constructs," *Advanced Materials*, 26:3124-3130 (2014).
Reporting Letter received from European associate dated Jan. 20, 2020 and Communication Pursuant to Article 94(3) received in European Application No. 16759465.4 dated Jan. 14, 2020.
Reporting letter dated Jul. 7, 2020 enclosing First Office Action received in Chinese Application No. 201680022237.7 dated Jun. 15, 2020 (in Chinese and including English translation of the First Office Action).
Examination Report received in the corresponding European Patent Application No. 16759465.4 dated Jan. 18, 2021, and a letter from the European associate dated Jan. 26, 2021 reporting the Examination Report.
Bertassoni, L.E., et al., "Hydrogel bioprinted microchannel networks for vascularization of tissue engineering contructs," *Lab Chip*, 14:2202-2211 (2014).
Lee, V.K., et al., "Construction of 3D Tissue with Perfused Vessels and Capillaries through 3D Bio-Printing," $40^{th}$ *Annual Northeast Bioengineering Conference*, 2 pgs. (2014).
Reporting Letter dated Jan. 27, 2021 enclosing the Notification of Second Office Action received in Chinese Patent Application No. 201680022237.7 dated Jan. 25, 2021 (in Chinese and including English translation of the Second Office Action).
Examination Report No. 2 received in the corresponding Australian Patent Application No. 2016226178 dated Mar. 31, 2021 and a letter from the Australian associate dated Apr. 14, 2021 reporting the Examination Report.
Reporting Letter dated Sep. 1, 2021 enclosing the Rejection Decision received in Chinese Application No. 201680022237.7 dated Aug. 18, 2021 (in Chinese and including English translation of the Rejection Decision).
First Examination Report received in the corresponding Australian Patent Application No. 2016226178 dated Aug. 25, 2020, and a copy of a letter from the Australian associate dated Sep. 2, 2020 reporting the First Examination Report.

\* cited by examiner

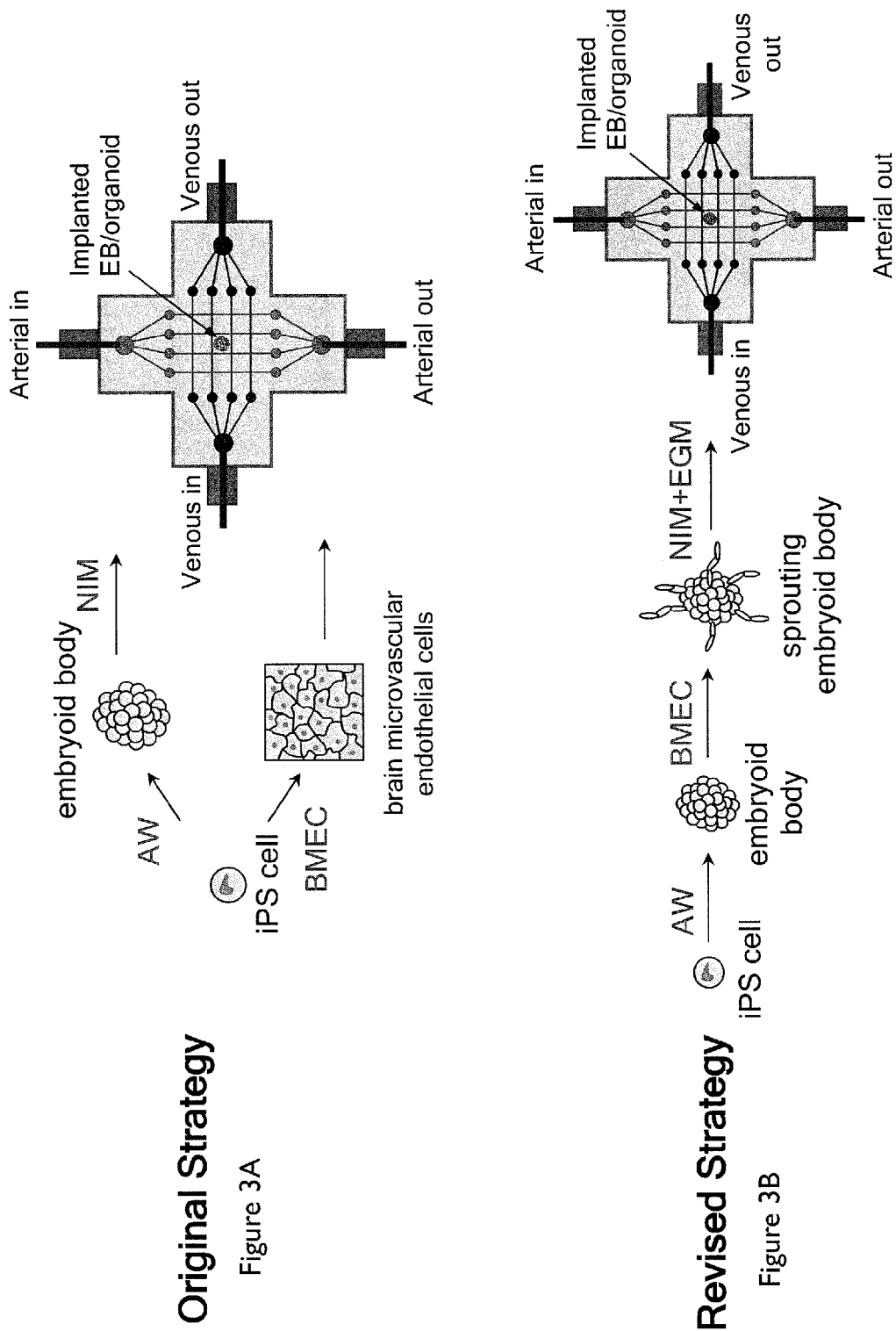

Generating Cerebral Organoids
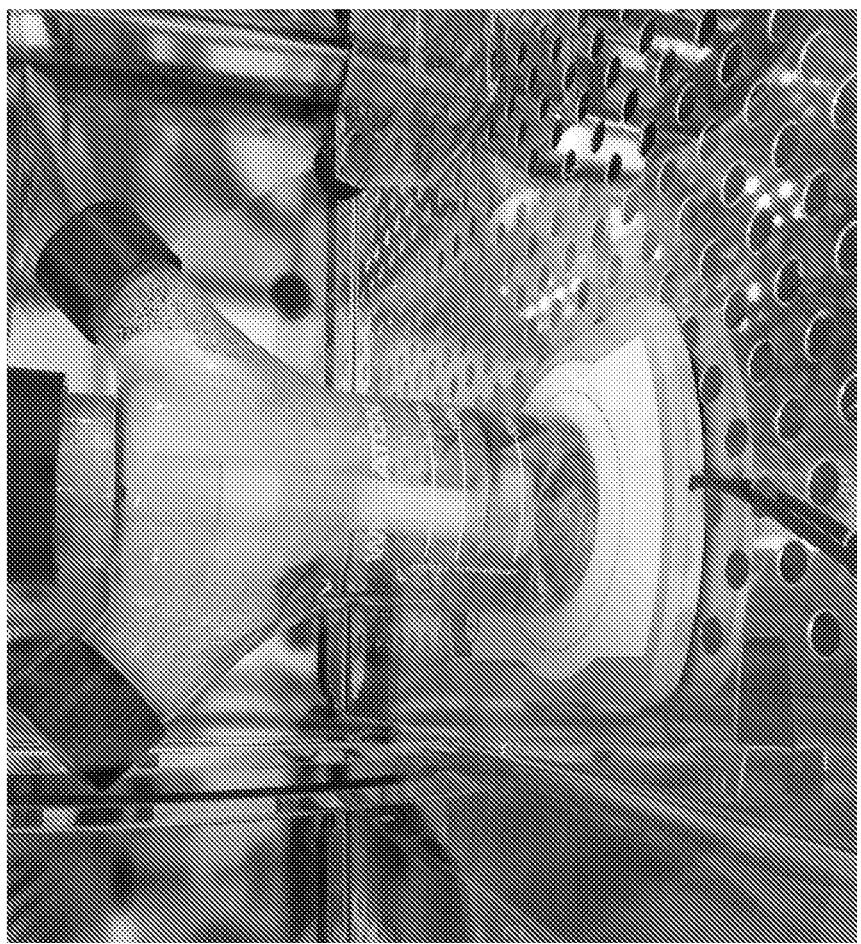
Fig. 5A Spinning bioreactor with cerebral organoids
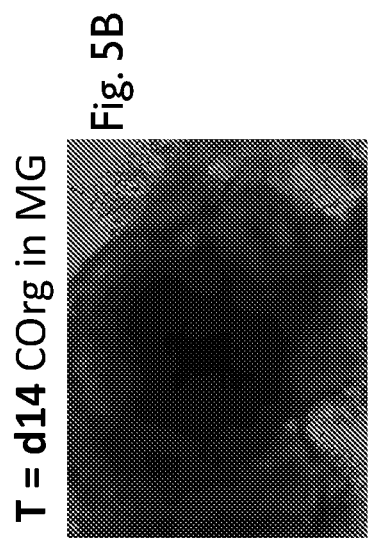
Fig. 5B T = d14 COrg in MG
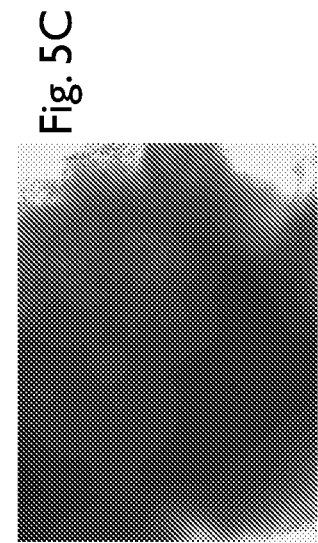
Fig. 5C T = d22 COrg in MG

Generating Cerebral Organoids
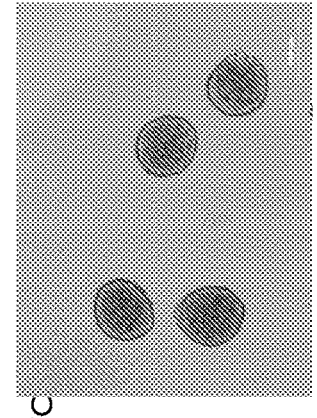
Fig. 7C  T = 1d Harvested EB's
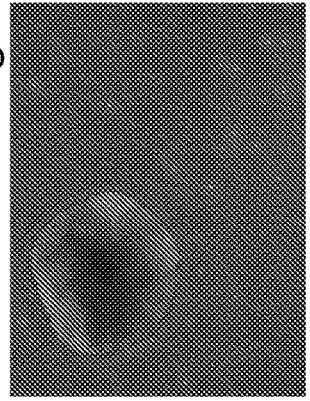
Fig. 7F  T = d8 COrg
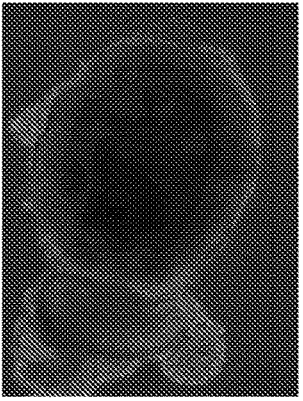
Fig. 7I  T = d12 COrg in MG
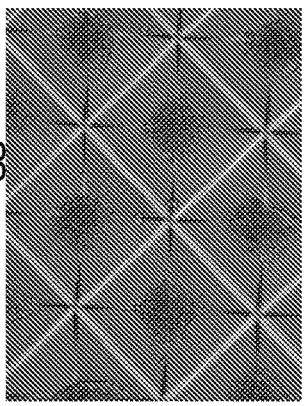
Fig. 7B  T = 1d Aggrewell
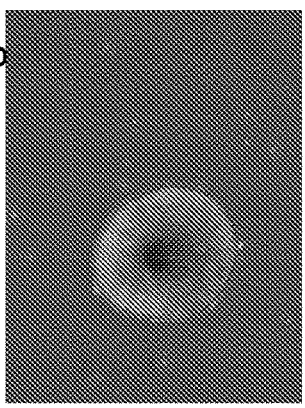
Fig. 7E  T = d7 COrg
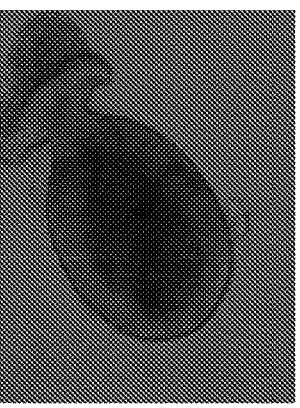
Fig. 7H  T = d11 COrg in MG
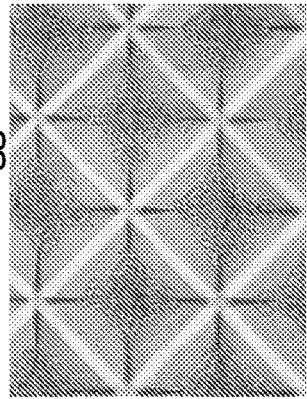
Fig. 7A  T = 0d Aggrewell
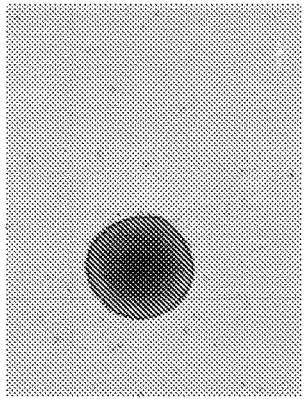
Fig. 7D  T = 5d EB's
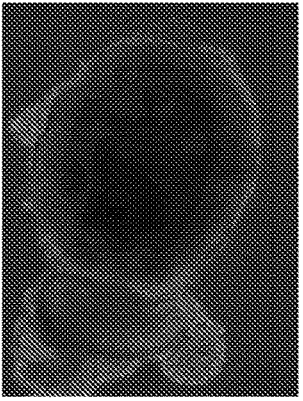
Fig. 7G  T = d10 COrg Cultured cerebral organoids contain an internal vascular plexus 3d Aggrewell Medium
5d Neural Induction Medium
5d Neural Differentiation Medium (phase 1)
5d Neural Differentiation Medium (phase 2)

3d Aggrewell Medium
5d Brain Microvascular Endothelium Medium
5d Neural Differentiation Medium (phase 1)
5d Neural Differentiation Medium (phase 2)

Culture Conditions

Delivery of multiple transcription factors into cells to produce mixed organoids

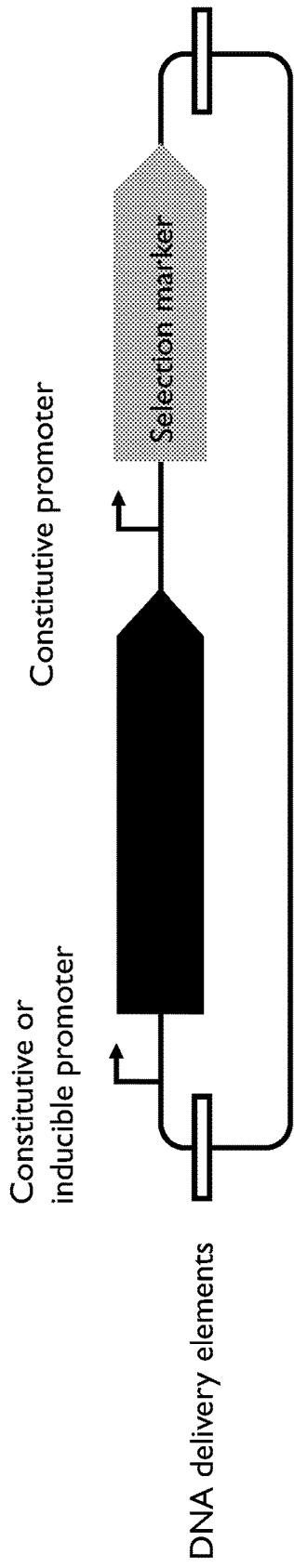

Promoters:
1. Constitutive (e.g. EF1alpha, PGK, Ubiquitin, CMV)
2. Small molecule inducible (e.g. doxycycline, cumate)
3. Cell-autonomous (e.g. cell type-specific promoters such as DCX)
4. Cell non-autonomous (e.g. heat induced, light induced)

DNA delivery elements:
1. Lentiviral inverted repeats, packaging signal (e.g. pLIX403 vector)
2. Transposon integration elements (e.g. PiggyBac vector)
3. Episomal replication elements
4. No mammalian elements (e.g. transient expression by electroporation or lipofection)

Selection markers:
1. Drug resistance (e.g. puromycin, neomycin, blasticidin)
2. No selection (e.g. transient expression followed by dilution from cell division)

Figure 11

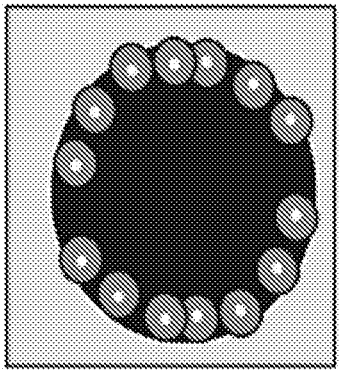
Fig. 14A
Print Endothelial cells
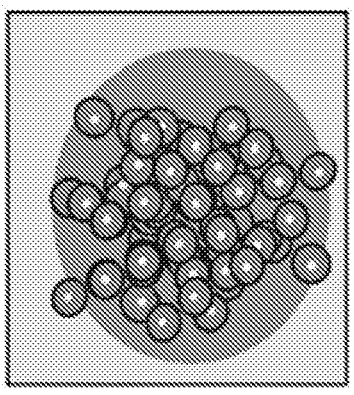
Fig. 14B
Matrix encapsulation
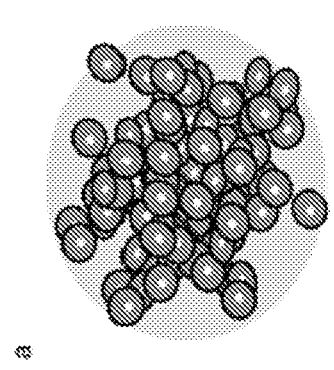
Fig. 14C
Evacuate
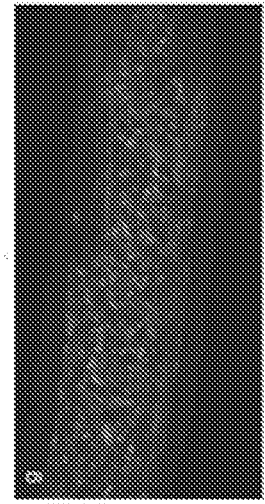
Fig. 14D
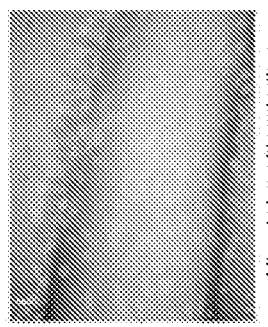
Fig. 14E
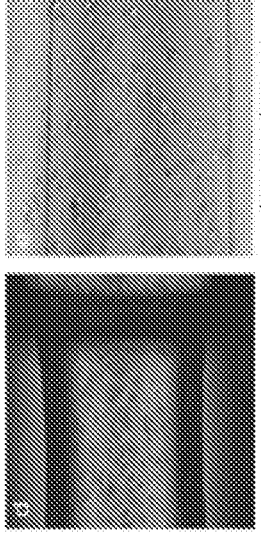
Fig. 14F
Fig. 14G The 3D printed artero-venous plexus Two spanning, non-intersecting branched vascular networks to enable natural capillary development to connect arterial and venous networks.

A 3D printed interface device for perfusing organoids

Introducing the Embryoid Body

The embryoid body will be introduces by infilling a column of pluronic

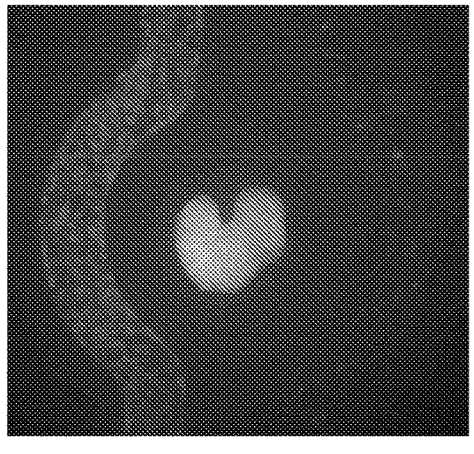
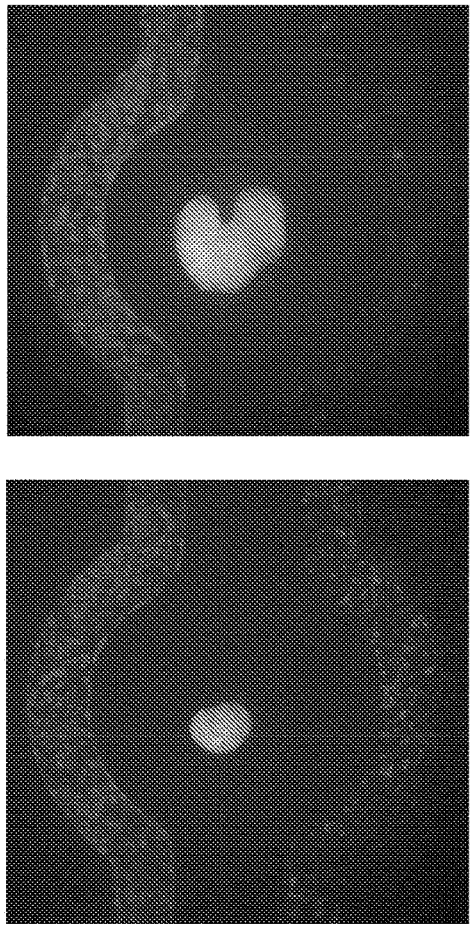
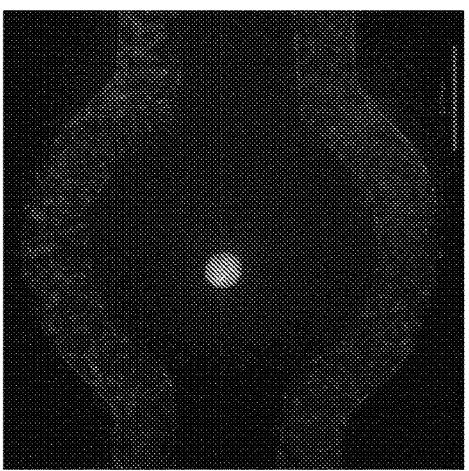
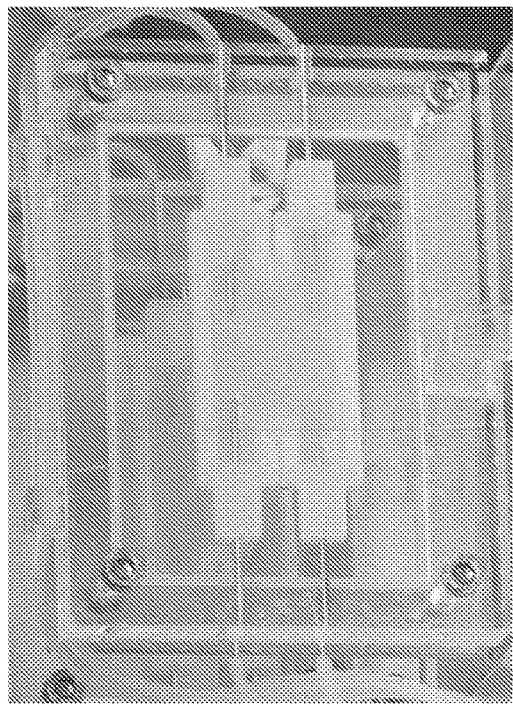
Fig. 22A Day 2
Fig. 22B Day 3
Fig. 22C Day 5
Fig. 22D
Embedding of sprouting organoid around printed vasculature Staining of sprouting EB's confirm endothelial progenitors

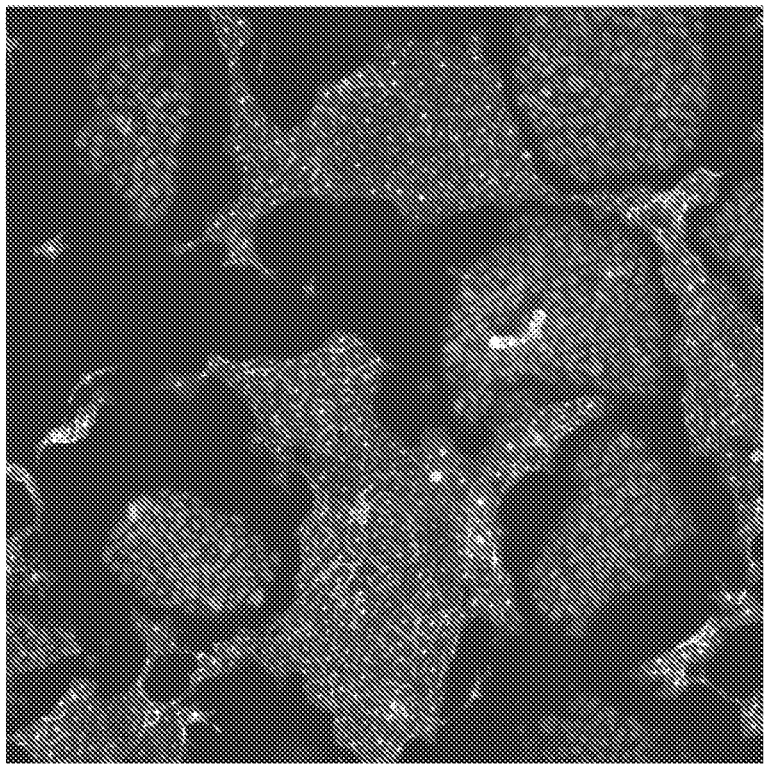
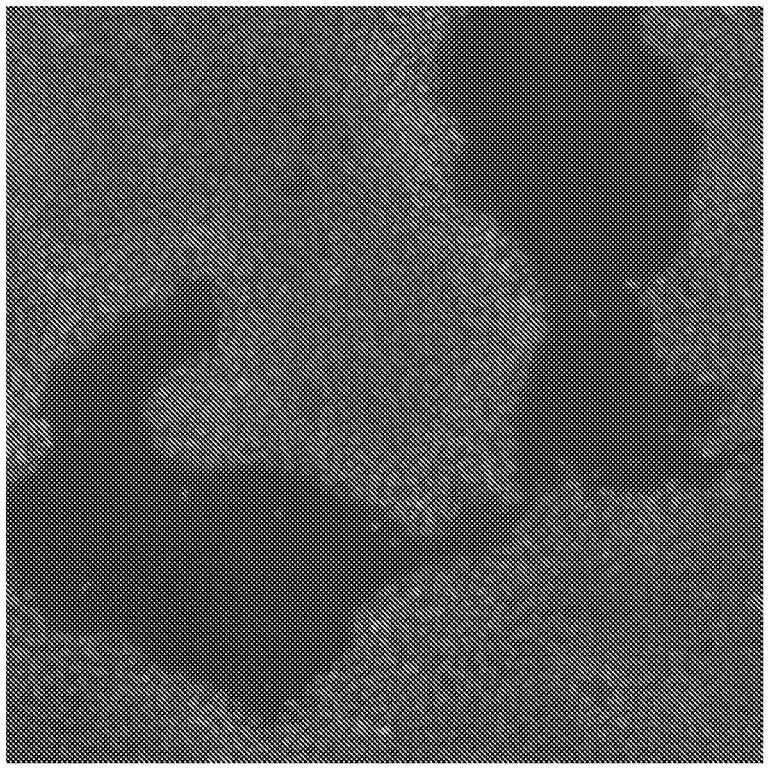
VE-Cad
Oct 4
PECAM-1
DAPI
Figure 35

10 Days Cultured in Matrigel Using Cerebral Organoid Culture Conditions

By adding PMA, a PKC activator, we can dramatically increase vascular sprouting

However, PKC also mediates neurite outgrowth, and would likely interfere with cerebral organoid development → Orthogonal drug inducible PKC-CA Titrating percentage of wildtype vs. ETV2 inducible cells A cerebro-vascular organoid

METHODS OF GENERATING FUNCTIONAL HUMAN TISSUE

RELATED APPLICATIONS

The present patent document is a § 371 filing based on PCT Application Serial No. PCT/US2016/020601, filed Mar. 3, 2016, which claims the benefit of the filing date under 35 U.S.C. § 119(e) of Provisional U.S. Patent Application Ser. No. 62/127,549, filed Mar. 3, 2015; Provisional U.S. Patent Application Ser. No. 62/250,338, filed Nov. 3, 2015; and U.S. Patent Application Ser. No. 62/294,118, filed Feb. 11, 2016, which are hereby incorporated by reference.

FEDERALLY SPONSORED RESEARCH OR DEVELOPMENT

This invention was made with Government support under Grant No. IRMIHG008525-01, awarded by the National Institute of Health (NIH). The Government has certain rights in this invention.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

BACKGROUND

The ability to create three-dimensional (3D) vascularized tissues on demand could enable scientific and technological advances in tissue engineering, drug screening, toxicology, 3D tissue culture, and organ repair. To produce 3D engineered tissue constructs that mimic natural tissues and, ultimately, organs, several key components—cells, extracellular matrix (ECM), and vasculature—may need to be assembled in complex arrangements. Each of these components plays a vital role: cells are the basic unit of all living systems, ECM provides structural support, and vascular networks provide efficient nutrient and waste transport, temperature regulation, delivery of factors, and long-range signaling routes. Without perfusable vasculature within a few hundred microns of each cell, three-dimensional tissues may quickly develop necrotic regions. The inability to embed vascular networks in tissue constructs has hindered progress on 3D tissue engineering for decades.

Classical experiments performed half a century ago demonstrated the immense self-organizing capacity of vertebrate cells. Even after complete dissociation, cells can reaggregate and reconstruct the original architecture of an organ. More recently, this outstanding feature was used to rebuild organ parts or even complete organs from tissue or embryonic stem cells. Such stem cell-derived three-dimensional cultures are called organoids. Because organoids can be grown from human stem cells and from patient-derived induced pluripotent stem cells, they have the potential to model human development and disease and in a tree-dimensional, biomimetic environment (Lancaster M A, et al., Cerebral organoids model human brain development and microcephaly. Nature 501 (7467):373-9 (2013)). Furthermore, they have potential for drug testing and even future organ replacement strategies (Lancaster et al., 2013). The organoids are often developed in spinning bioreactors.

New methods of creating embryoid bodies or organoids and tissue constructs suitable for studies of tissue development and disease, as well as transplantation are desired.

SUMMARY

Methods of tissue engineering, and more particularly methods and compositions for generating various vascularized 3D tissues, such as 3D vascularized embryoid bodies and organoids are described.

Certain embodiments relate to a method of generating functional human tissue, the method comprising embedding an embryoid body or organoid in a tissue construct comprising a first vascular network and a second vascular network, each vascular network comprising one or more interconnected vascular channels; exposing the embryoid body or organoid to one or more biological agents, a biological agent gradient, a pressure, and/or an oxygen tension gradient, thereby inducing angiogenesis of capillary vessels to and/or from the embryoid body or organoid; and vascularizing the embryoid body or organoid, the capillary vessels connecting the first vascular network to the second vascular network, thereby creating a single vascular network and a perfusable tissue structure. The one or more biological agents include one or more of growth factors, morphogens, small molecules, drugs, hormones, DNA, shRNA, siRNA, nanoparticles, mRNA, and modified mRNA. The one or more interconnected vascular channels may be formed by a manufacturing process or by a biological developmental process that may include at least one of vasculogenesis, angiogenesis, or tubulogenesis. The one or more biological agents, the biological agent gradient, the pressure, and/or the oxygen tension gradient may further direct development, differentiation, and/or functioning of the embryoid body or organoid. The first vascular network and the second vascular network may be independently addressable. The first vascular network and the second vascular network may not be in contact with each other. The first vascular network may comprise an arterial plexus and the second vascular network may comprise a venous plexus. The single vascular network may comprise an interpenetrating vascular network and/or a branched interpenetrating vascular network. The single vascular network may comprise interconnected arterial and venous channels. The embryoid body or organoid may be created by culturing at least one of: pluripotent stem cells, multipotent stem cells, progenitor cells, terminally differentiated cells, endothelial cells, endothelial progenitor cells, immortalized cell lines, or primary cells. The embryoid body or organoid may be created by culturing pluripotent or multipotent stem cells. The culturing may take place on a low-adhesion substrate, via a hanging drop method, via aggregation in microwells, via aggregation in microchannels, or by using a spinning bioreactor. In the method, prior to, during and/or after the embedding, the embryoid body or organoid may be further differentiated into a tissue containing at least one of pluripotent stem cells, multipotent stem cells, progenitor cells, terminally differentiated cells, endothelial cells, endothelial progenitor cells, immortalized cell lines, or primary cells. The embryoid body or organoid may be a cerebral organoid, thyroid organoid, intestinal or gut organoid, hepatic organoid, pancreatic organoid, gastric organoid, kidney organoid, retinal organoid, cardiac organoid, bone organoid, cancer organoid, or epithelial organoid. The embryoid body or organoid may be exposed to the one or more biological agents and/or the biological agent gradient due to diffusion of the one or more biological agents within the tissue construct. Alternatively or in addition, the embryoid body or organoid may be exposed to the one or more biological agents and/or the biological agent gradient by localized deposition of materials loaded with the one or more biological agents within the tissue construct. Alternatively or in addition, the embryoid body or organoid may be exposed to the one or more biological agents and/or the biological agent gradient by localized de-novo production of growth factors by localized protein translation. Alternatively or in addition, the embryoid body or organoid may be exposed to the one or more biological agents and/or the biological agent gradient via perfusion of one or both of the first and second vascular networks with the one or more biological agents. In the method, only one of the first and second vascular networks may be perfused with the one or more biological agents. Alternatively, both the first and second vascular networks may be perfused with the one or more biological agents, and a biological agent concentration in the first vascular network is different than a biological agent concentration in the second vascular network. Alternatively, both the first and second vascular networks are perfused with the one or more biological agents, and a biological agent concentration in the first vascular network is the same as a biological agent concentration in the second vascular network. The biological agents may include one or more of the following growth factors or small molecules: vascular endothelial growth factor (VEGF), basic fibroblast growth factor (bFGF), sphingosine-1-phosphate (S1P), phorbol myristate acetate (PMA), hepatocyte growth factor (HGF), monocyte chemotactic protein-1 (MCP-1), the angiopoietin ANG-1, the angiopoietin ANG-2, transforming growth factor beta (TGF-β), epidermal growth factor (EGF), human growth factor, matrix metalloproteinases (MMP's), doxycycline, and histamine. In the method, an oxygen partial pressure gradient may be introduced to one or both of the first and second vascular networks during perfusion. The oxygen partial pressure gradient may be formed by introducing deoxygenated media into one of the first and second vascular networks, and by introducing oxygenated media into the other of the first and second vascular networks. The media may be deoxygenated using either continuous bubbling of nitrogen gas through media, and/or by adding the enzymes glucose oxidase and catalase in the presence of glucose. The perfusion may be carried out at a flow rate of from about 1 microliter per minute to about 1 liter per minute. In the method, one or both of the first and second vascular networks may be subjected to a transmural pressure during the perfusion. In the method, prior to embedding the embryoid body or organoid in the tissue construct, the embryoid body or organoid may be encapsulated in an extracellular matrix material. The extracellular matrix material may comprise a gel. In the method, the embryoid body or organoid may comprise a first population of embryoid body or organoid cells and a second population of embryoid body or organoid cells, where the embryoid body or organoid may comprise at least two of: pluripotent stem cells, multipotent stem cells, progenitor cells, terminally differentiated cells, endothelial cells, endothelial progenitor cells, immortalized cell lines, neural cells, primary cells, or a combination thereof.

In certain embodiments, the embryoid body or organoid may be created by culturing a wild-type population of cells and a genetically-engineered inducible population of cells in a medium, inducing direct differentiation and/or transdifferentiation of the genetically-engineered inducible population of cells into the first population of the embryoid body or organoid cells, inducing differentiation of the wild-type population of cells into the second population of the embryoid body or organoid cells, and thereby forming the embryoid body or organoid comprising at least the first population of the embryoid body or organoid cells and the second population of embryoid body or organoid cells. The genetically-engineered inducible population of cells may be created by introducing a DNA delivery element comprising at least one of constitutive promoter, small molecule inducible promoter, cell-autonomous promoter, cell non-autonomous promoter, selection marker, or a combination thereof. The first population of the embryoid body or organoid cells may comprise pluripotent stem cells, multipotent stem cells, progenitor cells, terminally differentiated cells, endothelial cells, endothelial progenitor cells, immortalized cell lines, or primary cells. The second population of the embryoid body or organoid cells may comprise neural progenitor cells, where the neural progenitor cells can form at least one of excitatory neurons, inhibitory interneurons, motor neurons, dopaminergic neurons, pain receptor neurons, astrocytes, oligodendrocyte progenitor cells, and/or oligodendrocytes. The step of inducing direct differentiation and/or transdifferentiation of the genetically-engineered inducible population of cells may comprise introducing at least one cue selected from the group consisting of transcription factors, drugs, small molecules, growth factors, morphogens, hormones, DNA, shRNA, siRNA, nanoparticles, mRNA, modified mRNA, heat, light, and mechanical force. The induced direct differentiation and or transdifferentiation may be accompanied by a secondary gene induction. The secondary gene induction may be via providing at least one cue selected from the group consisting of transcription factors, drugs, small molecules, growth factors, morphogens, hormones, DNA, shRNA, siRNA, nanoparticles, mRNA, modified mRNA, heat, light, and mechanical force. The cue selected for the secondary gene induction may be the same as the cue selected for the step of inducing direct differentiation and/or transdifferentiation of the genetically-engineered inducible population of cells, or may be different. The first population of the embryoid body or organoid cells can undergo further development due to induction of a secondary gene. The induction of the secondary gene may induce an expression of a constitutively-active protein kinase C (PKC) protein thereby enhancing at least one of an endothelial sprouting behavior of the first population of the embryoid body or organoid cells and neurite outgrowth. The first population of the embryoid body or organoid cells is endothelial cells. The step of culturing can take place on a low-adhesion substrate, via a hanging drop method, via aggregation in microchannels, via aggregation in microwells, or by using a spinning bioreactor. The ratio of the first population the embryoid body or organoid cells to the second population of the embryoid body or organoid cells may be 1:1. Other ratios are also considered (e.g., 1:2, 1:3, 1:4, etc., 2:1, 3:1, 4:1, etc.). The step of culturing may be in a differentiation medium. The differentiation medium may comprise doxycycline (DOX) or other drugs associated with drug-inducible promoters. The one or more interconnected vascular channels may be formed by a manufacturing process or by a biological developmental process that may include at least one of vasculogenesis, angiogenesis, or tubulogenesis. The one or more biological agents, the biological agent gradient, the pressure, and/or the oxygen tension gradient may further direct development, differentiation, and/or functioning of the embryoid body or organoid. The wild-type population of cells may comprise induced pluripotent stem cells (iPSCs) or iPSCs-derived patent-specific cell lines.

In the above methods, the step of embedding the embryoid body or organoid in the tissue construct comprises depositing one or more cell-laden filaments each comprising a plurality of viable cells on a substrate to form one or more tissue patterns, each of the tissue patterns comprising one or more predetermined cell types, depositing one or more sacrificial filaments on the substrate to form a vascular pattern interpenetrating the one or more tissue patterns, each of the sacrificial filaments comprising a fugitive ink, depositing the embryoid body or organoid within the vascular pattern, at least partially surrounding the one or more tissue patterns and the vascular pattern with an extracellular matrix composition, and removing the fugitive ink, thereby forming the tissue construct comprising the embryoid body or organoid embedded therein.

In certain embodiments, at least some portion of the one or more cell-laden filaments may comprise the one or more biological agents.

One or both of the first and second vascular networks comprise microfluidic channels.

In certain further embodiments, a plurality of the embryoid bodies or organoids may be embedded in the tissue construct. The embryoid bodies or organoids may comprise different phenotypes or may comprise the same phenotype.

In certain embodiments, the above methods, wherein an array of the tissue constructs is present, wherein the embedding, exposing and vascularizing may be carried out in each tissue construct.

Certain further embodiments relate to a functional human tissue or an array of functional human tissues formed by the method described herein.

These and other features and advantages of the invention will become apparent upon consideration of the following detailed description of the presently preferred embodiments, viewed in conjunction with the appended drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5A depicts a photograph of a spinning bioreactor with cerebral organoids.

FIG. 5B depicts an organoid grown in a spinning bioreactor at day 14.

FIG. 5C depicts an organoid grown in a spinning bioreactor at day 22.

FIG. 7A shows an image of an organoid taken at T=0 d.

FIG. 7B shows an image of a developing organoid taken at T=day 1.

FIG. 7C shows an image of an organoid harvested at T=day 1.

FIG. 7D shows an image of a developing organoid taken at T=day 5.

FIG. 7E shows an image of a developing organoid taken at T=day 7.

FIG. 7F shows an image of a developing organoid taken at T=day 8.

FIG. 7G shows an image of a developing organoid taken at T=day 10.

FIG. 7H shows an image of a developing organoid taken at T=day 11 in matrigel (MG).

FIG. 7I shows an image of a developing organoid taken at T=day 12 in matrigel (MG).

FIG. 11 depicts a schematic illustration of a DNA delivery element used for delivery of multiple transcription factors into cells to produce mixed population organoids.

FIGS. 14A-14G depict a method of producing a network of vascular channels in the extracellular matrix composition

FIG. 22A shows embedding embryoid bodies into vascularized tissues (day 2).

FIG. 22B shows embedding embryoid bodies into vascularized tissues (day 3).

FIG. 22C shows embedding embryoid bodies into vascularized tissues (day 5).

FIG. 22D shows an exemplary perfusion chip that is connected to an external for implanting and perfusing the sprouting organoid.

FIG. 27, right image, shows the tubular morphology of the cells.

FIG. 31 shows 'common sense' approach of mixing human umbilical-vein endothelial cells (HUVECs) with induced pluripotent stem cells (iPSCs).

FIG. 35 shows iPSCs that were transformed with a dox-inducible ETV2 vector and cultured in mTeSR1 containing dox for 5 days.

DETAILED DESCRIPTION

Figure 1:
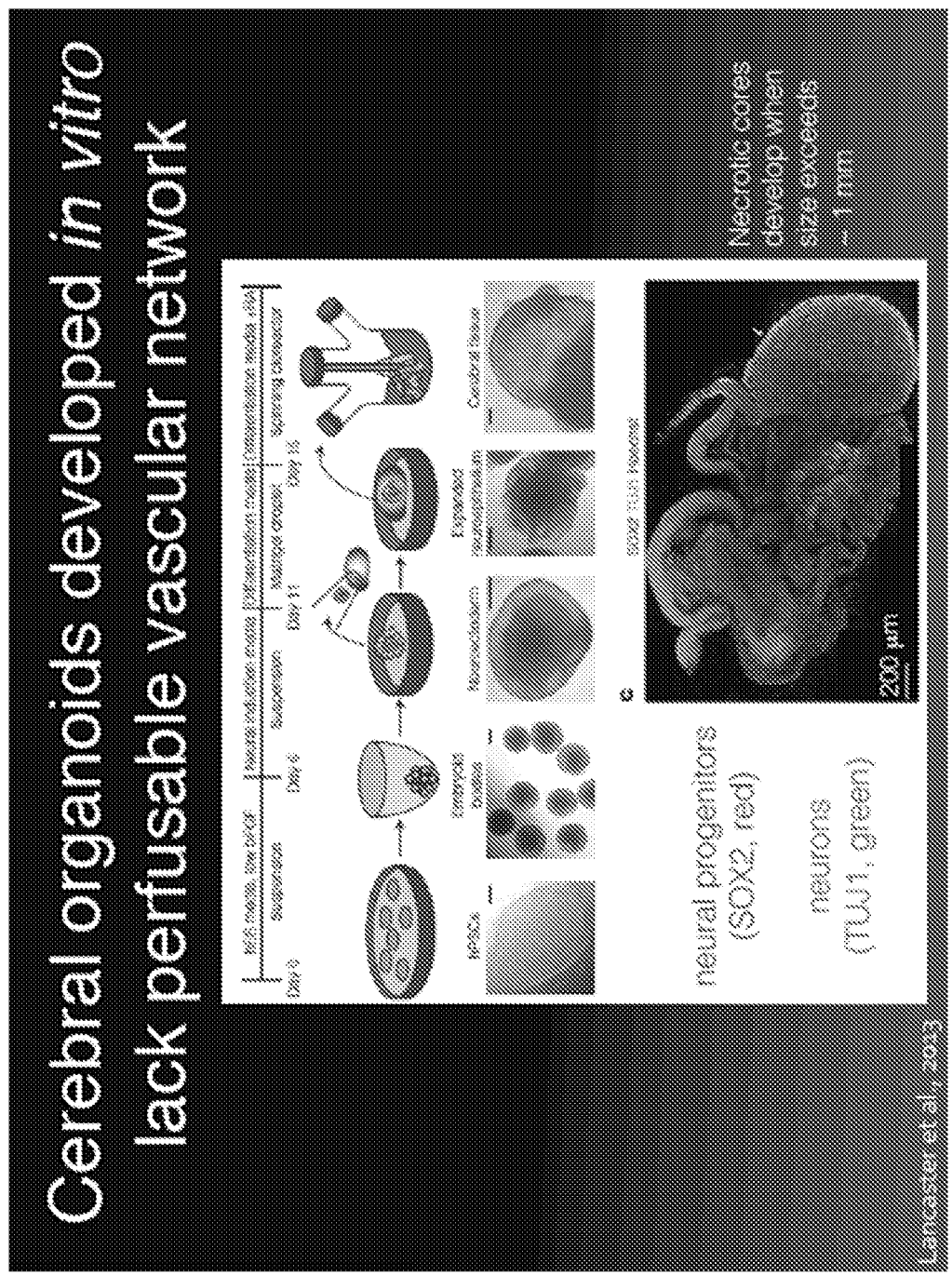
FIG. 1 depicts results of a study by Lancaster et al. (Lancaster et al., 2013) where the cerebral organoids developed in vitro lacked a perfusable vascular network.

Embryoid bodies or organoids (e.g., cerebral organoids) are a promising platform for studying tissue development processes (e.g., neurodevelopment processes) in a three dimensional, biomimetic environment. However, previously developed organoids lacked a perfusable vasculature. Due to a lack of a pervasive, perfusable vasculature, the organoids were developing necrotic cores once their size exceeded approximately 1 mm in diameter (FIG. 1; Lancaster et al., 2013)).

A new approach has been developed and described in the present disclosure for creating vascularized embryoid bodies or organoids via three-dimensional (3D) bioprinting. This highly scalable platform enables the fabrication of engineered embryoid bodies or organoids in which vasculature, multiple cell types and optionally other functional chemical substances, such as drugs, toxins, proteins and/or hormones, are programmably placed at desired locations within an extracellular matrix. This technique may lead to the rapid manufacturing of functional 3D tissues (i.e., "tissue constructs") and organs needed for studies of tissue development and disease, as well as transplantation. The inventive vascularized embryoid bodies or organoids can also be used as a research tool to study the effects of any external (e.g. drugs or other stimuli) or internal (mutations) influences on growth and activity of cells in the tissue.

Examples of organ, embryoid body, organoid, or tissue constructs that can be produced by the described methods include, but are not limited to, thyroid, pancreas, ureters, bladder, urethra, adrenal glands, lung, liver, pineal gland, pituitary gland, parathyroid glands, thymus gland, adrenal glands, appendix, gallbladder, spleen, prostate gland, reproductive organs, neural and vascular tissue.

Figure 2:
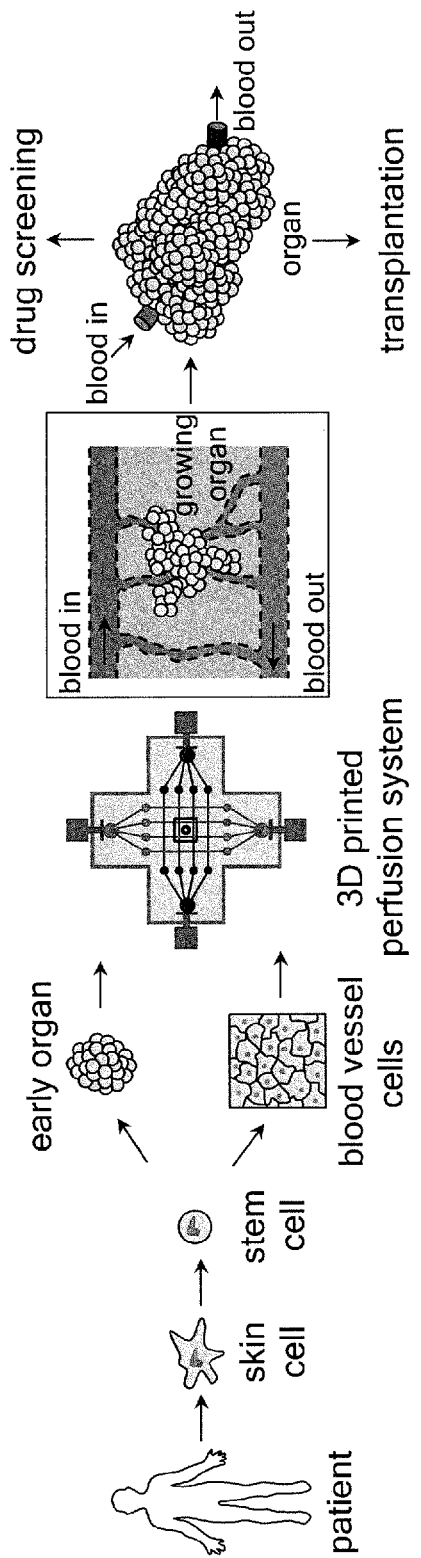
FIG. 2 depicts an illustration of the concept of growing a developing embryoid body or organoid with an internal developing vascular plexus beginning with a single cell to vascularized organ.

As such, certain embodiments relate to methods of creating vascularized developing embryoid bodies or organoids (e.g., cerebral organoids) to enable nutrient delivery via perfusion necessary for generation of larger, more complex embryoid bodies or organoids for transplantation and drug screening applications, as well as for fundamental, long term studies of organogenesis. A printed vascularized embryoid body or organoid and a method of creating the embryoid body or organoid with an internal developing vascular plexus are described herein. FIG. 2 provides an illustration of the concept of growing a developing embryoid body or organoid with an internal developing vascular plexus adjacent to brain microvascular endothelial cell (BMEC)-lined printed microchannels beginning with a single cell to a vascularized organ that has anastomosed with the adjacent channels. The process combines a 3D printing approach with developmental biology to generate vascularized, functional human tissues for drug development and regenerative medicine applications. Previous technologies described approaches of developing avascular organoids or printing blood vessels to maintain adult cell viability. In contrast, described here are methods that employ combination of autologous, printed blood vessels with developing embryoid bodies or cell organoids inside a 3D printed perfusion system.

As used herein and in the appended claims, the singular forms "a," "and," and "the" include plural referents unless the context clearly dictates otherwise. Thus, for example, reference to "a protein" includes a plurality of such proteins and reference to "the progenitor cell" includes reference to one or more progenitor cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, compositions, devices and materials are described herein.

The term "embryoid body" refers to a plurality of cells containing pluripotent or multipotent stem cells formed into a three dimensional sphere, spheroid, or other three dimensional shape.

The term "organoid" refers to an embryoid body whose cells have undergone a degree of differentiation.

The embryoid body or organoid is created by culturing at least one of pluripotent stem cells, multipotent stem cells, progenitor cells, terminally differentiated cells, endothelial cells, endothelial progenitor cells, immortalized cell lines, or primary cells, which will be described in detail below.

We acknowledge that the distinction between an embryoid body and organoid remains undefined, and the use of the terms should be considered interchangeable.

The embryoid body or organoid may be a cerebral organoid, thyroid organoid, intestinal organoid, gut organoid, hepatic organoid, pancreatic organoid, gastric organoid, kidney organoid, retinal organoid, cardiac organoid, bone organoid, and epithelial organoid.

The term "cerebral organoid" refers to an artificial three-dimensional tissue culture created by culturing human pluripotent stem cells in, e.g., a three-dimensional rotational bioreactor. Cerebral organoids may be synthesized tissues that contain several types of nerve cells and have anatomical features that resemble mammalian brains. For example, cerebral organoids can comprise a heterogenous population of cells of at least two different progenitor and neuronal differentiation layers. The cerebral organoids can display heterogeneous regionalization of various brain regions as well as development of complex, well-organized cerebral cortex. Cerebral organoids are most similar to layers of neurons called the cortex and choroid plexus. In some cases, structures similar to the retina, meninges and hippocampus can form as well.

The term "internal plexus" refers to an interconnected network of vascular endothelial cells that resides inside of, and/or on the surface of a developing embryoid body or organoid.

A pattern or network that "interpenetrates" another pattern or network in a printed tissue construct may be understood to comprise one or more filaments, channels or portions that are layered with, partially or completely overlapping, partially or completely underlapping, surrounding, embedded within, and/or interwoven with one or more filaments, channels or portions of the other pattern or network. A filament "deposited on a substrate" may be understood to be deposited directly on the substrate or directly on another filament, channel or portion previously deposited or formed on the substrate.

The term "PKC" is used as an acronym for protein kinase C, which may refer to any of the isoforms of protein kinase C, including PKC-alpha, PKC-beta1, PKC-beta2, PKC-gamma, PKC-delta, PKC-epsilon, PKC-eta, PKC-theta, PKC-iota, and PKC-zeta.

The term "orthogonal promoters," refers to two different promoter designs for which there are independent cues for gene induction. For example, if there are two inducible genes, 'gene 1' activated by 'promoter 1', and 'gene 2' activated by 'promoter 2', then promoter 1 and 2 are orthogonal if both of the following statements hold true:

1) There exists a 'cue 1' that specifically induces the expression of 'gene 1' without directly affecting the expression of 'gene 2'; and 2) There exists a 'cue 2' that specifically induces the expression of 'gene 2' without directly affecting the expression of 'gene 1'.

The term "sprouts," or more specifically, "endothelial sprouts," refers to endothelial structures that have either undergone angiogenesis or vasculogenesis to generate tubular structures.

The term "functional" as it refers to generating human tissue, means that the tissue synthesized according to the described methods have the same or similar functions to the organ intended to be created.

Figure 3I:
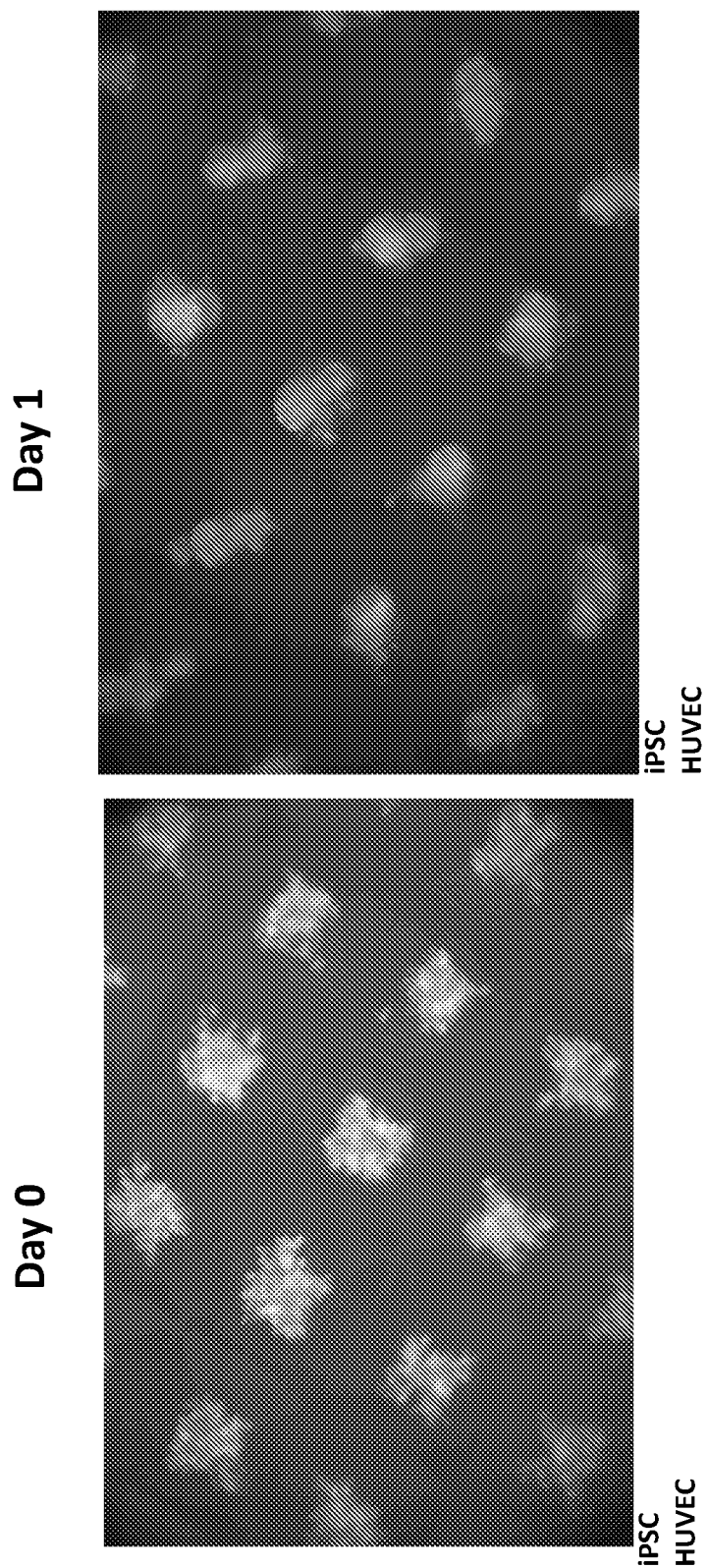
FIG. 3A depicts an illustration of a strategy to develop cell organoids inside a 3D printed perfusion system. The 'original strategy' involves eliciting angiogenesis from endothelial cell lined printed microchannels, whereby the sprouting endothelium invades the implanted organoids.
FIG. 3B depicts an illustration of an alternative strategy to develop cell organoids inside a 3D printed perfusion system. The 'revised strategy' involves eliciting angiogenesis from a population of endothelial cells contained within the organoid or embryoid body and attracting the sprouts towards the printed channels, whereupon they connect the arterial and venous networks.

As shown in FIGS. 3A-B, two possible strategies to develop cell organoids inside a 3D printed perfusion system are considered.

In the first strategy, shown schematically in FIG. 3A, stem cells are cultured in embryoid body growth medium, for example Aggrewell™ medium from StemCell Technologies Inc. (AW) to develop an embryoid body and, separately, in Brain Microvasculature Differentiation Medium (BMEC) (Lippmann E S, et al. Derivation of blood-brain barrier endothelial cells from human pluripotent stem cells. Nat Biotechnol 30(8):783-91 (2012)) to develop brain microvascular endothelial cells. The BMECs are then introduced into 3D printed, perfusable arterial microchannels and are allowed to adhere to the channel walls. Next, a gradient of biological factors may added to the venous channel to induce sprouting angiogenesis that anastomoses with an internal vascular plexus in the developing organoid. Once the endothelial sprouts span the space between the arterial and venous network, the embryoid body or organoid can be directly perfused via an external pump.

In the second strategy, shown schematically in FIG. 3B, stem cells can be incubated in AW to produce an embryoid body, which is then incubated in BMEC or neural induction medium (NIM) (Lancaster et al., 2013) to produce a sprouting embryoid body. The sprouting embryoid body is then incubated in NIM with EGM and placed into a 3D printed perfusion system to produce a vascularized organ.

Figure 4:
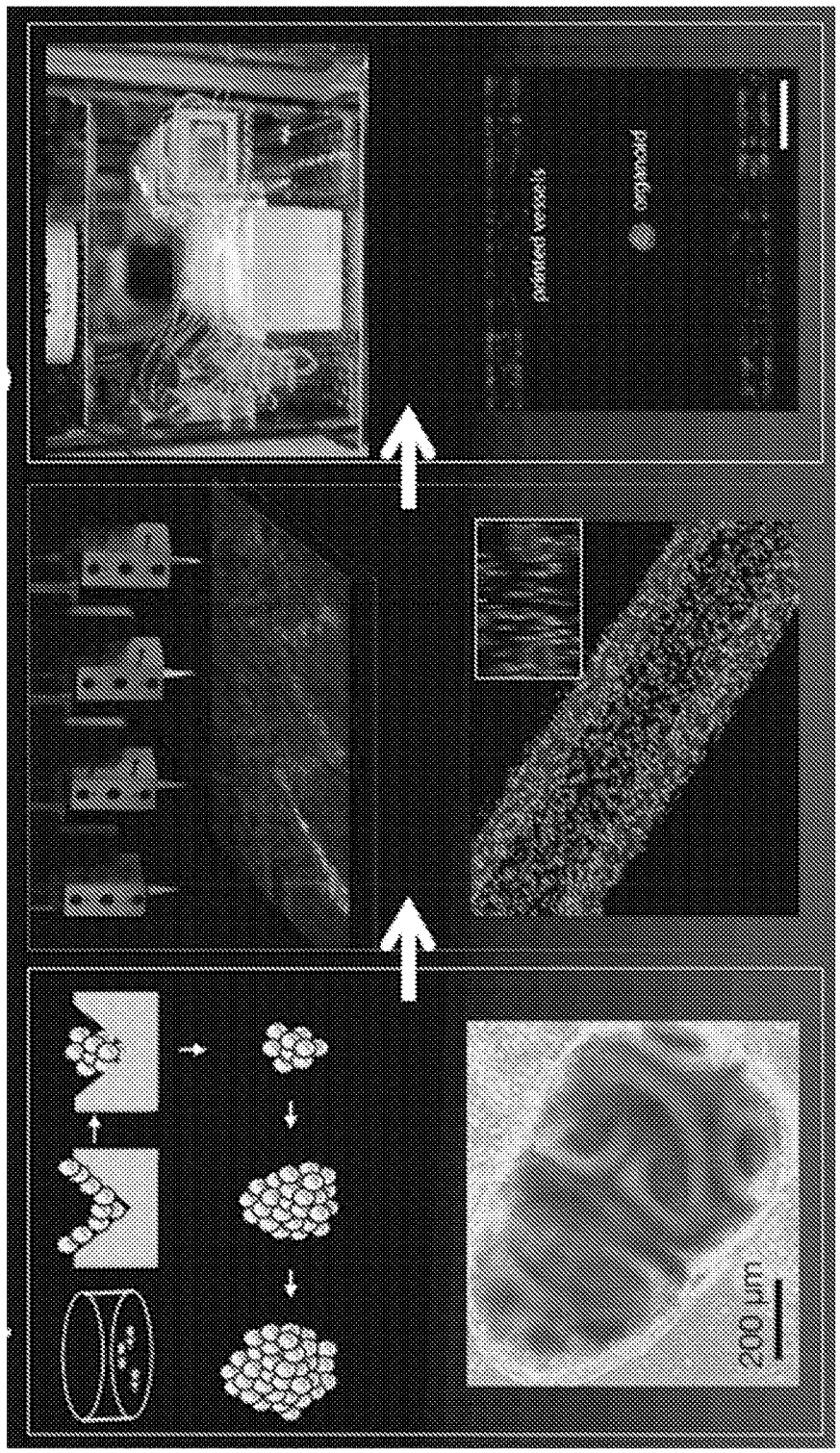
FIG. 4 depicts a strategy for creating perfusable vascularized organoids.

The second strategy is further illustrated in FIG. 4, wherein the cerebral organoids grown in vitro are placed within printed vasculature, embedded and grown on a chip.

Methods for culturing and differentiating stem cells into neuronal cells and tissues are known from Eiraku (2008), US 2011/0091869 A1 and WO 2011/055855 A1, contents of which are incorporated by reference in their entirety. Methods described in U.S. Pat. Pub. No. US 2015/0330970 to Lancaster et al. and Lancaster et al., "Cerebral organoids model human brain development and microcephaly," *Nature* 501, 373-379 (2013)), incorporated by reference herein, can be used in the first step of obtaining the embryoid bodies or organoids, especially the steps of providing a multicellular aggregation of pluripotent stem cells and culturing the multicellular aggregation in neural induction medium.

The cells used to produce embryoid bodies or organoids (including all further embodiments related thereto), are human cells or non-human primate cells, pluripotent stem cells, multipotent stem cells, progenitor cells, terminally differentiated cells, endothelial cells, endothelial progenitor cells, immortalized cell lines, or primary cells.

A "pluripotent" stem cell is not able to grow into an entire organism, but is capable of giving rise to cell types originating from all three germ layers, i.e., mesoderm, endoderm, and ectoderm, and may be capable of giving rise to all cell types of an organism. Pluripotency can be a feature of the cell per se, e.g. in certain stem cells, or it can be induced artificially. E.g. in certain embodiments, the pluripotent stem cell is derived from a somatic, multipotent, unipotent or progenitor cell, wherein pluripotency is induced, Such a cell is referred to as "induced pluripotent stem cell" or "iPSC" herein. The somatic, multipotent, unipotent or progenitor cell can, e.g., be used from a patient, which is turned into a pluripotent cell, that is subject to the described methods. Such a cell or the resulting tissue culture can be studied for abnormalities, e.g. during tissue culture development according to the described methods. A patient may, e.g., suffer from a neurological disorder or cerebral tissue deformity. Characteristics of the disorder or deformity can be reproduced in the described embryoid bodies or organoids and investigated.

A "multipotent" cell is capable of giving rise to at least one cell type from each of two or more different organs or tissues of an organism, wherein the cell types may originate from the same or from different germ layers, but is not capable of giving rise to all cell types of an organism.

In contrast, a "unipotent" cell is capable of differentiating to cells of only one cell lineage.

A "progenitor cell" is a cell that, like a stem cell, has the ability to differentiate into a specific type of cell, with limited options to differentiate, with usually only one target cell. A progenitor cell is usually a unipotent cell, it may also be a multipotent cell, and often has a more limited proliferation capacity.

Preferably, the described embryoid body or organoid is created by culturing initial populations of pluripotent or multipotent stem cells.

In certain embodiments, the embryoid bodies or organoids can be obtained from culturing pluripotent stem cells. In principle, the cells may also be totipotent, if ethical reasons allow. A "totipotent" cell can differentiate into any cell type in the body, including the germ line following exposure to stimuli like that normally occurring in development. Accordingly, a totipotent cell may be defined as a cell being capable of growing, i.e. developing, into an entire organism.

The cells used in the methods according to the present invention are preferably not totipotent, but (strictly) pluripotent.

The culturing methods are known in the art. For example, culturing can take place on a low-adhesion substrate (Doetschman T C, et al., The in vitro development of blastocyst-derived embryonic stem cell lines: formation of visceral yolk sac, blood islands and myocardium. J Embryol Exp Morphol 87:27-45 (1985)), via a hanging drop method (Reubinoff B E, et al., Embryonic stem cell lines from human blastocysts: somatic differentiation in vitro. Nat Biotechnol 18(4):399-404 (2002)), via aggregation in microwells (Mohr J C, et al., 3-D microwell culture of human embryonic stem cells. Biomaterials 27(36):6032-42 (2006), via aggregation in microchannels (Onoe H, et al., Differentiation Induction of Mouse Neural Stem Cells in Hydrogel Tubular Microenvironments with Controlled Tube Dimensions. Adv Healthc Mater. (2016), doi:10.1002/adhm.201500903), or by using a spinning bioreactor (Carpenedo R L, et al., Rotary suspension culture enhances the efficiency, yield, and homogeneity of embryoid body differentiation. Stem Cells 25(9):2224-34 (2007)) (FIG. 5A). FIGS. 5B and 5C show organoids grown a spinning bioreactor at day 14 and day 22, respectively.

A typical embryoid body or organoid protocol, according to the described methods starts with isolated embryonic or pluripotent stem cells (e.g., induced pluripotent stem cells, or iPS cells, or iPSCs).

The organoid culture is in vitro grown (culturing step), i.e., it is not an isolated organ, such as brain or Kidney from an animal during any stages. Since it is grown from human pluripotent stem cells, this allows growth of human tissue without the need to obtain human fetal tissue samples.

Figure 6:
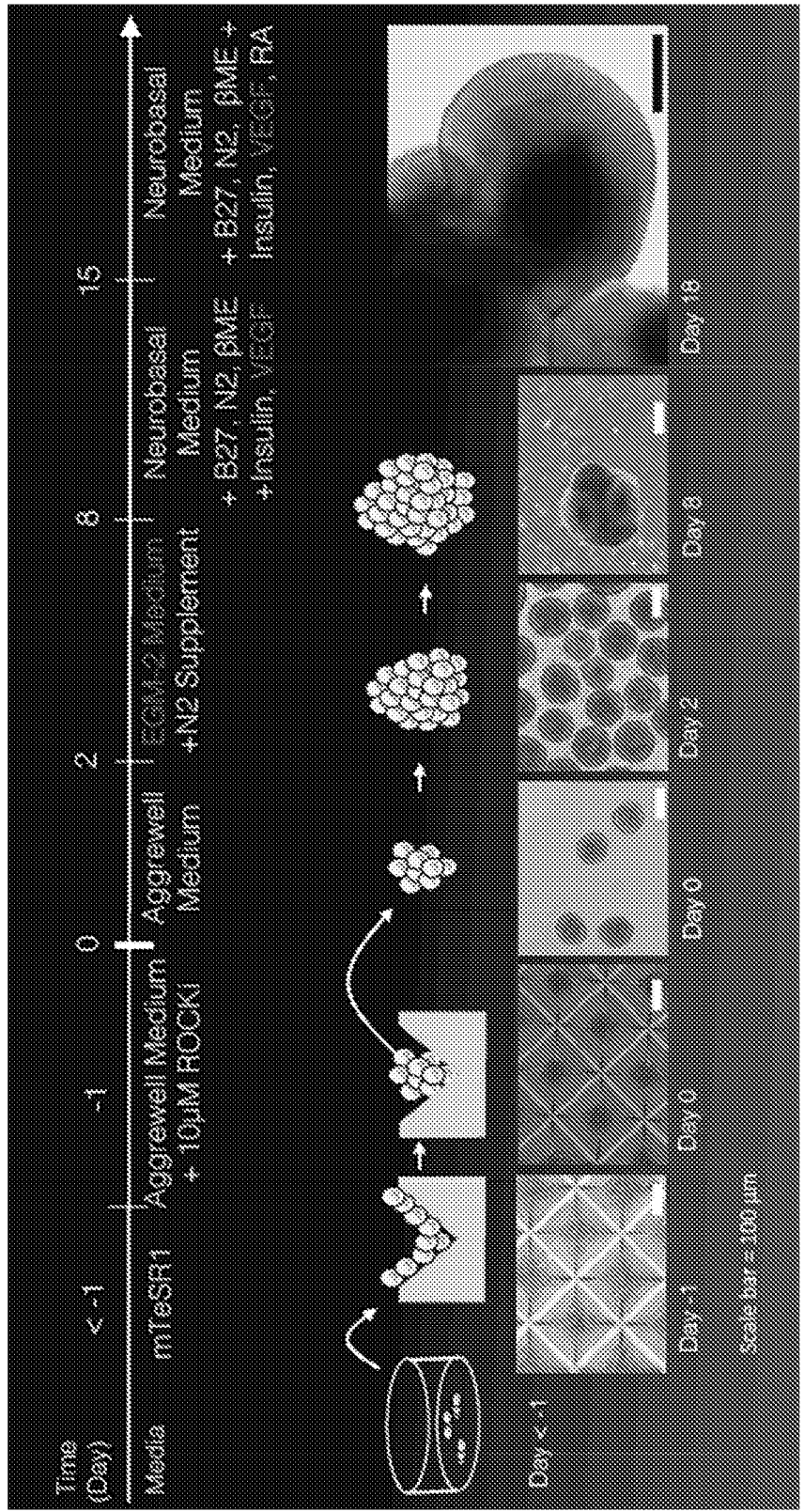
FIG. 6 depicts a schematic illustration of the culture system used to develop embryoid bodies or organoids from iPSCs and exemplary images or organoids taken at each stage of embryoid body or organoid development in vitro.

For example, during the step of culturing the aggregate, the pluripotent stem cells can be induced to differentiate into a tissue (e.g., neural tissue) containing at least one of pluripotent stem cells, multipotent stem cells, progenitor cells, terminally differentiated cells, endothelial cells, endothelial progenitor cells, immortalized cell lines, or primary cells. For providing a multicellular aggregation, it is, e.g., possible to culture pluripotent stem cells from the multicellular aggregates. For example, FIG. 6 shows a schematic illustration of the culture system used to develop embryoid bodies or organoids from iPSCs and exemplary images or organoids taken at each stage of embryoid body or organoid development in vitro. Differentiation of embryoid bodies towards early cerebral organoids can be seen by the development of neuroepithelial rosettes by day 8.

FIGS. 7A-I shows images of various organoids taken at various times during development and in various media. This will be described in detail below in the Examples section.

Exemplary media for culturing embryoid bodies or organoids include, but are not limited to, Aggrewell™ medium (AW) commercially available from StemCell Technologies, Inc., neural induction medium (NIM) comprising DMEM/F12 medium, supplemented with 1:100 N2 supplement, 1 μg/ml heparin sulfate, 1 mM glutamax, and MEM non-essential amino acids. The small molecule smad inhibitor SB431542 can be added to NIM at 10 nM concentration, and the protein noggin can be added to enhance neural specification. Cerebral organoids can be further differentiated in neural differentiation medium, phase 1 (NDM1) comprising a 1:1 mix of DMEM/F12 and Neurobasal medium supplemented with 1:200 N2 supplement, 1:100 B27 supplement without vitamin A, 3.5 μL/L of 2-mercaptoethanol, 1:4000 insulin, 1:100 glutamax, and 1:200 MEM-non essential amino acids. Further cerebral maturation may be achieved by culturing the organoids in Neural differentiation medium, phase 2 (NDM2) including, e.g., a 1:1 mix of DMEM/F12 and Neurobasal medium supplemented with 1:200 N2 supplement, 1:100 B27 supplement with vitamin A, 3.5 μL/L of 2-mercaptoethanol, 1:4000 insulin, 1:100 glutamax, and 1:200 MEM-non essential amino acids.

In certain embodiments, endothelial cells may be encouraged to undergo proliferation and specification to a brain microvascular phenotype by culturing the cells in brain microvascular endothelial cell (BMEC) medium including, e.g., endothelial serum-free medium supplemented with 20 ng/ml of FGF, 1% platelet-poor plasma-derived bovine serum, and 10 μM retinoic acid.

In certain embodiments, various biological agents or factors may be used in combination with the media. Exemplary biological agents or factors that may be used in the described method include, e.g., basic FGF, noggin, the small molecule TGF-beta inhibitor SB431542, Activin A, BMP-4, Wnt, epidermal growth factor (EGF), ascorbic acid, retinoic acid, bovine brain extract, heparin, hydrocortisone, gentamicin, fetal bovine serum, Insulin-like growth factor (IGF), and vascular endothelial growth factor (VEGF).

In certain embodiments, relating to synthesizing cerebral organoids, during the development, the cell aggregates can form polarized neuroepithelial structures and a neuroepithelial sheet, which will develop several round clusters (rosettes). These steps can be controlled by neural induction medium as described by Eiraku (2008), US 2011/0091869 A1 and WO 2011/055855 A1.

In the absence of neural induction medium, e.g., by using standard differentiation media, the method may include culturing in a three dimensional matrix, preferably a gel, especially a rigid stable gel. As such, in certain embodiments, the method also includes a step of culturing the cell aggregates in a three dimensional matrix, preferably a gel, which can result enhanced epithelial polarization and improved cortical layer formation. For example, further expansion of neuroepithelium and/or differentiation can be observed with embryoid bodies or organoids cultured in a three dimensional matrix.

A suitable three dimensional matrix may comprise collagen type 1 or matrigel. In certain embodiments, the three dimensional matrix comprises extracellular matrix from the Engelbreth-Holm-Swarm tumor or any component thereof such as laminin, collagen, preferably type 4 collagen, entactin, and optionally further heparan-sulfated proteoglycan or any combination thereof. Such a matrix is Matrigel. Matrigel was previously described in U.S. Pat. No. 4,829,000, which is incorporated by reference in its entirety.

In certain embodiments, the matrix comprises a concentration of at least 3.7 mg/ml containing in parts by weight about 60-85% laminin, 5-30% collagen IV, optionally 1-10% nidogen, optionally 1-10% heparan sulfate proteoglycan and 1-10% entactin. Matrigel's solid components usually comprise approximately 60% laminin, 30% collagen IV, and 8% entactin. Entactin is a bridging molecule that interacts with laminin and collagen. The three dimensional matrix may further comprise growth factors, such as any one of EGF (epidermal growth factor), FGF (fibroblast growth factor), NGF, PDGF, IGF (insulin-like growth factor), especially IGF-1, TGF-β, tissue plasminogen activator. The three dimensional matrix may also be free of any of these growth factors.

In certain embodiments, the three dimensional matrix may be a three dimensional structure of a biocompatible matrix. It may include collagen, gelatin, chitosan, hyaluronan, methylcellulose, laminin and/or alginate. The matrix may be a gel, in particular a hydrogel. Organo-chemical hydrogels may comprise polyvinyl alcohol, sodium polyacrylate, acrylate polymers and copolymers with an abundance of hydrophilic groups. Hydrogels comprise a network of polymer chains that are hydrophilic, sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content.

After the expansion, the cell aggregates can be cultured in suspension culture, preferably a bioreactor, such as a spinning bioreactor (FIG. 5A). The culturing in suspension culture is preferably also in the absence of neural induction medium. A suitable medium is a standard differentiation medium. "A spinning bioreactor" refers to a device or system meant to grow cells or tissues in the context of cell culture, as shown in FIG. 5A. These devices are being developed for use in tissue engineering or biochemical engineering. For example, a suitable spinning bioreactor can be purchased from Wheaton Inc., or a Rotary Cell Culture System can be purchased from Synthecon.

The cells in the bioreactors may be cultured in a proteinaceous matrix (such as Matrigel) that supports three-dimensional growth. FIGS. 5B and 5C show cerebral organoids at day 14 and day 22, respectively, developing in the spinning bioreactor.

FIGS. 7A-7I also show cerebral organoids developing in spinning bioreactors, scale bars=100 μm.

Figures 8A, 8B:
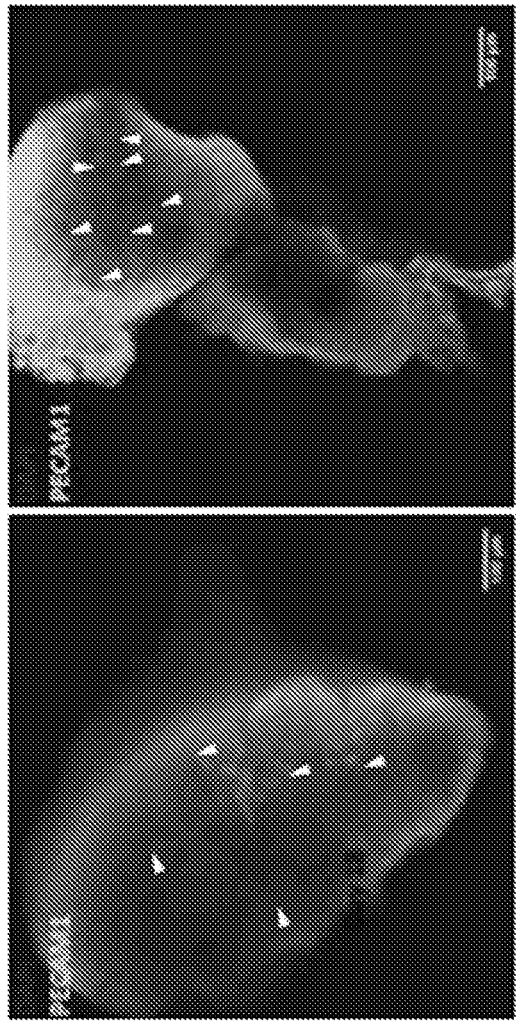
FIG. 8A depicts a photograph of a cultured cerebral organoid with internal plexus.
FIG. 8B depicts a photograph of a cultured cerebral organoid with internal plexus.

As shown in FIGS. 8A-8B, organoids cultured according to the described methods form an internal vascular plexus as visualized by a network of endothelial cells identified by an antibody stain for PECAM-1 (CD-31). The specific media conditions to produce the organoid of FIG. 8A include Aggrewell™ medium (3 days), neural induction medium (5 days), neural differentiation medium (phase 1; 5 days) and neural differentiation medium (phase 2; 5 days). The specific media conditions to produce the organoid of FIG. 8B include Aggrewell™ medium (3 days), brain microvascular endothelium medium (5 days), neural differentiation medium (phase 1; 5 days) and neural differentiation medium (phase 2; 5 days).

After a set period of time the organoids grow mature enough for study, or for implanting into a scaffold or biscaffold replete with 3D printed vasculature.

Importantly, prior to, during and/or after the implanting or embedding, the embryoid body or organoid is further differentiated using a combination of NIM, NDM1, EGM-2 or NDM2 media into a tissue containing at least one of pluripotent stem cells, multipotent stem cells, progenitor cells, terminally differentiated cells, endothelial cells, endothelial progenitor cells, immortalized cell lines, or primary cells.

In the embodiments described above, stem cells (e.g., iPSCs) are cultured to form a cell aggregate, the pluripotent stem cells can be induced to differentiate into a tissue (e.g., neural tissue) containing at least one of pluripotent stem cells, multipotent stem cells, progenitor cells, terminally differentiated cells, endothelial cells, endothelial progenitor cells, immortalized cell lines, or primary cells. For providing a multicellular aggregation, it is, e.g., possible to culture pluripotent stem cells from the multicellular aggregates. For example, FIG. 6 shows a schematic of the culture system used to develop organoids from iPSCs and exemplary images or organoids taken at each stage.

Figure 9:
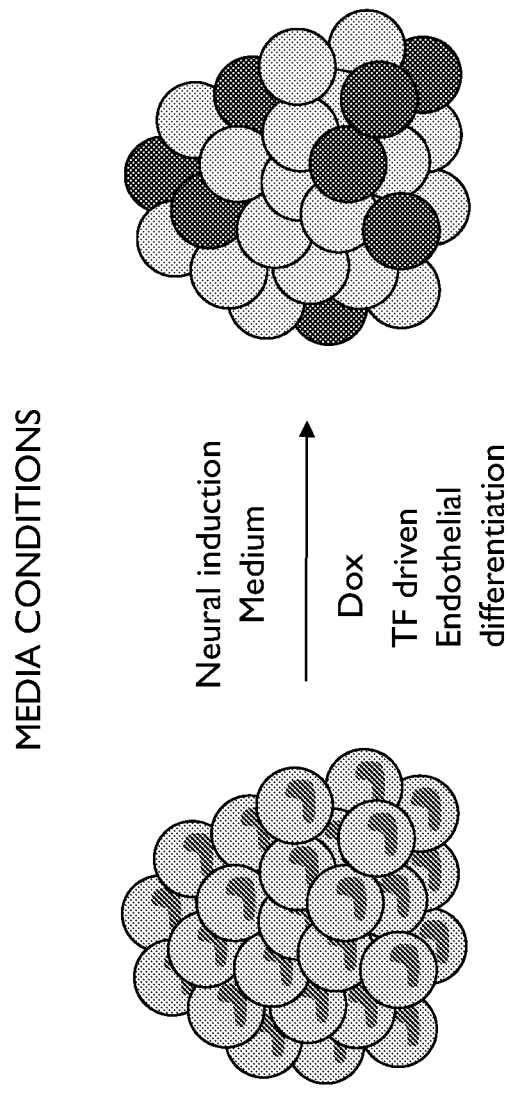
FIG. 9 depicts a schematic illustration of a method of producing a mixed population of wild-type and inducible cells.

In certain alternative embodiments, embryoid bodies or organoids comprising at least two different populations of organoid or embryoid body cells (i.e., a first population of embryoid body or organoid cells and a second population of the embryoid body or organoid cells) can be produced and later vascularized. For example, in certain embodiments, the embryoid body or organoid can comprise multiple populations of cells (i.e., at least two different cell lineages; FIG. 9), such as endothelial and neuronal, obtained by differentiation of iPSCs using the same culture condition.

Figure 10:
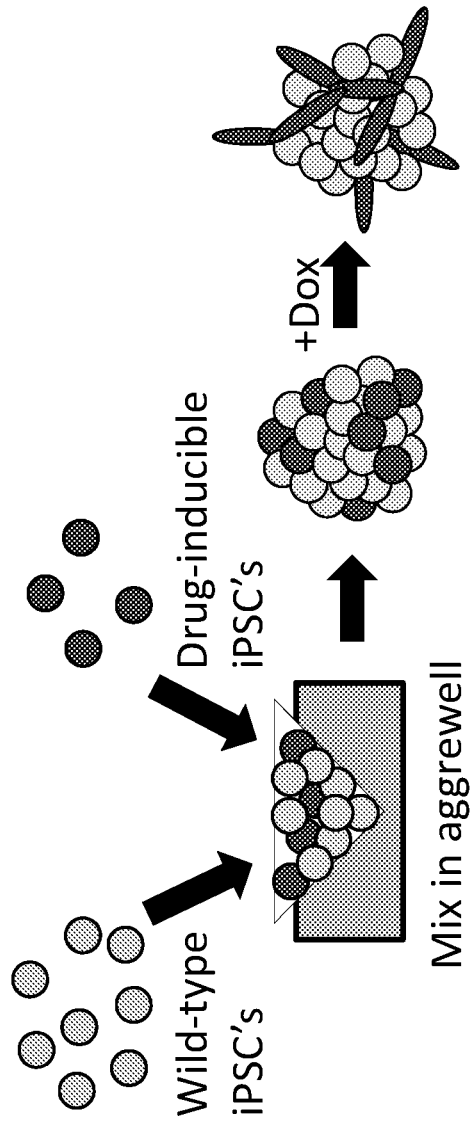
FIG. 10 depicts a schematic illustration of a method of producing a multi-population embryoid body or organoid.

As shown schematically in FIG. 10, the method of producing the multi-population embryoid body or organoid includes culturing a wild-type population of cells and a genetically-engineered inducible population of cells in a medium, inducing direct differentiation and/or transdifferentiation of the genetically-engineered inducible population of cells into the first population of the embryoid body or organoid cells, inducing differentiation of the wild-type population of cells into the second population of the embryoid body or organoid cells, and thereby forming the embryoid body or organoid comprising at least the first population of the embryoid body or organoid cells and the second population of the embryoid body or organoid cells.

The terms "direct differentiation" or "directed differentiation" refer to the culture of pluripotent or multipotent stem cells in a condition that preferentially encourages the differentiation of the stem cell to a specific, more differentiated state. For example, a pluripotent stem cell may be cultured in a condition that results in an enriched population of specific multipotent stem cells such as neural progenitor cells. Alternatively, a multipotent stem cell such as a neural stem cell may be directly differentiated into a more differentiated state such as a neuron, astrocyte or oligodendrocyte.

The term "transdifferentiation" refers to the conversion of one cell type that may be a multipotent or unipotent stem cell, or a terminally differentiated mature cell phenotype to a different cell type that may be a different multipotent or unipotent stem cell, or a terminally differentiated mature cell phenotype. For example, a neural stem cell, a radial glia, or a neuron may be transdifferentiated into an endothelial cell.

The genetically-engineered inducible population of cells may be created by introducing a DNA delivery element (as illustrated in FIG. 11) comprising at least one of constitutive promoter, small molecule inducible promoter, cell-autonomous promoter, cell non-autonomous promoter, selection marker, or a combination thereof.

Examples of constitutive promoters include, e.g., EF1alpha, PGK, Ubiquitin, and CMV. Examples of small molecule inducible promoters include, e.g. doxycycline or cumate inducible promoters. Examples of cell-autonomous promoters include, e.g., cell type-specific promoters, such as DCX. Examples of cell non-autonomous promoter include, e.g., heat induced and light induced promoters.

DNA delivery elements can be selected from lentiviral inverted repeats, packaging signal (e.g., pLIX403 vector), transposon integration elements (e.g., PiggyBac vector), episomal replication elements. Alternatively, transient expression by electroporation or lipofection can be used.

Selection markers may be selected from, e.g., drug resistance markers (e.g. puromycin, neomycin, and blasticidin). Alternatively, transient expression followed by dilution from cell division rather than selection markers may be used.

Examples of specific transcription factors that may be used to induce endothelial cells within any organoid (e.g. for vasculature) and to produce mixed populations within organoids include ETV2/ER71, FL11, ERG (Ginsberg et al. 2012 *Cell*), which induce differentiation of mature amniotic cells to endothelial cells; Gata2, FOXC1, FOXC2, HEY1, HEY2, SOX7, SOX18, PROX1 (Park et al. 2013 *Circulation Research*), which induce differentiation of stem cells into various subtypes of endothelial cells (e.g. venous, arterial, lymphatic); Brachyury/T, which may be used for possible mesoderm induction, required for primitive streak formation in vivo.

Examples of specific transcription factors that may be used to induce neurons within any organoid (e.g. autonomic nervous system control of internal organs) include NEUROG1/2 (Busskamp, et al., Molecular Systems Biology (2014)), which induce formation of excitatory neurons; ASCL1 (Chanda, et al., Stem Cell Reports (2014)), which induce formation of excitatory neurons; ASCL1, BRN2, MYT1L, LHX3, HB9, ISL1, NGN2 (Son et al. 2011 *Cell Stem Cell*), which induce formation of motor neurons; and ASCL1, MYT1L, KLF7 (Wainger, et al., Nature Neuroscience (2014)), which induce formation of pain receptor neurons.

The first population of the embryoid body or organoid cells can comprise pluripotent stem cells, multipotent stem cells, progenitor cells, terminally differentiated cells, endothelial cells, endothelial progenitor cells, immortalized cell lines, or primary cells.

The second population of the embryoid body or organoid cells comprises neural progenitor cells. The neural progenitor cells can form at least one of excitatory neurons, inhibitory interneurons, motor neurons, dopaminergic neurons, pain receptor neurons, astrocytes, oligodendrocyte progenitor cells, oligodendrocytes.

The step of inducing direct differentiation and/or transdifferentiation of the genetically-engineered inducible population of cells can comprise introducing at least one cue selected from the group consisting of transcription factors, drugs, small molecules, growth factors, morphogens, hormones, DNA, shRNA, siRNA, nanoparticles, mRNA, modified mRNA, heat, light, and mechanical stimulation.

In certain embodiments, the direct differentiation may be accompanied by a secondary induction of a different gene, e.g., a second orthogonal induction. This secondary induction may occur at an earlier time, simultaneously, or at a later time than the first gene induction. The secondary gene induction may be via providing at least one cue selected from the group consisting of transcription factors, drugs, small molecules, growth factors, morphogens, hormones, DNA, shRNA, siRNA, nanoparticles, mRNA, modified mRNA, heat, light, and mechanical stimulation.

In certain embodiments, the cue selected for the secondary gene induction is the same as the cue selected for the step of inducing direct differentiation and/or transdifferentiation of the genetically-engineered inducible population of cells. Alternatively, the cue selected for the secondary gene induction is different, and orthogonal, from the cue selected for the step of inducing direct differentiation and/or transdifferentiation of the genetically-engineered inducible population of cells.

In certain embodiment, the first population of the embryoid body or organoid cells can undergo a further development due to induction of a secondary gene. The induction of the secondary gene induces an expression of a constitutively-active PKC protein thereby enhancing at least one of a sprouting behavior of the first population of the embryoid body or organoid cells, or neurite outgrowth. The first population of the embryoid body or organoid cells may be endothelial cells.

The ratio of the first population the embryoid body or organoid cells to the second population of the embryoid body or organoid cells may be 1:1, 1:2, 1:3. 1:4, 1:5, etc. or 5:1. 4:1. 3:1, 2:1.

The step of culturing may be in a differentiation medium. In certain embodiments, the differentiation medium includes doxycycline (DOX) or another drug.

Importantly, the concept of inducing not only differentiation, but specific programmed cell behaviors by either adding a second gene that is induced by the same signal, or adding a second orthogonal induction cue like a different drug than doxycycline is described. The application would be to induce the expression of a constitutively-active PKC protein that dramatically enhances sprouting behavior of endothelial cells. PKC also encourages enhanced neurite outgrowth. It is important that the endogenous PKC signaling that directs neural outgrowth in cerebral organoids is not affected. Thus, by activating PKC in only the subset, sprouting in the endothelial cells is specifically achieved.

Once, or before, the embryoid bodies or organoids grows to a size at which it becomes oxygen or nutrient limited—typically once it reaches approximately 1 mm in diameter, (1-22 days) and having the desired characteristics described above, the embryoid body or organoid is implanted or embedded into a scaffold or biscaffold replete with 3D printed vasculature.

Figure 13:
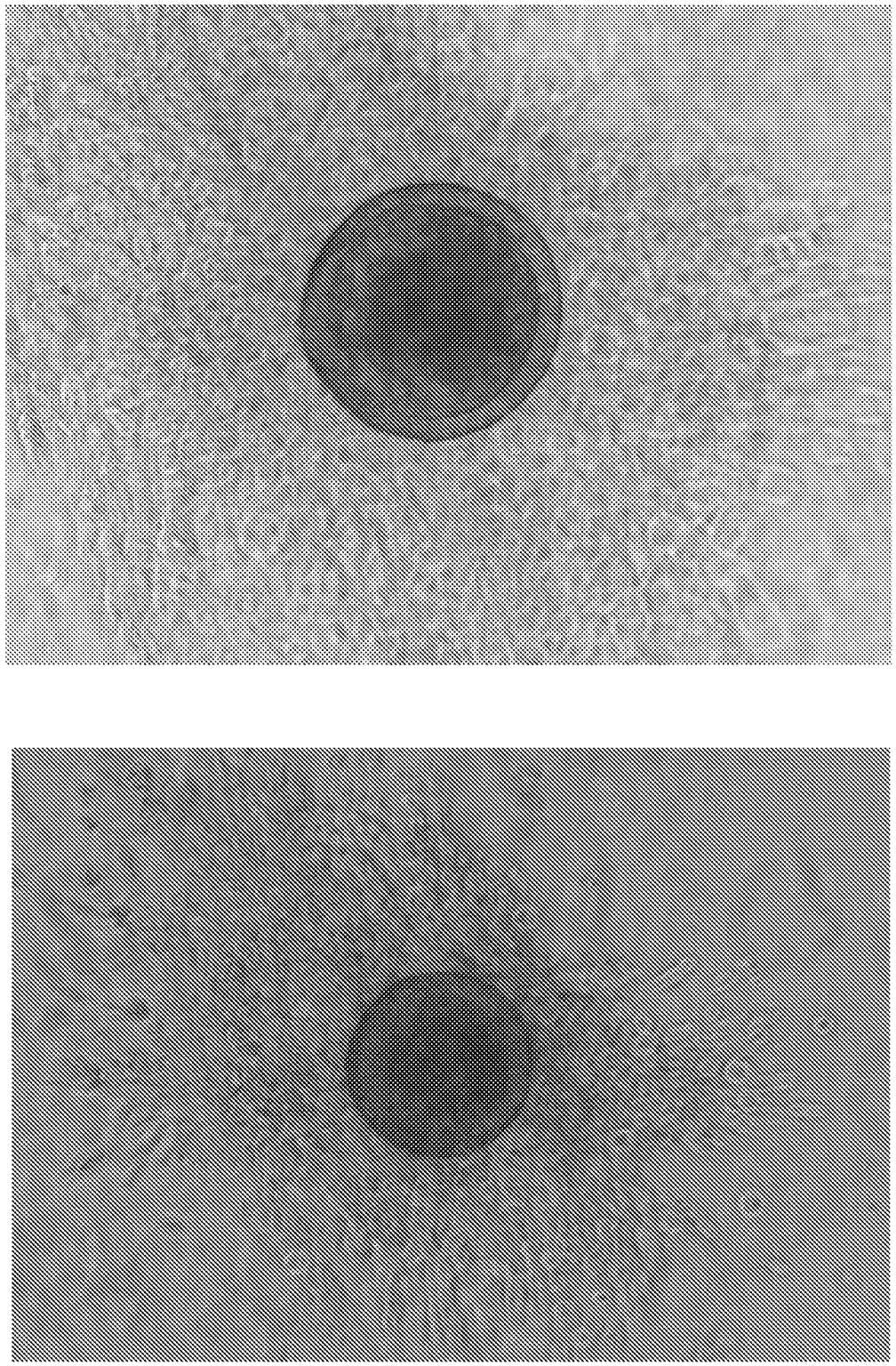
FIG. 13 depicts vascular spheres derived from embryoid bodies undergoing sprouting.

In certain embodiments, as shown in FIG. 13, embedding embryoid bodies or organoids in, e.g., collagen (e.g., collagen I) encourages vascular sprouting (from vascular spheres).

Figure 12:
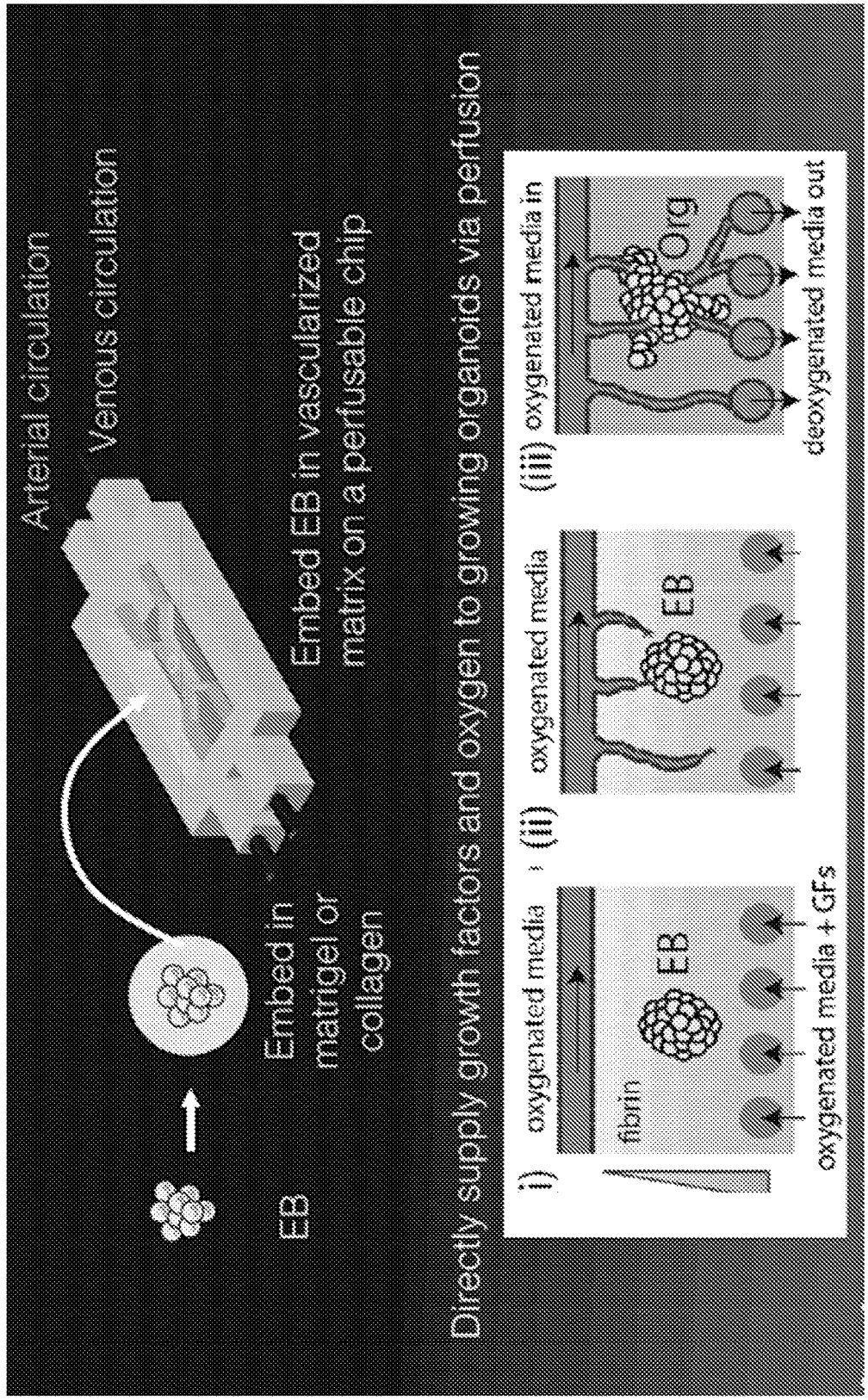
FIG. 12 depicts a schematic illustration of a strategy for creating perfusable vascularized organoids.

FIG. 12 schematically shows steps where the embryoid body is embedded in a matrigel or collagen and then embedded into vascularized matrix on a perfusable chip for arterial and venous circulation.

Vascularized tissue constructs and methods of producing vascular channels in the extracellular matrix composition using 3D printed technology was previously described in WO2015/069619, which is incorporated herein by reference in its entirety.

For example, vascular channels may be created by depositing one or more sacrificial filaments, each comprising a fugitive ink and/or a plurality of viable cells on the substrate to form a vascular pattern. The vascular pattern can be partially or fully surrounded by an extracellular matrix composition. The fugitive ink is then removed to create a network of vascular channels in the extracellular matrix composition (FIGS. 14A-G).

Advantageously, the composition may be designed to support the attachment and proliferation of endothelial cells, which line vascular channels providing a barrier to fluid diffusion, while simultaneously facilitating homeostatic functions and helping establish vascular niches specific to the various tissues. To promote endothelialization, in some embodiments the sacrificial filament(s) comprising the fugitive ink may further include a plurality of endothelial cells or other viable cells. The cells may be deposited along with the sacrificial filament and may remain in the vascular channels after removal of the fugitive ink, as illustrated in FIGS. 14A-14C. Direct cellularization of the channels can be achieved if the cells adsorb to the channel walls after liquidation of the fugitive ink. This approach may allow one to incorporate viable cells into highly tortuous networks or small channels that may be difficult to infill using direct injection due to an increased resistance to flow. An exemplary printed tissue construct including a channel formed by evacuation of a fugitive ink comprising endothelial cells and Pluronic F127 is shown in FIGS. 14D-14G, and is was previously described in the WO 2015/069619.

Specifically, one or more sacrificial filaments comprising a fugitive ink and or a plurality of endothelial cells or other viable cells may be deposited on a substrate to form a vascular pattern. The vascular pattern comprises a two- or three-dimensional interconnected arrangement or network of the one or more sacrificial filaments. Removal of the fugitive ink after partial or complete encapsulation with the extracellular matrix composition creates a perfusable network of vascular channels. Because the sacrificial filaments may be deposited in a 3D printing process that involves extrusion through a micronozzle, it may be advantageous for the fugitive ink to: (1) exhibit shear thinning behavior; (2) exhibit a defined yield stress $T_y$; and/or (3) have a shear elastic modulus G' and a shear viscous modulus G" modulus where G'>G" at room temperature.

The substrate for deposition typically comprises a material such as glass or other ceramics, PDMS, acrylic, polyurethane, polystyrene or other polymers. In some embodiments, the substrate may comprise living tissue or dehydrated tissue, or one of the extracellular matrix compositions described above. The substrate may be cleaned and surface treated prior to printing. For example, glass substrates may undergo a silane treatment to promote bonding of the cell-laden filaments to the glass substrate. In some embodiments, it is envisioned that the substrate may not be a solid-phase material but may instead be in the liquid or gel phase and may have carefully controlled rheological properties, as described, for example, in W. Wu et al., *Adv. Mater.* 23 (2011) H178-H183, which is hereby incorporated by reference. In the work of Wu et al., a fugitive ink was printed directly into synthetic hydrogels to create network structures. However, these synthetic materials do not support cell attachment and proliferation, limiting their use to non-biological applications. In the present disclosure, an extracellular matrix composition that facilitates cell attachment, migration, proliferation, and tissue-specific function while maintaining the appropriate rheology for printing is described. The sacrificial filaments are embedded in the extracellular matrix composition during printing, and thus the at least partial surrounding of the vascular patterns with the extracellular matrix composition occurs during deposition of each of the sacrificial filaments. This includes arbitrarily complex 3D structures that may require support material during printing. When the forming and embedding of the vascular patterns occurs simultaneously, the substrate onto which deposition occurs may be considered to be the container that holds the extracellular matrix composition or the extracellular matrix composition itself.

To form the extracellular matrix composition, a microgel (e.g., a poly(acrylic acid) (PAA) microgel) may be used as a rheological modifier and blended with one or more extracellular matrix materials, as set forth previously, such as gelatin methacrylate. A semi-interpenetrating polymer network (semi-IPN) may be formed. Microgels may be understood to comprise colloidal gel particles that are composed of chemically cross-linked three-dimensional polymer networks. Microgels may act as sterically stabilized colloids with only a shell and no core. They can vary in composition and may include PAA, polystyrenes, PEG, and/or other biomaterials. It is contemplated that a natural extracellular matrix or biomaterial may be converted into a microgel form to impart the ideal rheology. Examples of suitable biomaterials include hyaluron, collagen, alginate, fibrin, albumin, fibronectin, elastin, or matrigel. Alternatively, synthetic materials such as PEG, acrylates, urethanes, or silicones may be modified in a similar manner.

Representative rheological measurements of ink and matrix rheology that are appropriate for embedded printing were previously described in WO 2015/069619. In one example, a high molecular weight (>1.25 MDa) PAA microgel may be used as a rheological modifier and blended with gelatin-methacrylate (GelMa) to create an extracellular matrix composition that supports the creation of complex 3D vascular networks, which, in certain embodiments may be endothelialized as described in WO 2015/069619. The transparency of the extracellular matrix composition may be altered by varying the degree of substitution and mesh size.

The method may further include, prior to surrounding or encapsulating the vascular patterns with the extracellular matrix composition, depositing one or more structural filaments layer by layer on the substrate in a predetermined pattern to form a mold. The structural filaments may comprise one or more structural materials selected from among the exemplary extracellular matrix compositions or extracellular matrix materials provided above. The mold may hold the extracellular matrix composition during the encapsulation and may remain as part of the tissue construct, or it may be removed after processing. The structural filaments may define the perimeter of the tissue construct on the substrate and all or at least a portion of the three-dimensional shape of the tissue construct out of the XY plane.

Figure 15:
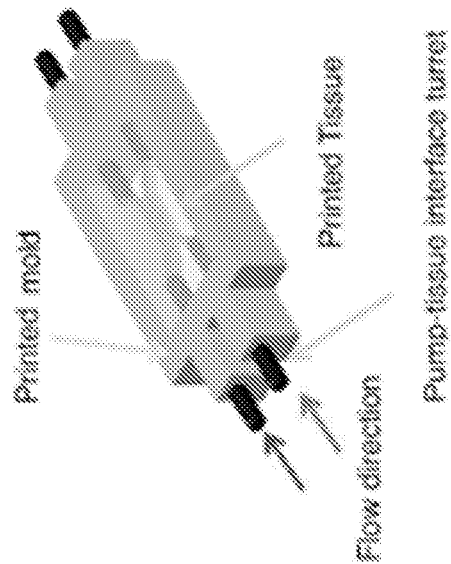
FIG. 15 shows an exemplary design of a printed mold or an interface structure.

The mold may also have other functionalities besides defining the shape of the construct. For example, the mold may serve as an interface for perfusion of channels in a printed tissue construct. FIG. 15 shows an exemplary design of a printed mold or an interface structure. The mold, which may also be referred to as an interface structure, can hold vascularized tissue in place during rocking by immobilizing the tissue construct between a base portion of the mold, which may comprise PDMS, and an overlying cover, which may comprise glass.

The mold designs of FIG. 15 enables active pump-based perfusion and include flow channels that are in fluid communication with (e.g., contiguous with) the vascular channels. Conduits that serve as flow channels may be partially or fully embedded in the mold itself and hollow tubes (e.g., metal tubes) may be used to interface with the vascular channels. The exemplary mold shown in FIG. 15 has a wall with multiple buttresses that contain the flow channels, which include hollow pins extending into the interior of the mold, where the tissue construct is fabricated. The vascular channels of the tissue construct may be contiguous with apertures of the hollow pins to enable flow to be introduced into the vascular channels from tubing connected to the flow channels, and fluid may be removed from the vascular channels through one or more other apertures.

In one example, the mold may be formed of an elastomeric silicone, a structural material known to be viscoelastic, non-toxic, biocompatible, and capable of forming reversible press-to-fit seals. The structural material may be 3D printed to form one or more uncured structural filaments comprising one or more of silicone, epoxies, esters of acrylic acid, or one of the extracellular matrix compositions provided above. After printing is complete, the structural filament(s) may be cured (e.g. by heating or photopolymerizing) for a suitable time duration (e.g., about one hour or more), after which the mold may exhibit the desired material properties.

The encapsulation of the vascular patterns may comprise casting a liquified matrix precursor into the mold and gelling the matrix precursor to form the extracellular matrix composition. Casting of the matrix precursor may take place at a temperature of from about 25° C. to about 40° C. For example, gelatin methacrylate, or GelMA, may be cast at a temperature of about 37° C. After casting, the matrix precursor may be cooled (e.g., to about 15° C. in the case of GelMA) to form a rigid physical gel. Alternatively, the encapsulation may occur during deposition of the vascular patterns in an embedded or omni-directional 3D printing process, as indicated above. It is also contemplated that the extracellular matrix composition may be deposited by filament deposition, similar to the sacrificial filaments. For example, one or more ECM filaments comprising the extracellular matrix composition may be extruded from a nozzle and deposited on the substrate layer by layer to build up the desired 3D geometry. In such a case, it may not be necessary to employ a mold to contain the extracellular matrix composition.

The extracellular matrix composition may be cured before or after removal of the fugitive ink to form a permanently chemically cross-linked structure. Depending on the extracellular matrix composition, the curing may entail heating, UV radiation or chemical additives (e.g., enzymatic curing).

Any or all of the filaments deposited on the substrate—including the one or more sacrificial filaments defining the interpenetrating vascular pattern or a functional channel pattern, the one or more structural filaments that may define the mold, and/or the one or more ECM filaments that may yield the extracellular matrix composition—may be extruded from a nozzle before being deposited on the substrate. The extrusion process was previously described in WO 2015/069619, which is incorporated herein in its entirety.

The vascular network may be a two- or three-dimensional interconnected arrangement of vascular channels. The network may include one or more -furcations (e.g., bifurcations, trifurcations, etc.) from a parent vascular channel to a plurality of branching vascular channels. The network may have a hierarchical branching structure, where larger diameter channels branch into smaller diameter channels. Some or all of the vascular channels may follow a curved path, and thus may be considered to be curvilinear. All of the vascular channels in the network may have the same diameter, or at least one, some, or all of the vascular channels may have a different diameter. In some cases, one or more of the vascular channels may have a nonuniform diameter along a length thereof.

Figure 16:
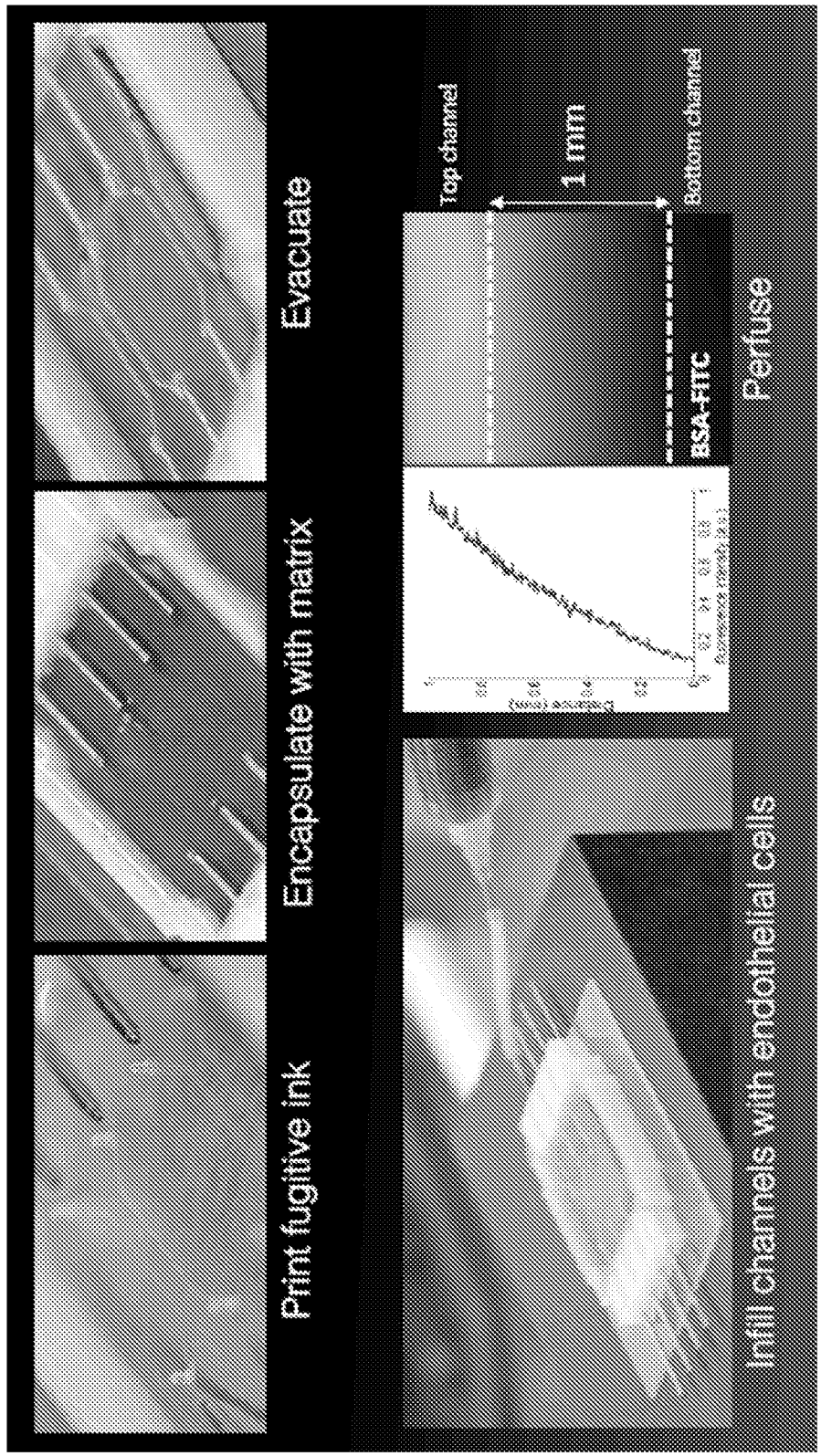
FIG. 16 shows an exemplary 3D printing method of custom perfusion chips.

FIG. 16 shows exemplary 3D printing method of custom perfusion chips.

Figure 17:
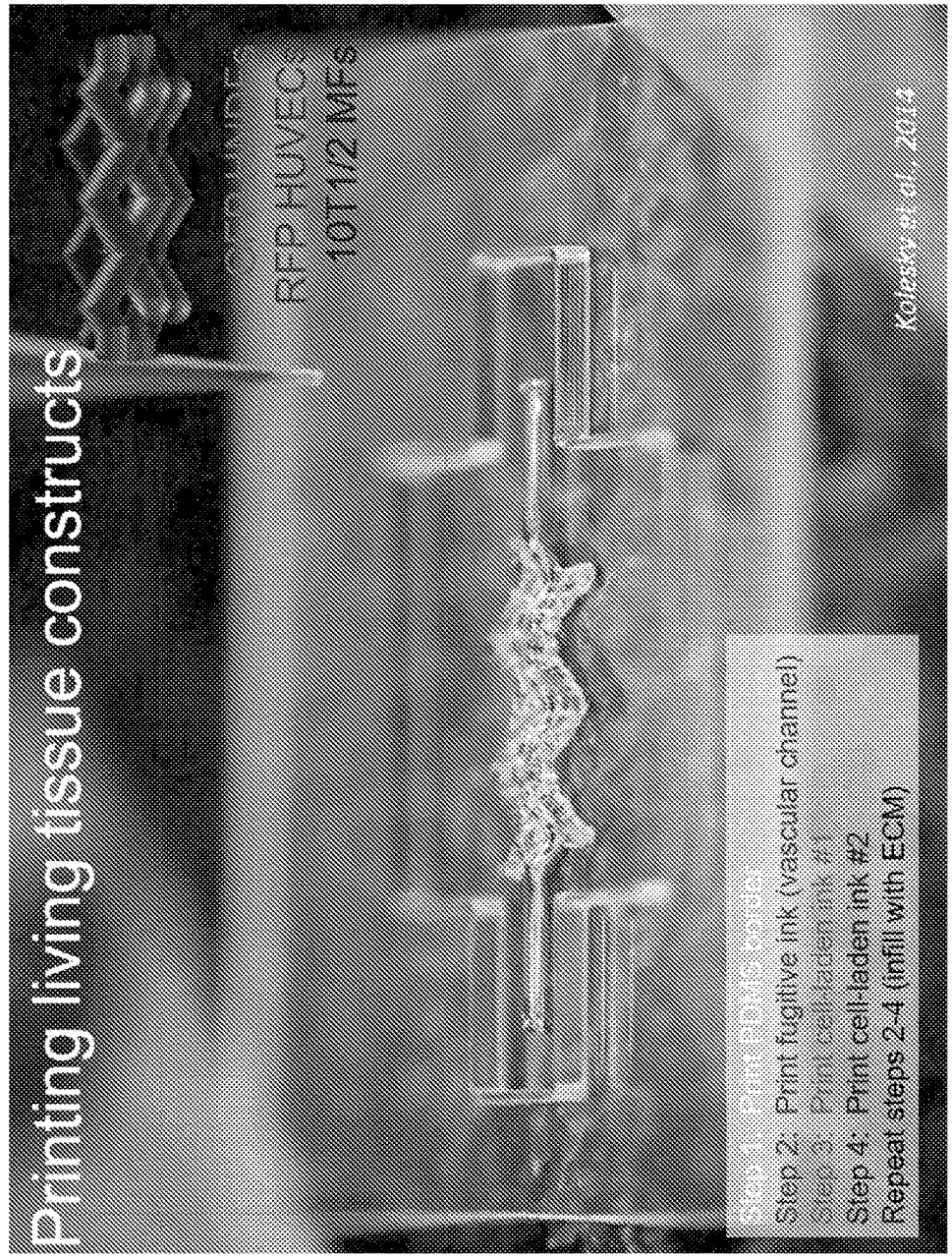
FIG. 17 shows printing of vascular tissues.
Figure 18:
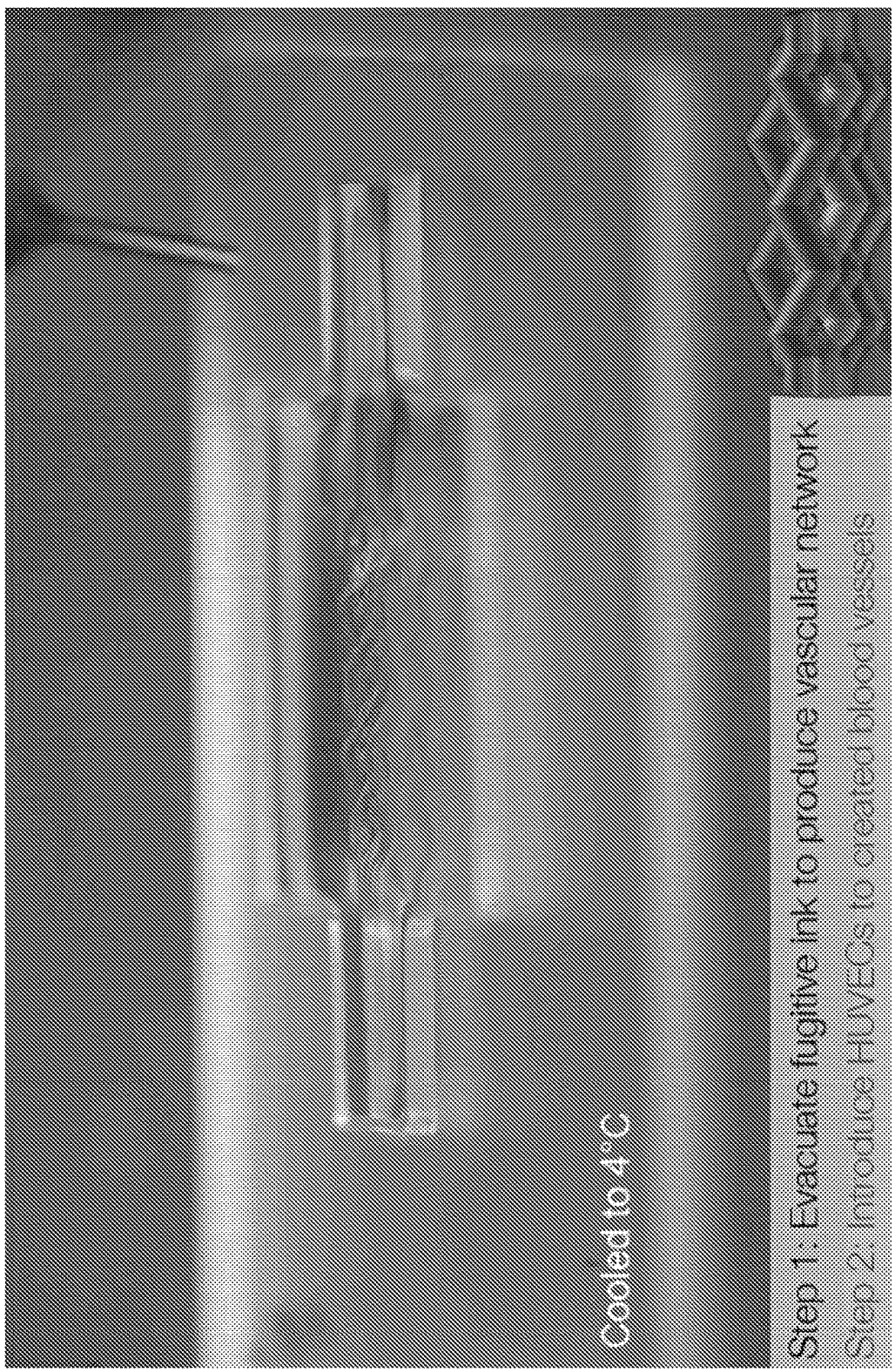
FIG. 18 shows printing of vascularized tissues.

Printing of vascularized tissues is shown in FIG. 17. In the shown embodiment, the PDMS border is printed first, followed by depositing filament comprising fugitive ink to create vascular channels. The next step includes depositing a first cell-laden ink and a second cell-laden ink. The step may be repeated 2-4 times followed by infilling with the ECM. Next, as shown in FIG. 18, the matrix is cooled (about 4° C.) to evacuate fugitive ink to produce a vascular network. Human umbilical vascular endothelial cells (HUVECs) may then be introduced to create blood vessels.

Figure 19:
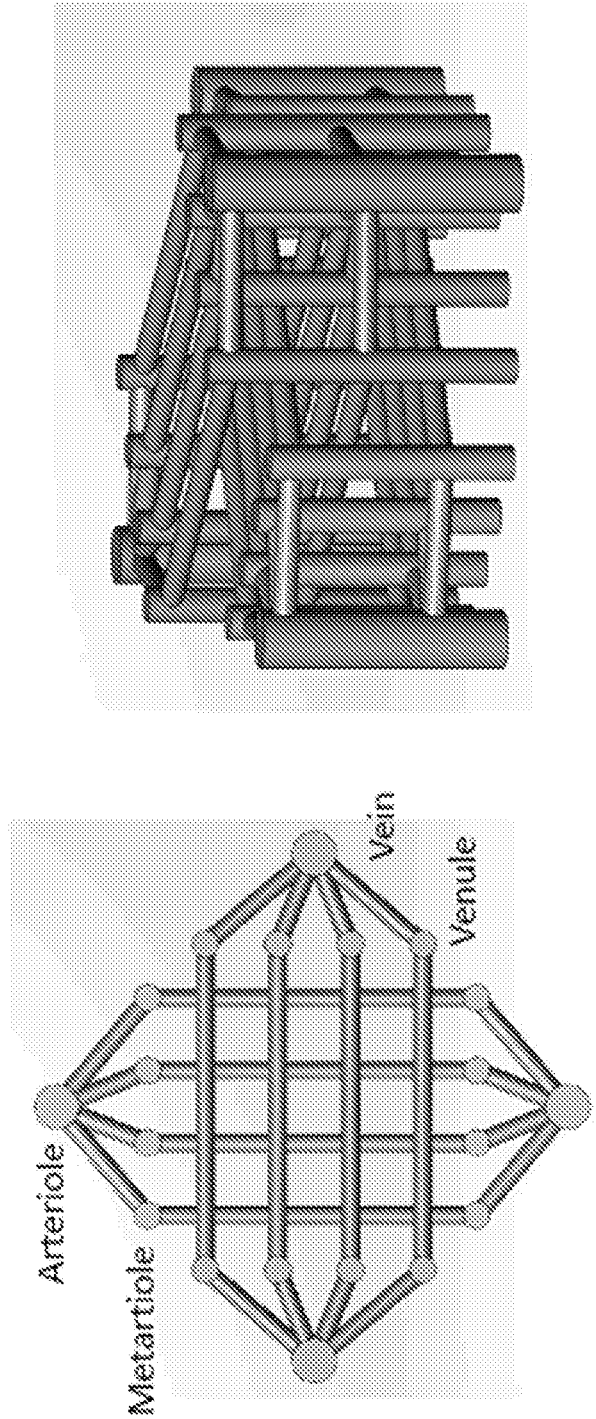
FIG. 19 depicts two, spanning, non-intersecting branched vascular networks (i.e., artero-venous plexus) created to enable natural capillary development to connect arterial and venous networks.

In certain embodiments, as shown in FIG. 19, two, spanning, non-intersecting branched vascular networks (i.e., artero-venous plexus) are created to enable natural capillary development to connect arterial and venous networks.

Figure 20A:
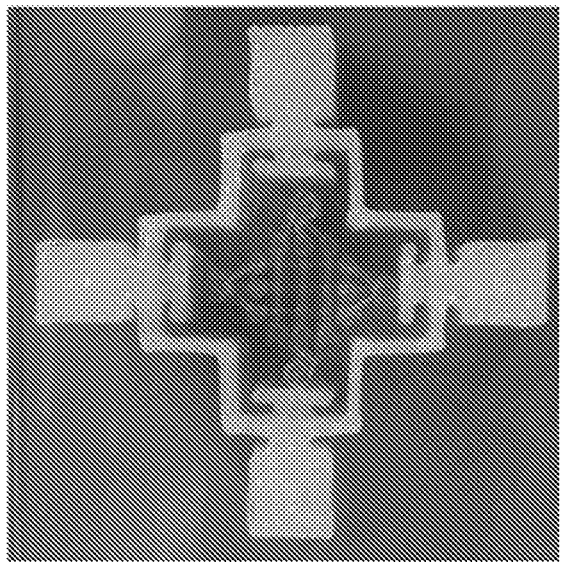
FIG. 20A depicts a top-view of printed artero-venous networks of Pluronic F-127 sacrificial filaments that can be used to generate an arterio-venous plexus after casting in a gel, cooling and removing the liquefied sacrificial Pluronic F-127.
Figure 20B:
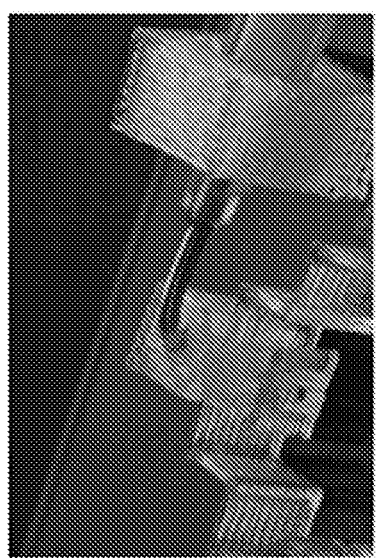
FIG. 20B shows the Pluronic-F127 structure of FIG. 20A printed inside a printed silicone perfusion chip.
Figure 20C:
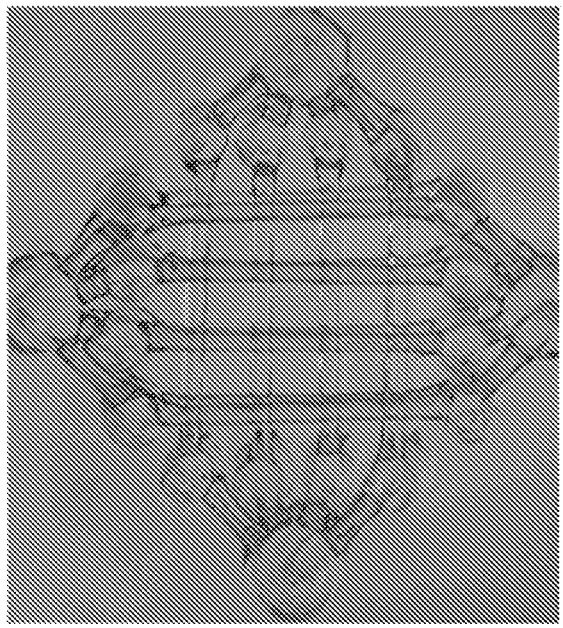
FIG. 20C shows how luer connectors can connect to the silicone chip to enable connection to an external pump.
Figure 20D:
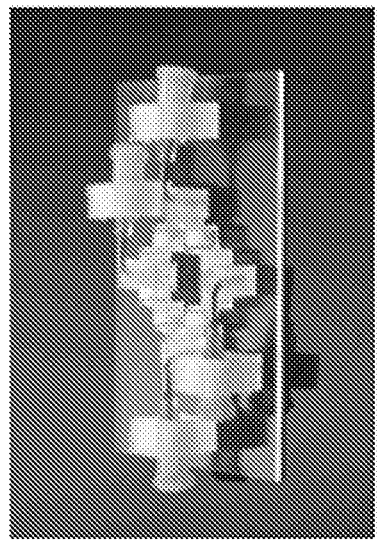
FIG. 20D shows how luer connectors can connect to the silicone chip to enable connection to an external pump.

FIGS. 20A-20D show examples of a 3D printed interface device for perfusing organoid bodies or organoids. Specifically, FIG. 20A shows a top-view of printed networks of Pluronic F-127 sacrificial filaments that can be used to generate an arterio-venous plexus after casting in a gel, cooling and removing the liquefied sacrificial Pluronic F-127. In this architecture, there are two independent networks that intertwine without contacting each other, as illustrated in FIG. 19. In this manner, a space a can be filled with two independent channel networks, an arterial, and a venous plexus; FIG. 20B shows the Pluronic-F127 structure of FIG. 20A printed inside a printed silicone perfusion chip. This chip facilitates the casting of the gel that surrounds the sacrificial filaments, the removal of the sacrificial material, and the subsequent active perfusion of the two independent channel networks; FIG. 20C and FIG. 20D show how luer connectors can connect to the silicone chip to enable connection to an external pump.

Figure 21:
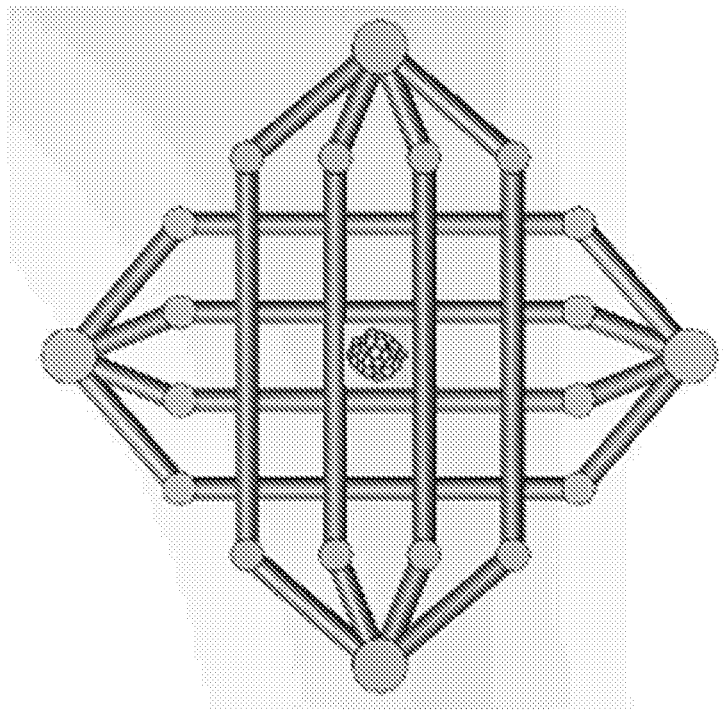
FIG. 21 depicts a schematic illustration of introducing the embryoid body into the 3D printed vascular network.

Once the embryoid body or organoid and the vascularized matrix comprising two, spanning, non-intersecting branched vascular networks (i.e., a first vascular network and a second vascular network, each vascular network vascular network comprising one or more interconnected vascular channels) are prepared as described in detail above, an embryoid body or organoid is embedded or implanted into the vascularized matrix (FIG. 21). The one or more interconnected vascular channels are formed by a manufacturing process or by a biological developmental process that may include at least one of vasculogenesis, angiogenesis, or tubulogenesis, as described above.

The embryoid body or organoid may be introduced by casting a gel around a column of pluronic, removing the pluronic to generate a microwell, and placement of an embryoid body or organoid into the microwell. FIGS. 22A-D show embedding embryoid bodies into vascularized tissues. Specifically, FIGS. 22A-C show the embryoid bodies on day 2, day 3 and day 5, respectively, following the implantation. The red cells are HUVECs that line the printed vascular channels. Two independent vascular channels surround the central embryoid body or organoid (green) to provide nutrients and oxygen, and remove waste products. FIG. 22D shows an exemplary perfusion chip that is connected to an external for implanting and perfusing the sprouting organoid.

In certain embodiments, prior to embedding the embryoid body or organoid in the vascularized matrix, the embryoid body or organoid may be encapsulated in an extracellular matrix material, as described above. Preferably, the extracellular matrix material may comprise a gel. Additional examples of matrices that may be used for encapsulating the embryoid body or organoid include, but are not limited to, at least one of collagen I, fibrin, matrigel, gelatin, gelatin methacrylate, laminin, carbopol, NIPAM, PEG, PHEMA, silk, hyaluronic acid, or combinations thereof.

Alternatively, in certain other embodiments, the embryoid body or organoid is not encapsulated in an extracellular matrix material prior to embedding it in the vascularized matrix.

In certain embodiments, the embryoid body or organoid is embedded in a vascularized matrix by depositing the embryoid body or organoid embedded in matrigel or collagen into a vascularized matrix on a perfusable chip. As described above, the perfusable chip includes outlets to provide arterial and venous circulation. A strategy for creating perfusable vascularized organoids is schematically shown in FIG. 12.

Figure 23:
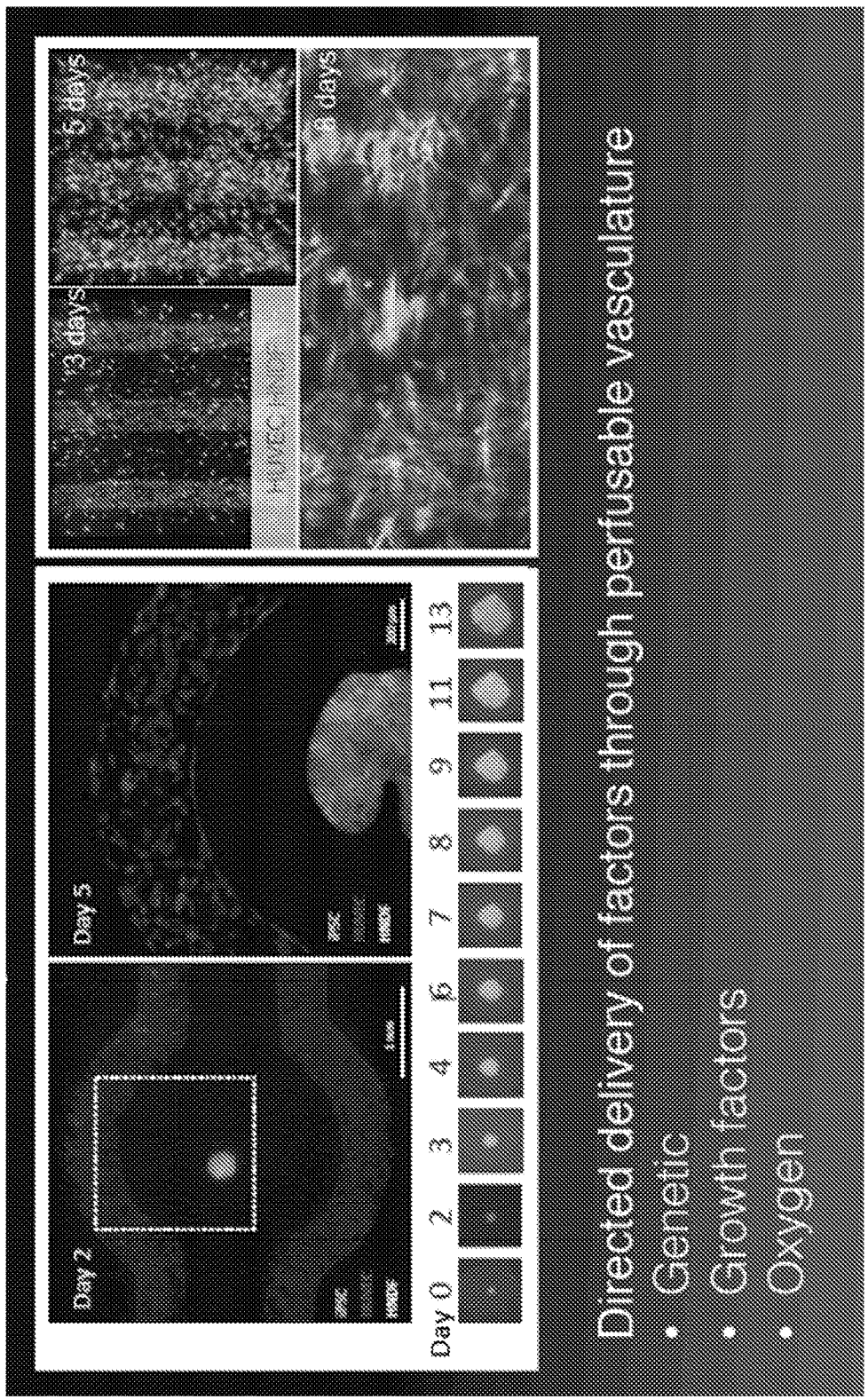
FIG. 23 depicts a strategy for promoting organoid and vascular development and delivery of factors.

The embryoid body or organoid is then exposed to one or more biological agents or factors, a biological agent gradient, a pressure, and/or an oxygen tension gradient, thereby inducing angiogenesis of capillary vessels to and/or from the embryoid body or organoid (FIG. 23). The supporting fibroblasts and organoids or embryoid bodies are shown in green and can be seen as growing due to the perfused nutrients through the surrounding channels; and the HUVECs are shown in red.

For example, one or more biological agents, a biological agent gradient, a pressure, and/or an oxygen tension gradient encourages the vascular plexus internal to the embryoid body or organoid to sprout away from the developing embryoid body or organoid by means of growth factors introduced to the 3D printed embryoid body or organoid. Also, the one or more biological agents, the biological agent gradient, the pressure, and/or the oxygen tension gradient further direct development, differentiation, and/or functioning of the embryoid body or organoid.

In certain embodiments, growth factors and oxygen may be directly supplied to grow embryoid bodies or organoids via perfusion using the perfusable chip (FIGS. 20A-D). Some examples of growth factors that encourage connection of vasculature include, but are not limited to, vascular endothelial growth factor (VEGF), basic fibroblast growth factor (bFGF), sphingosine-1-phosphate (S1P), phorbol myristate acetate (PMA), hepatocyte growth factor (HGF), monocyte chemotactic protein-1 (MCP-1), the angiopoietin ANG-1, the angiopoietin ANG-2, transforming growth factor beta (TGF-β), epidermal growth factor (EGF), human growth factor, matrix metalloproteinases (MMP's), and histamine.

In certain embodiments, the embryoid body or organoid is exposed to the one or more biological agents and/or the biological agent gradient due to diffusion of the one or more biological agents within the vascularized matrix. Alternatively, the embryoid body or organoid is exposed to the one or more biological agents and/or the biological agent gradient by localized deposition of materials loaded with the one or more biological agents within the tissue construct.

Alternatively, the embryoid body or organoid is exposed to the one or more biological agents and/or the biological agent gradient by localized de-novo production of growth factors by localized protein translation. Alternatively, the embryoid body or organoid is exposed to the one or more biological agents and/or the biological agent gradient via perfusion of one or both of the first and second vascular networks with the one or more biological agents.

In certain embodiments, only one of the first and second vascular networks is perfused with the one or more biological agents.

In certain other embodiments, both the first and second vascular networks are perfused with the one or more biological agents, wherein a biological agent concentration in the first vascular network is different than a biological agent concentration in the second vascular network.

In certain alternative embodiments, both the first and second vascular networks are perfused with the one or more biological agents, wherein a biological agent concentration in the first vascular network is the same as a biological agent concentration in the second vascular network.

The one or more biological agents can include, but are not limited to, one or more of the following: growth factors, morphogens, small molecules, drugs, hormones, DNA, shRNA, siRNA, nanoparticles, mRNA, modified mRNA.

Also, the biological agents can include one or more of the following growth factors: vascular endothelial growth factor (VEGF), basic fibroblast growth factor (bFGF), sphingosine-1-phosphate (S1P), phorbol myristate acetate (PMA), hepatocyte growth factor (HGF), monocyte chemotactic protein-1 (MCP-1), the angiopoietin ANG-1, the angiopoietin ANG-2, transforming growth factor beta (TGF-β), epidermal growth factor (EGF), human growth factor, matrix metalloproteinases (MMP's), and histamine.

In certain embodiments, an oxygen partial pressure gradient is introduced to one or both of the first and second vascular networks during perfusion. The oxygen partial pressure gradient may be formed by introducing deoxygenated media into one of the first and second vascular networks, and by introducing oxygenated media into the other of the first and second vascular networks. In certain embodiments, the perfusion may be carried out at a flow rate of from about 1 microliter per minute to about 1 liter per minute. In certain embodiments, one or both of the first and second vascular networks may be subjected to a transmural pressure during the perfusion.

In certain embodiments, following the exposure of the embryoid body or organoid to one or more biological agents, the biological agent gradient, the pressure, and/or the oxygen tension gradient, the capillary vessels connect the first vascular network to the second vascular network, thereby creating a single vascular network and a perfusable tissue structure. In certain embodiments, the single vascular network comprises an interpenetrating vascular network and/or a branched interpenetrating vascular network. Preferably, the single vascular network comprises interconnected arterial and venous channels.

In certain embodiments, the first vascular network and the second vascular network are independently addressable. In certain other embodiments, the first vascular network and the second vascular network are not in contact with each other.

In certain embodiments, the first vascular network comprises an arterial plexus and the second vascular network comprises a venous plexus.

In certain further embodiments, embedding the embryoid body or organoid in the vascularized matrix comprises depositing one or more cell-laden filaments each comprising a plurality of viable cells on a substrate to form one or more tissue patterns, each of the tissue patterns comprising one or more predetermined cell types, depositing one or more sacrificial filaments on the substrate to form a vascular pattern interpenetrating the one or more tissue patterns, each of the sacrificial filaments comprising a fugitive ink, depositing the embryoid body or organoid within the vascular pattern, at least partially surrounding the one or more tissue patterns and the vascular pattern with an extracellular matrix composition, and removing the fugitive ink, thereby forming the tissue construct comprising the embryoid body or organoid embedded therein. At least some portion of the one or more cell-laden filaments may comprise the one or more biological agents. One or both of the first and second vascular networks may comprise microfluidic channels.

In certain embodiments, a plurality of the embryoid bodies or organoids is embedded in the vascularized matrix. The embryoid bodies or organoids may comprise different phenotypes or may comprise the same phenotype.

In certain embodiments, embedding the embryoid body or organoid in the vascularized matrix may also comprise embedding the embryoid body or organoid in an array of the vascularized matrices, wherein the embedding, exposing and vascularizing is carried out in each vascularized matrix.

As described above, the vascular plexus internal to the embryoid body or organoid is encouraged to sprout away from the developing embryoid body or organoid by means of, e.g., growth factors introduced to the 3D printed embryoid body or organoid. After the sprouting plexus reaches the 3D printed vessels, the embryoid body or organoid may be perfused by use of a peristaltic pump and perfusion device as outlined in the International Publication No. WO 2015/069619. FIGS. 20A-20D and 20E-20G show exemplary designs of printed molds or interface structures. The exemplary mold shown in FIG. 15 is designed for passive rocking perfusion. The mold, which may also be referred to as an interface structure, can hold vascularized tissue in place during rocking by immobilizing the tissue construct between a base portion of the mold, which may comprise PDMS, and an overlying cover, which may comprise glass.

In certain embodiments, the mold designs enable active pump-based perfusion of a tissue construct and include flow channels that are in fluid communication with (e.g., contiguous with) the vascular channels of the tissue construct. Conduits that serve as flow channels may be partially or fully embedded in the mold itself and hollow pins (e.g., metal pins) may be used to interface with the vascular channels. The exemplary mold shown in FIG. 15 has a wall with multiple buttresses that contain the flow channels, which include hollow pins extending into the interior of the mold, where the tissue construct is fabricated. The vascular channels of the tissue construct may be contiguous with apertures of the hollow pins to enable flow to be introduced into the vascular channels from tubing connected to the flow channels, and fluid may be removed from the vascular channels through one or more other apertures.

In an additional aspect, the invention provides a method of investigating a developmental neurological tissue effect, e.g. a defect, in particular a developmental defect, comprising decreasing or increasing the expression in a gene of interest in a cell at any stage during the described method.

Certain further embodiments relate to a method of screening a candidate therapeutic agent suitable for treating a developmental neurological tissue defect of interest. According to this aspect, a candidate therapeutic drug can be screened for having an effect on any cell with a mutation, which can be introduced as described above. It is of course also possible to use cells of patients with a given mutation, inducing pluripotent stem cell status and performing the inventive methods to induce tissue development as described above.

Of course, it is also possible to screen candidate drugs, e.g. candidate therapeutic drugs, to have any effect on normal tissue as well, without a mutation, which leads to an aberrant development. Thus in yet another aspect, the invention relates to a method of testing a candidate drug for neurological effects, comprising administering a candidate drug to an artificial culture and determining an activity of interest of the cells of said culture and comparing said activity to an activity of cells to the culture without administering said candidate drug, wherein a differential activity indicates a neurological effect. Any kind of activity of the inventive cells or tissue, including metabolic turn-over or neuronal signaling can be searched for in a candidate drug. In essence, the inventive highly differentiated tissue can be used as a model for cerebral behavior testing on any effects of any drug. Such a method might also be used to test therapeutic drugs, intended for treating any kind of diseases, for having side-effects on nerves, in particular brain tissue, as can be observed in the inventive tissue culture.

Certain further embodiments relate to methods to obtain neuronal cells. In particular, the invention provides a method of obtaining a differentiated neural cell comprising the step of providing an artificial culture and isolating a differentiated neural cell of interest, or comprising the step of generating an artificial tissue culture according to the invention further comprising the step of isolating a differentiated neural cell of interest. Such cells isolated from the inventive culture or tissue have the benefit of representing similar morphological properties as cells isolated from cerebral tissue of an non-human animal, as mentioned above, or a human.

Certain additional embodiments relate to a functional human tissue or an array of functional human tissues formed by the described method.

EXAMPLES

Example 1

Printing Vascularized Tissues

To create 3D printed vascularized tissues, the following method (illustrated in FIGS. 17 and 18) was used:

Step 1: PDMS border was 3D printed using SE 1700 from Dow chemicals.

Step 2: Fugitive ink Pluronic F-127 or gelatin was 3D printed to create vascular channels.

Step 3: Cell laden ink #1 comprising cells mixed in 10% wt/v gelatin-fibrinogen or gelatin methacrylate (GelMA) hydrogels hydrogels containing a photoinitiator Irgacure-2959 at 0.3% wt/v was 3D printed.

Step 4: Cell-laden ink #2 I comprising cells mixed 10% wt/v gelatin methacrylate hydrogels containing a photoinitiator Irgacure-2959 at 0.3% wt/v was 3D printed.

Steps 1-4 above were repeated.

The resultant fugitive ink and cell-laden filaments were infilled with extracellular matrix comprising gelatin methacrylate at 10% wt/v containing 0.3% wt/v Irgacure 2959 photoinitiator.

The structure was then exposed to chemically crosslink the gelatin methacrylate.

Conditions:
Green with blue nuclei: GFP HNDFs stained with DAPI
Red with blue nuclei: RFP HUVECs stained with DAPI
Non-fluorescent with blue nuclei: 10T1/2 MFs
The ECM filed construct was then cooled to 4° C. and the fugitive ink was evacuated to produce the vascular network.

Next the HUVECs were introduced to line the channels to create blood vessels.

Figure 24:
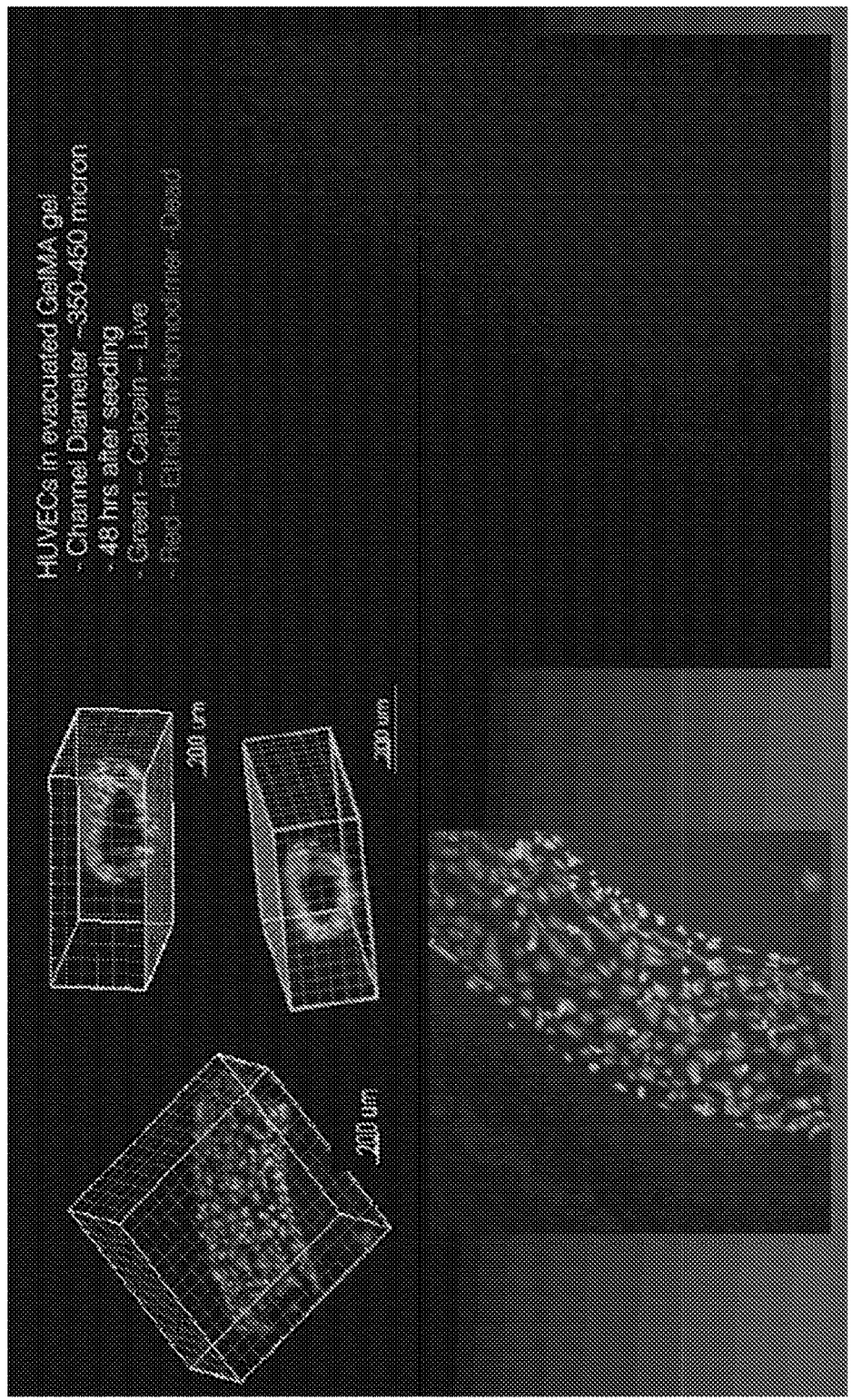
FIG. 24 shows endothelial vascular channels created by the described method. HUVECs are in evacuated GelMA gel.

FIG. 24 shows endothelial vascular channels created by the described method. HUVECs are in evacuated GelMA gel. The channel diameter was about 350-450 microns. Live cells shown in green were stained with calcein; dead cells shown in red were stained with ethidium homodimer.

Figure 25:
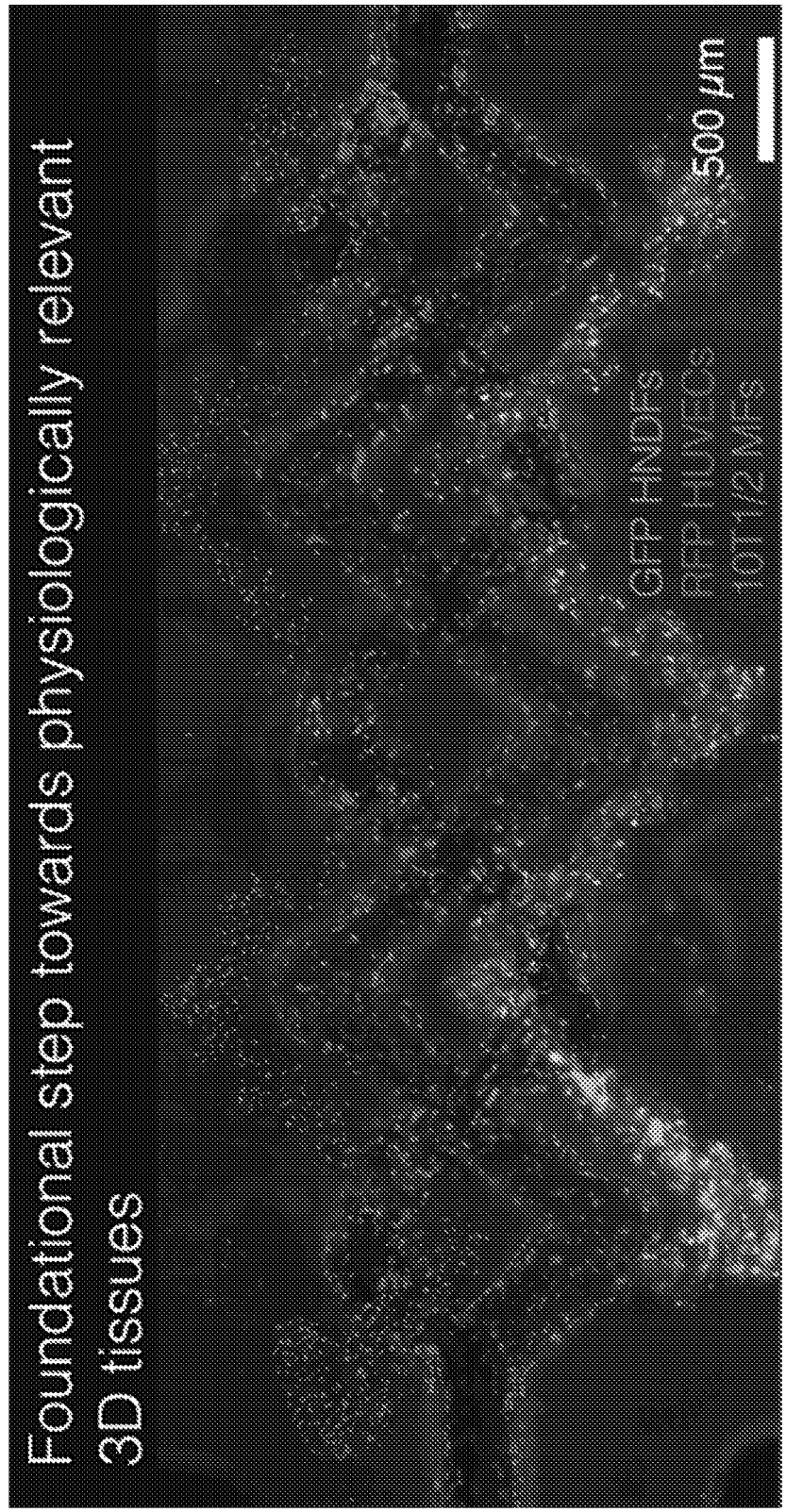
FIG. 25 shows a photograph of vascularized tissues.

FIG. 25 shows endothelial vascular channels (red cells) surrounded by printed regions of two cell types, 10T1/2 fibroblasts, and NIH 3T3 cells, printed in a GelMA gel.

Figure 26:
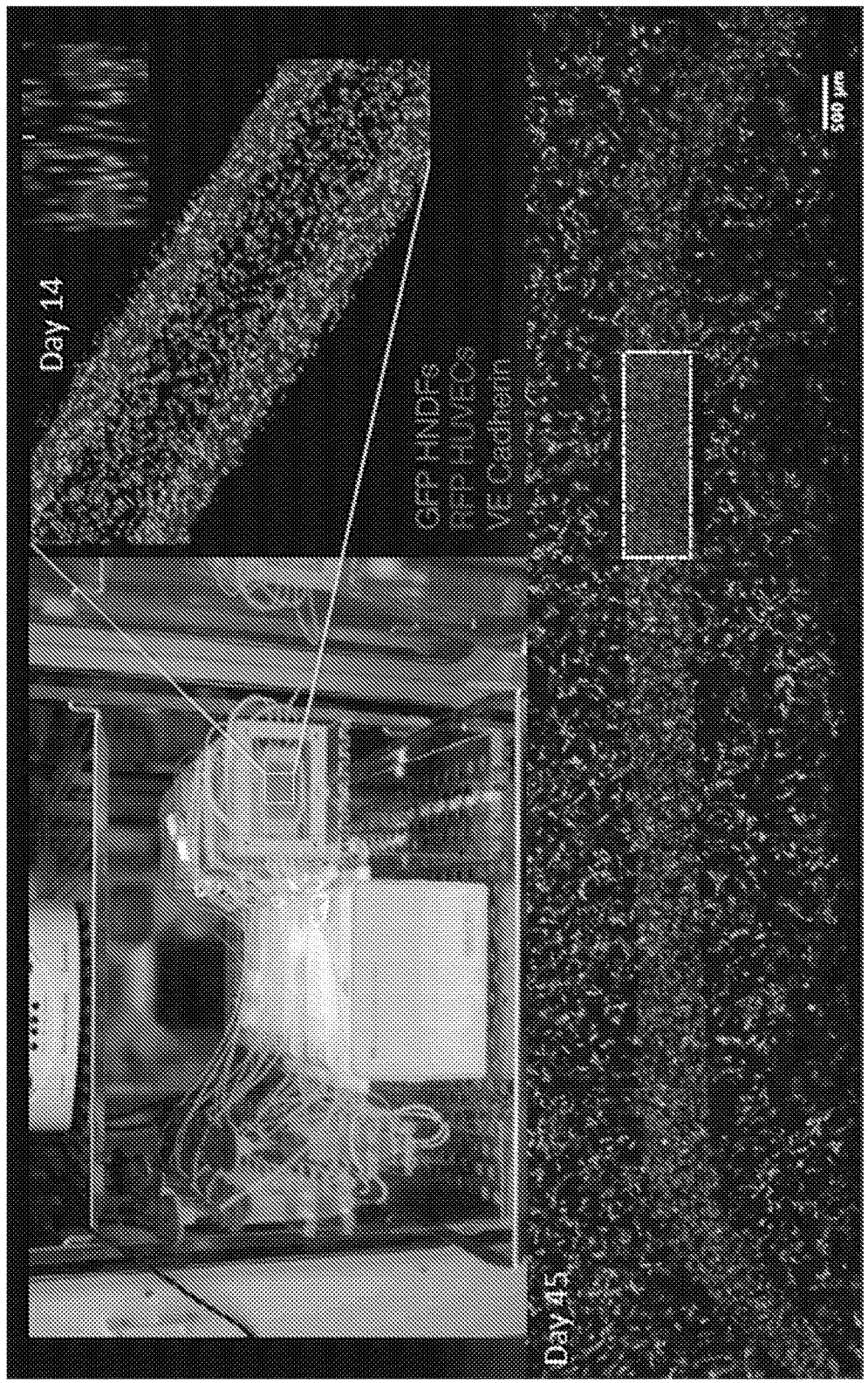
FIG. 26 shows a process of active perfusion of vascularized tissues.

FIG. 26 shows perfused endothelial vascular channels (red cells) that support the growth of surrounding HDNF fibroblasts (green). The channels are created in a gel using the described method, and the gel is embedded in a perfusion chip that facilitates the connection of the tissue to an external peristaltic pump that drives flow through the endothelial cell lined channels.

Example 2

Printing Endothelial Cell-Laden Fugitive Filaments

The fugitive ink, either Pluronic F-127 or gelatin contained live HUVEC cells, as shown in FIGS. 14A-G.

Cells were first dispersed in a Pluronic-F127 ink (FIGS. 14A and D), and then a 10% wt/v gelatin methacrylate matrix in DMEM media containing 0.3% wt/v Irgacure 2959 photoinitiator was cast surrounding the cells (FIGS. 14B and E) and crosslinked via UV exposure. Next, the Pluronic F-127 ink was liquefied by cooling to 4° C. and cells suspended in the ink were allowed to settle and stick to the wall (FIGS. 14C and F). After removal of the ink and culturing of the cells for several days, the cells remained adhered to the walls (FIG. 14G).

Example 3

Generating Cerebral Organoids

To synthesize a cerebral organoid (shown in FIGS. 7A-I) the following method was used.

6-well plates were coated in matrigel by incubating human ESC-certified growth-factor depleted Matrigel, diluted in DMEM/F12 medium at the manufacturer's (Corning) batch specific recommended concentration, for 1 h at room temperature Human iPSCs were maintained in mTeSR medium on the matrigel coated plates and passaged using Accutase when colonies begin to merge.

At passaging, Human iPSCs were dissociated for 15 minutes using 1 mL Accutase reagent, then diluted in 11 mL of DMEM/F 12 medium, centrifuged at 200 g for 5 minutes, resuspended in 1 mL of AW medium, counted using a cellometer, and seeded at a density of 600,000 cells per well of an Aggrewell™ 400 plate, which corresponds to a per-microwell density of 500 iPSCs (FIG. 7A). The media volume was brought up to 2 mL using AW, containing 10 µM ROCK inhibitor Y-27632. The time point 'day 0' corresponds to the day that the iPSCs were first seeded in Aggrewells™.

After 24 hours (day 1), the iPSCs had formed embryoid bodies (FIG. 7B), and the embryoid bodies were harvested by gentle pipetting and transferred into ultra-low adhesion plates (Corning, Inc.) and maintained in AW medium without ROCK inhibitor for 2 days.

On day 3, embryoid bodies were transferred into NIM and cultured for 5 days (FIGS. 7D-F) before being transferred into NDM1 (FIG. 7G).

On day 11, cerebral organoids were transferred into 1 µL droplets of Matrigel by pipetting 800 nL of ice cold Matrigel onto a sheet of parafilm, and adding 200 nL of media containing the organoid to the droplet. The Matrigel droplet was then maintained at 37 C for 10 minutes for the Matrigel to gel, and then transferred into a spinning bioreactor containing NDM1 (as shown, e.g., in FIG. 5A).

On day 18, the flask media was changed to NDM2. The media was replaced weekly.

Example 4

Confirming Endothelial Progenitors in Sprouting Embryoid Body

Sprouting embryoid bodies were formed by following the procedure outlined in Example 3, but replacing the use of NIM with EGM-2 medium, and NDM1 and NDM2 media were supplemented with 100 ng/ml of VEGF to encourage endothelial development and proliferation.

Figure 27:
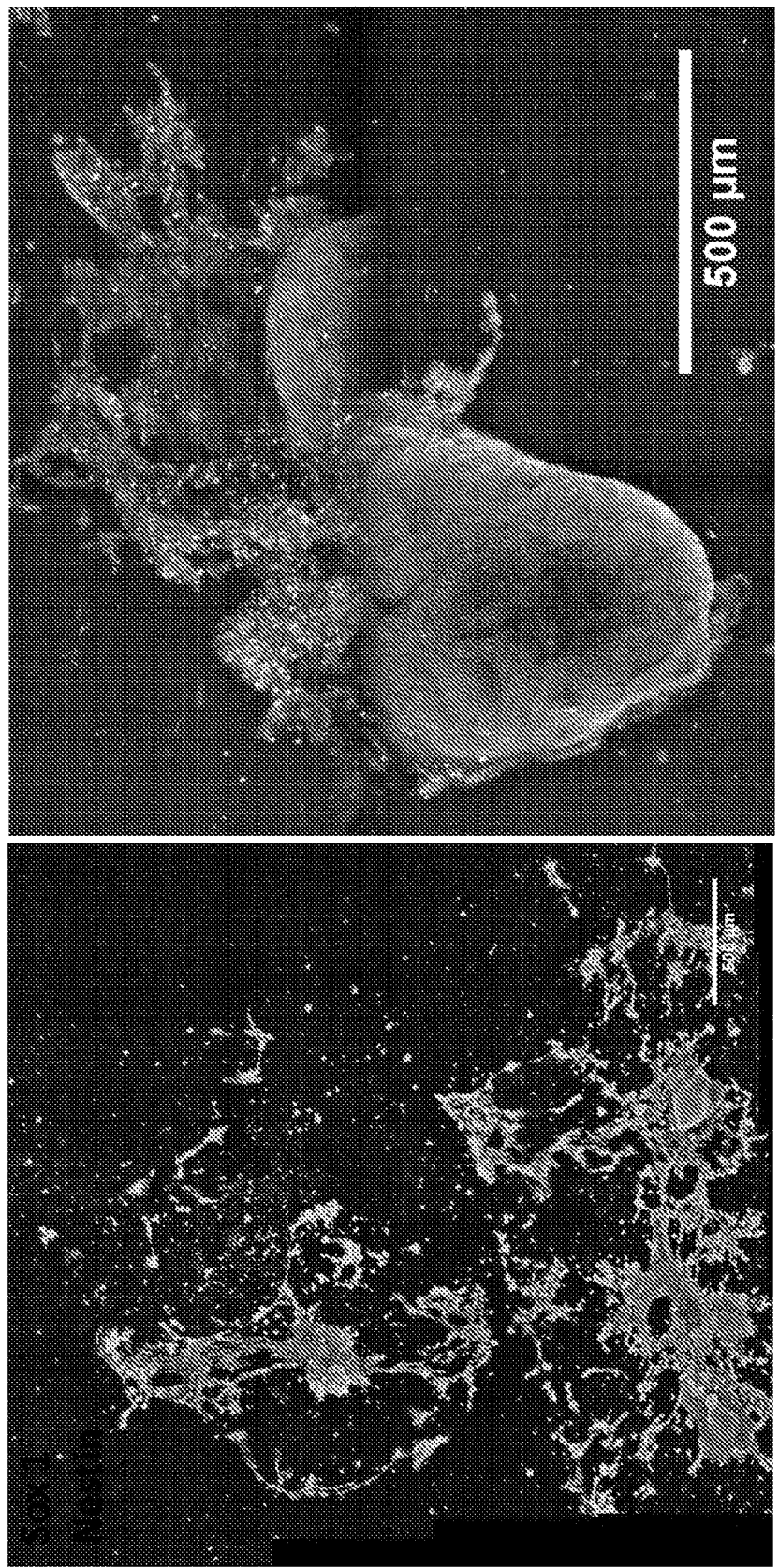
FIG. 27, left image, shows organoids analyzed by immunofluorescence for nestin (green) (a neural progenitor marker, and an endothelial marker), and Sox 1 (a neural progenitor marker) (red)

As shown in FIG. 27, left image, organoids formed using this process were analyzed by immunofluorescence for nestin (green) (a neural progenitor marker, and an endothelial marker), and Sox 1 (a neural progenitor marker) (red). The strong staining of nestin, and absence of Sox 1, as well as the tubular morphology of the cells suggests an endothelial lineage. (FIG. 27, right image). When stained for Sox 1 (green) and VE-Cadherin (red) (a specific endothelial marker), the presence of neural rosettes (green circles) in organoid body and co-presence of vasculature (red) was detected.

Figure 28:
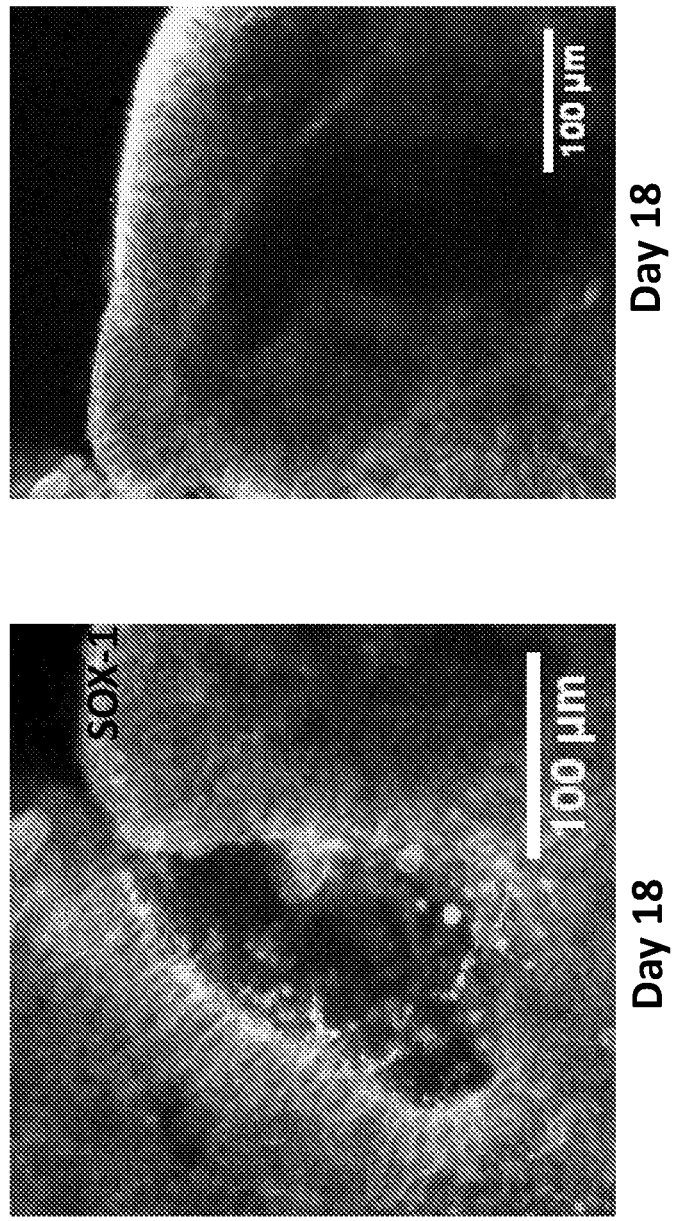
FIG. 28 depicts organoids stained for presence of neuronal structures.

Results shown in FIG. 28 further confirm the presence of cortical structures with mature neurons.

Example 5

Confirming Presence of Neural Structures

To confirm presence of neural structures in cerebral organoids, cerebral organoids were developed according to the protocol in Example 3, and immunostained for Sox 1 (green) and neuron-specific β-III tubulin, also known as the clone Tuj-1 (red). As shown in FIG. 28, the radial arrangement of neural projections confirms a cerebral organoid phenotype.

Example 6

Generating Vascularized Cerebral Organoids from iPSCs

Figure 29:
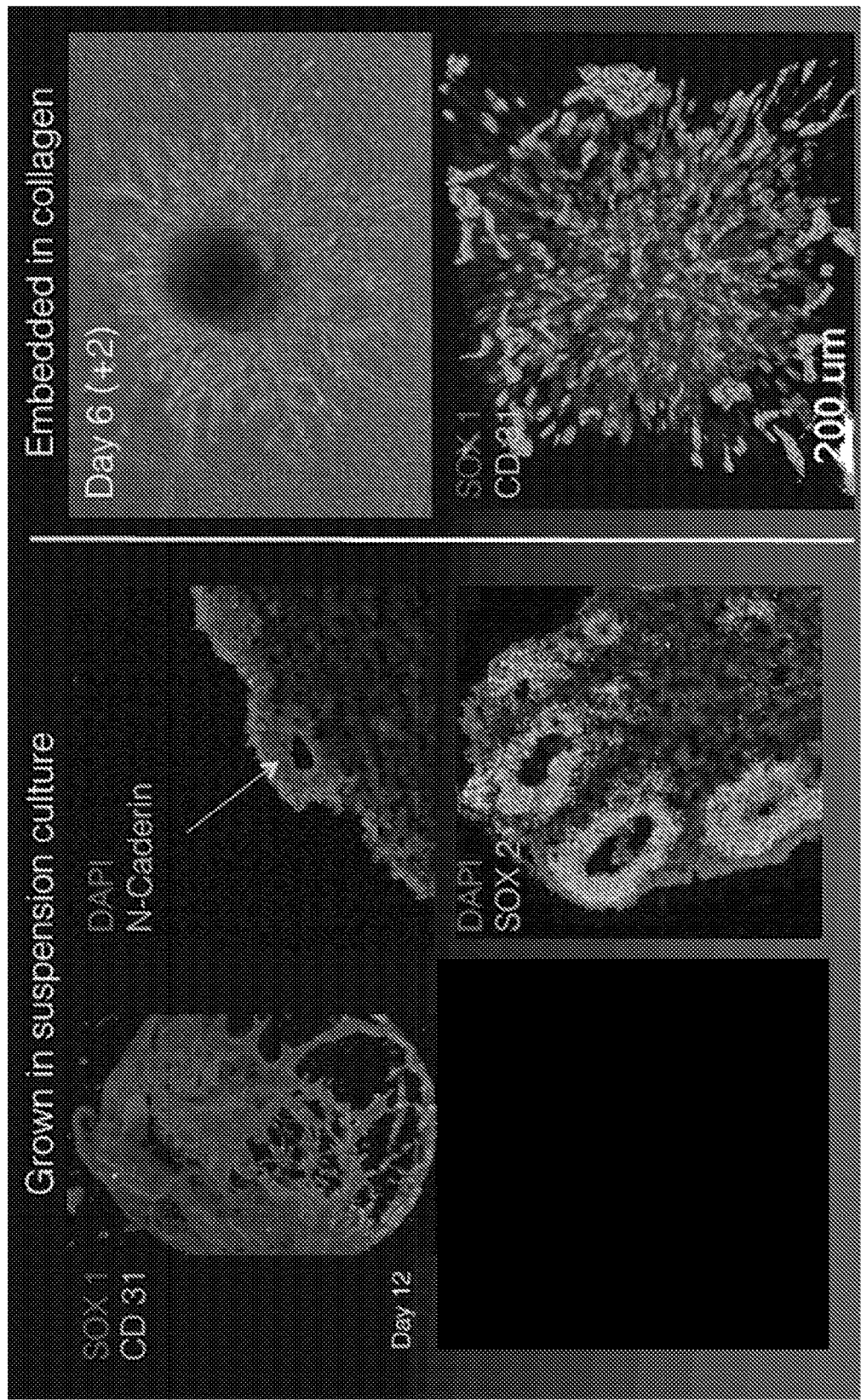
FIG. 29 depicts vascularized cerebral organoids from iPSCs.
Figure 30:
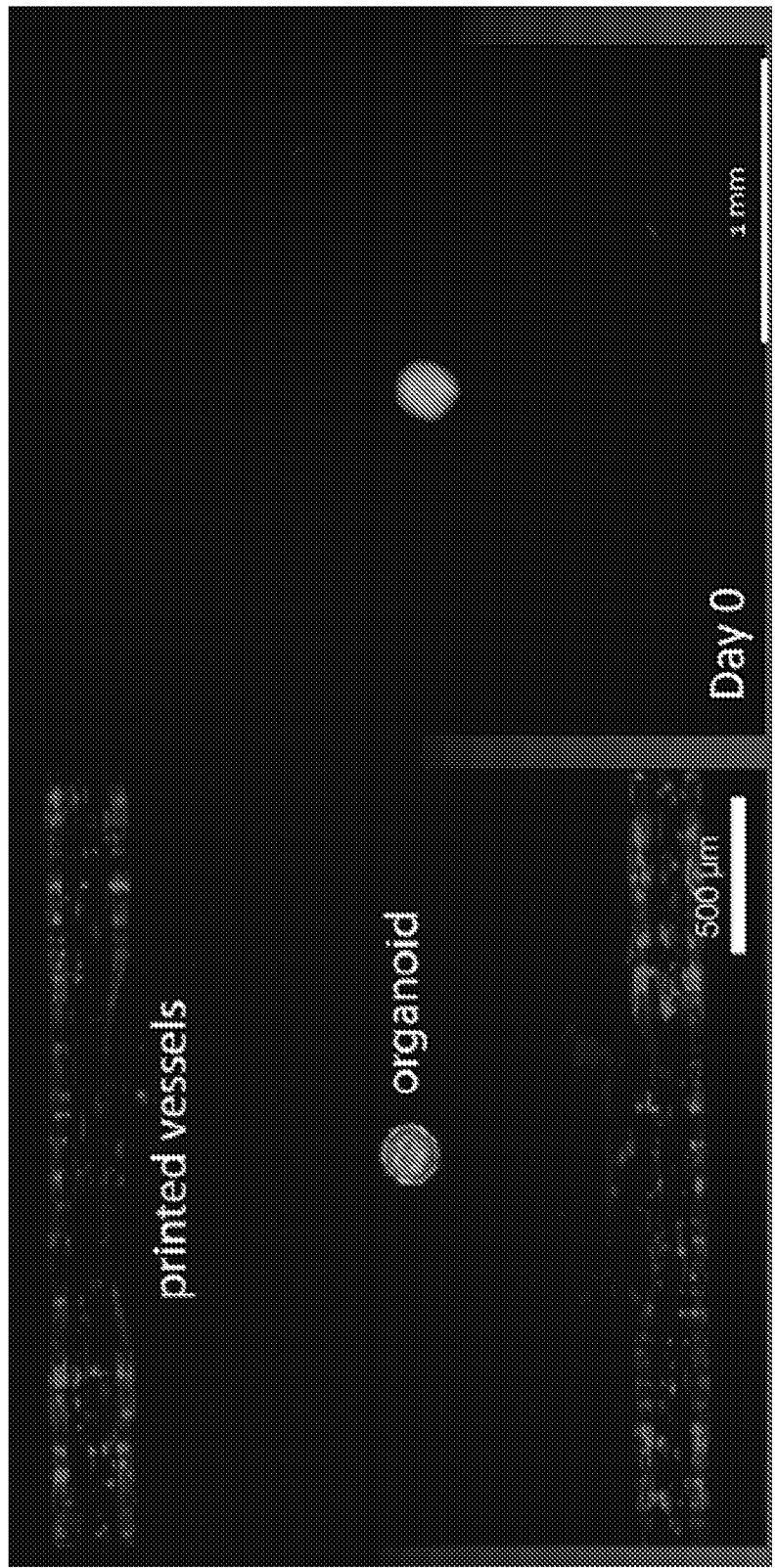
FIG. 30 shows cerebral organoids within perfusable vascularized matrices.

The following method was used to synthesize vascularized cerebral organoids from iPSCs shown in FIGS. 29 and 30.

Vascularized cerebral organoids were prepared by the method outlined in Example 3, but instead of using NIM, embryoid bodies were cultured in EGM-2 medium supplemented with 1:100 N2 supplement. NDM1 and NDM2 were also supplemented with 100 ng/ml of VEGF.

Organoids formed using this process were analyzed by immunofluorescence for neural progenitor cells (Sox 1) and vascular endothelial cells (CD 31) which are shown in red and green, respectively, in the top-left image. To further study neural structures contained within organoids cultured using this process, we stain for N-cadherin (green, top right image) which, following natural neural development, is shown to line the ventricular wall. The bottom-right image is stained for (Sox 2) which identifies the neural stem cells that form the neural rosettes that surrounds the ventrical like structure. Both the top-right and bottom-right images are stained with DAPI (blue) which is localized with cell nuclei.

Example 7

Creating a Multi-Population Organoid (Approach 1)

To determine whether a multi-population organoid can be synthesized using the 'common sense' approach of mixing human umbilical-vein endothelial cells (HUVECs) with induced pluripotent stem cells (iPSCs), the following method was used.

iPSCs were cultured as outlined in Example 3, but prior to adding the iPSCs into the Aggrewells™, cells were mixed in a 1:1 ratio with HUVECs, then the mixture was added to the Aggrewells™ and centrifuged for 3 minutes at 100 g.

As shown in FIG. 31, initially, the two types of cells dispersed in the medium. However, at day 1, the 'common sense' approach of mixing HUVECs with iPSCs results in a 'phase separation' of the two cell types into their two distinct populations. Shown in green are iPSCs; shown in red are HUVECs.

Example 8

Vascularizing Multi-Population Organoids

Human induced pluripotent stem cells (iPSC's) were maintained in culture on vitronectin coated non-tissue culture treated 6-well plates in mTeSR1 medium. To passage, cells were treated with accutase for 5 minutes, rinsed with DMEM/F12 containing 15 mM HEPES, and gently triturated by pipetting up and down twice with a P1000 pipette tip. Cells were then replated in mTeSR1 medium containing 10 µM Rho-kinase inhibitor (ROCK-i). After 12-20 hours, the cells were replaced in mTeSR1 without ROCK-i, and media was changed every day.

To form embryoid bodies, at 'Day 0', cells were passaged as described above, except for using a longer, 15 minute accutase treatment to separate the colonies into single cells to aid accurate counting. Once counted, the iPSC's were added to an Aggrewell™ 400 plate, at a total density of 500 cells per micro-well, centrifuged at 100 g for 3 minutes, and cultured in 2 ml accutase containing 10 µM ROCK-i to form embryoid bodies. At this point, if a genetically modified population of iPSC's is to be used, they can be added and mixed to the single cell suspension of wild-type iPSC's at a defined cell-count ratio, added to the Aggrewell™ plate, then centrifuged at 100 g for 3 minutes to generate a mixed population of cells in each micro well.

After 20 hours, 'Day 1', embryoid bodies were formed in the microwells, and the media was replaced with Aggrewell™ medium without ROCK-i. Media was changed daily until 'Day 3', at which point embryoid bodies were removed from the microwells by gentle pipetting and cleaned by rinsing on the surface of a 40 µm reversible cell filter, before flipping the filter to release the embryoid bodies using 5 ml of NIM supplemented with 1:100 N2 supplement. Embryoid bodies were transferred to ultra-low adhesion 6-well plates for suspension culture, and are agitated twice per day to prevent aggregation.

After four days in suspension culture 'Day 7', cells were implanted into a microvascular scaffold formed by either pin-casting or molding around a sacrificial printed filament of either Pluronic F-127 or gelatin. The matrix was comprised of matrigel mixed with either rat rail collagen type I (2 mg/ml) or fibrinogen (10 mg/ml). The vascular network contained two independent networks, an 'arterial' and a 'venous' network. The culture medium was switched to neural differentiation medium, phase 1, comprising a 1:1 mixture of DMEM/F12 and Neurobasal, supplemented with 1:200 N2 supplement, 1:100 B27 supplement without vitamin A, 1:200 MEM-NEAA, 1× glutamax, and 1× β-mercaptoethanol. Next, specific angiogenic factors were added to one or both networks to encourage vascular sprouting. Media was pumped through the two independent networks by means of a peristaltic pump, and media was replaced every two days.

At 'Day 11', the media was replaced with neural differentiation medium, phase 2, which is the same as neural differentiation medium, phase 1, except that the B27 without vitamin A was replaced with B27 with vitamin A.

DOX was added at 100 ng/ml to the medium (can be added at any phase of the differentiation process) to induce the transdifferentiation or directed differentiation of the genetically modified iPSC's. Furthermore, a second, orthogonal signal can be added to the media conditions described to induce sprouting of induced endothelium to enhance the formation of a capillary plexus that connects both venous and arterial systems. Adding an angiogenic factor can provide a gradient to induce directional angiogenesis.

Once angiogenesis has occurred sufficiently to connect the two networks, the positive pressure is applied, via a peristaltic pump to only the arterial side, allowing fluid flow through the connecting capillaries to the venous side.

Figure 32:
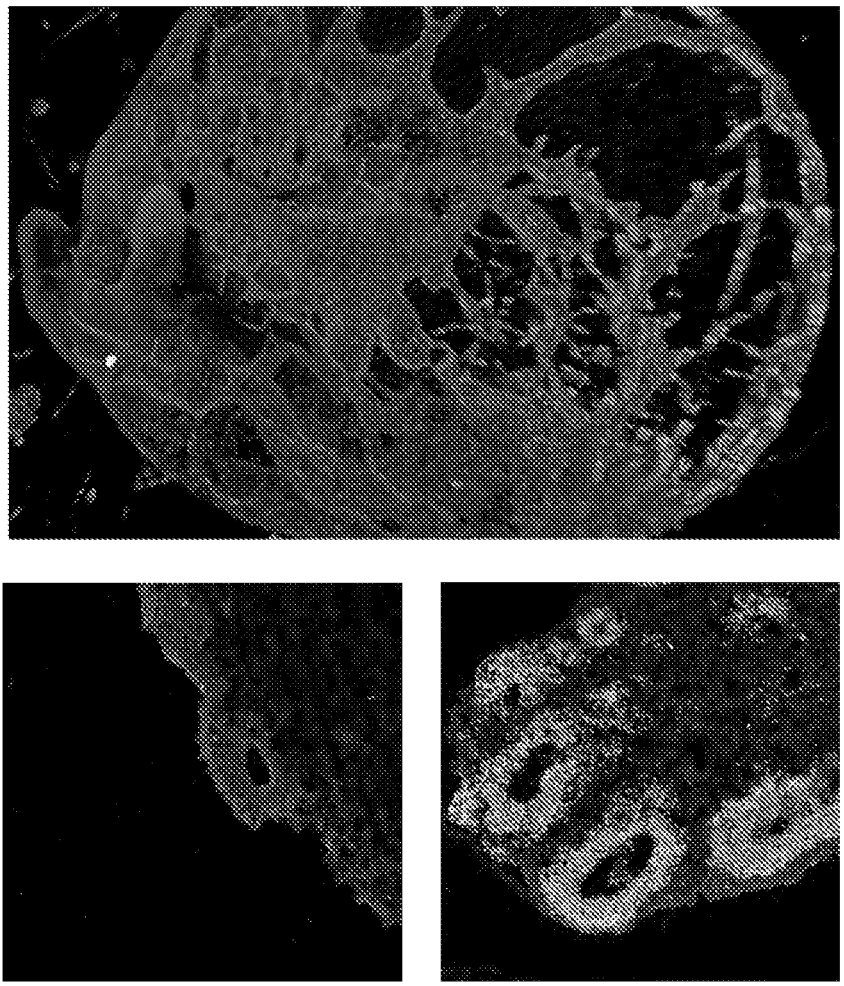
FIG. 32 depicts organoids produced by combining neuronal and endothelial protocols into a hybrid protocol.

As shown in FIG. 32, a fluorescent and non-fluorescent population of iPSCs, representing a genetically modified subpopulation and a wild-type subpopulation, respectively, can be mixed prior to adding into Aggrewells™ (FIG. 32, left image). After 20 h in vitro, the iPSCs coalesce to form an evenly distributed mixed population of wild-type and genetically modified iPSCs.

Example 9

ETV2 Can Efficiently Induce Endothelial Phenotype

Figure 33:
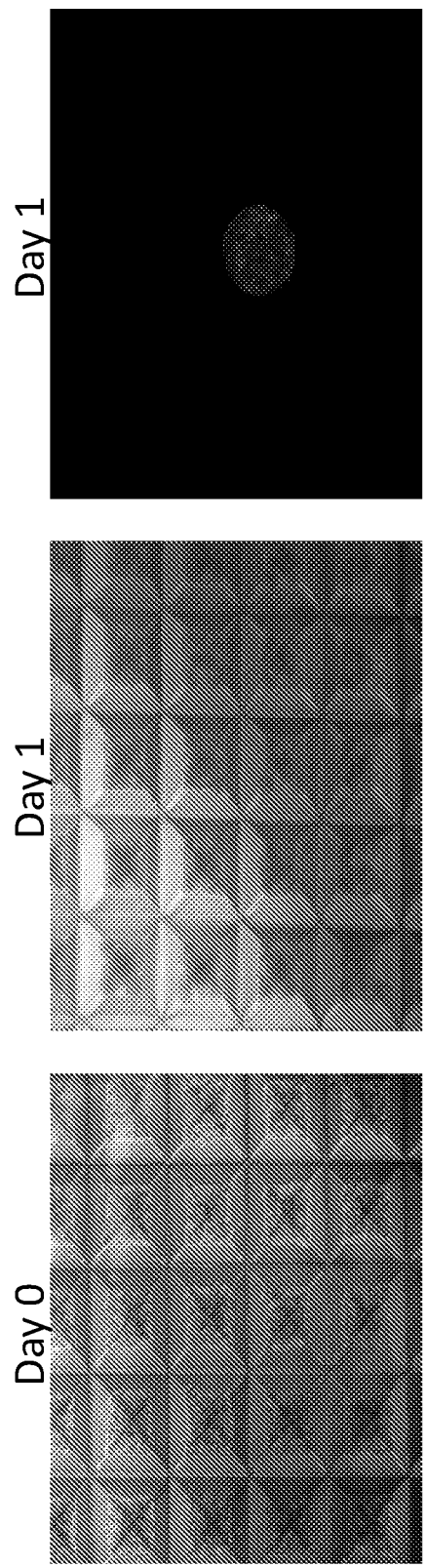
FIG. 33 shows that populations of iPSCs that have been transformed with a doxycycline inducible promoter for a different transcription factors can be directly-differentiated to endothelial cells with varying degrees of efficiency when doxycycline is added to mTeSR1 medium.

FIG. 33 shows that populations of iPSCs that have been transformed with a doxycycline inducible promoter for a different transcription factors can be directly-differentiated to endothelial cells with varying degrees of efficiency when doxycycline is added to mTeSR1 medium.

Figure 34:
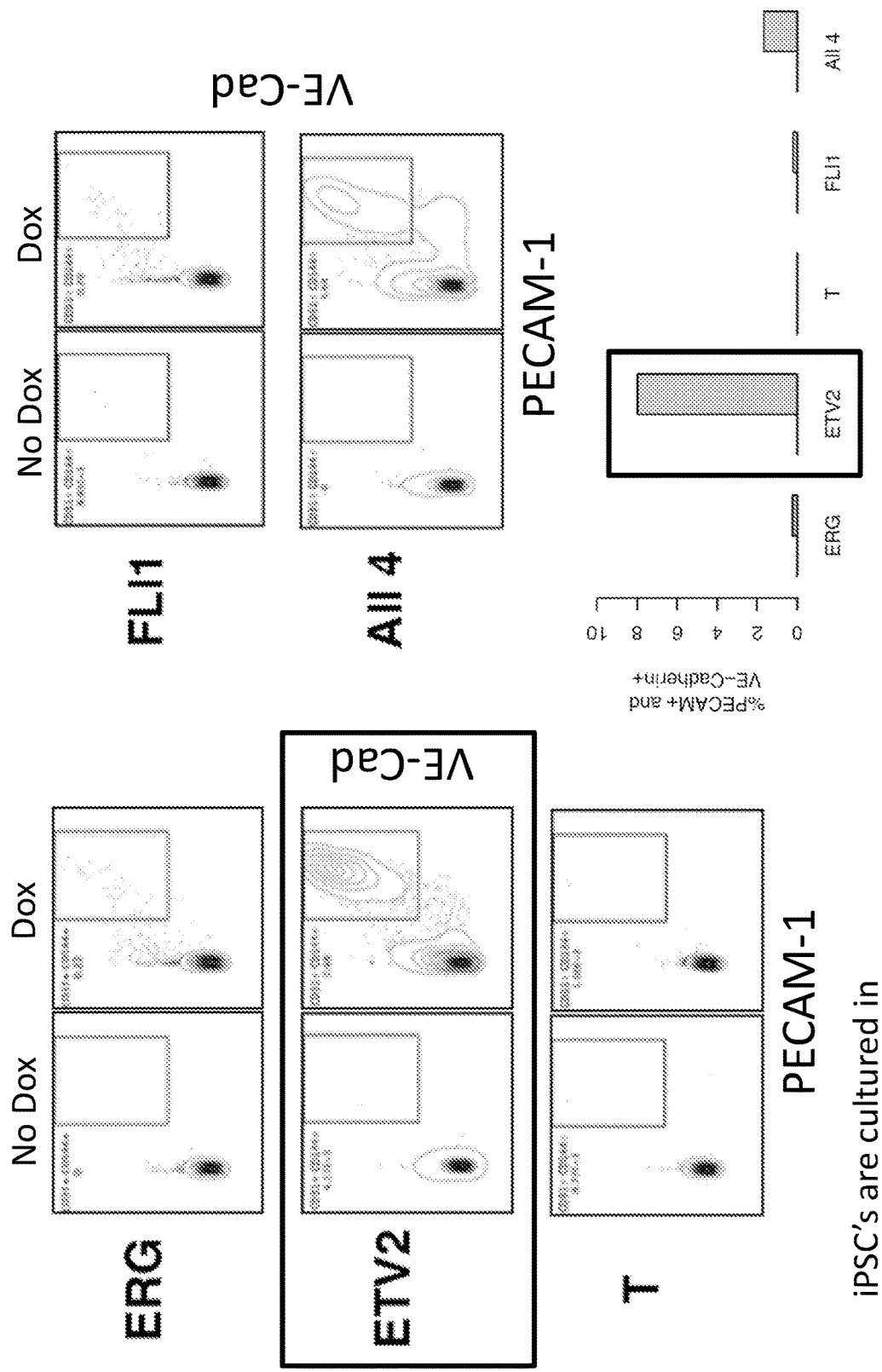
FIG. 34 shows flow cytometry data for two endothelial genes, PECAM-1 (also known as CD31) and vascular endothelial cadherin (VECad).

Specifically, 5 separate populations of iPSCs were transformed, using electroporation of a PiggyBac transposon system, with either the transcription factor ETS-related gene (ERG), ETS-varient 2 (ETV2), Brachyury (T), or a combination of all four of the listed transcription factors (All 4). FIG. 34 shows flow cytometry data for two endothelial genes, PECAM-1 (also known as CD31) and vascular endothelial cadherin (VECad).

In this example, doxycycline-induced overexpression of ETV2 resulted in the largest percentage of cells (~8%)

converting to an endothelial state after 5 days in mTeSR1 medium containing 500 ng/ml of doxycycline. The overexpression of all 4 transcription factors also resulted in a measurable expression of vascular markers, but was less efficient than overexpression of ETV2 alone.

FIG. 35 shows iPSCs that were transformed with a dox-inducible ETV2 vector and were cultured for 5 days in mTeSR1 containing 500 ng/ml doxycycline resulted in a significant number of cells exhibiting an endothelial 'cobblestone' morphology that after performing an immunofluorescence protocol, stained brightly for VECadherin (right image, orange cells) and several co-stained with CD-31 (right image, purple cells), while those that were cultured in mTESR1 alone remained pluripotent, as visualized by positive Oct4 staining (left panel, green cells).

Example 10

ETV2 Overexpression can Induce Endothelium in 3D Culture

Embryoid bodies were prepared in Aggrewell™ plates as described in Example 3 using ETV2 transformed iPSCs.

Figure 36:
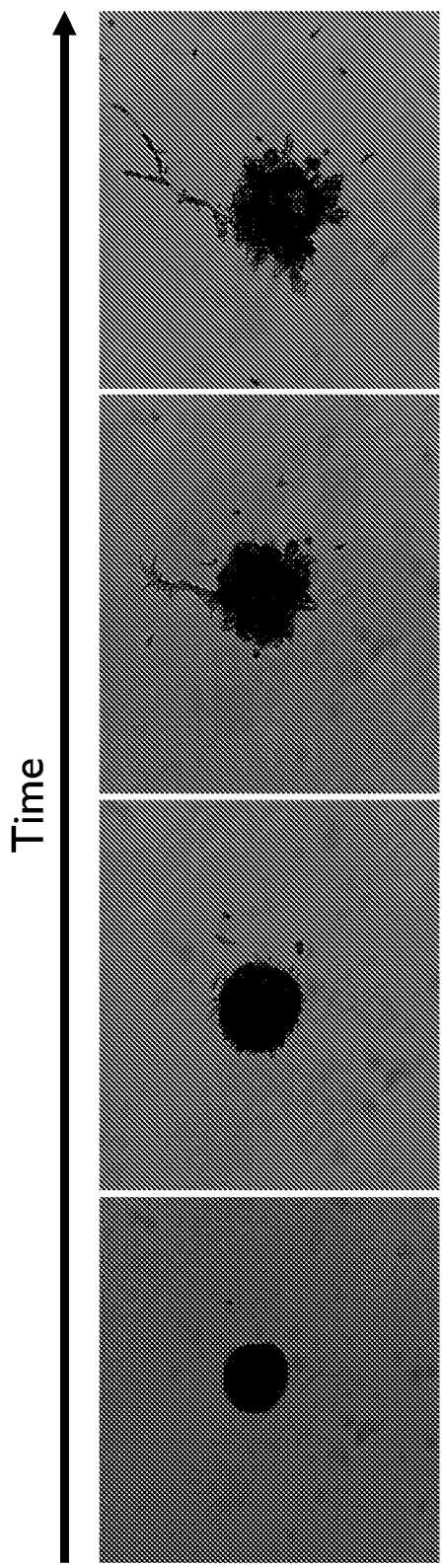
FIG. 36 shows a time series of phase contrast micrographs of an dox-inducible ETV2 embryoid body harvested from Aggrewells™ at day 3 and cultured in a droplet of Matrigel bathed in neural induction medium containing doxycycline.

FIG. 36 shows a time series of phase contrast micrographs of an embryoid body harvested from Aggrewells™ at day 3 and cultured in a droplet of Matrigel bathed in neural induction medium containing 500 ng/ml doxycycline. Visible vascular sprouts begin protruding within 12 hours of culture.

Figure 37:
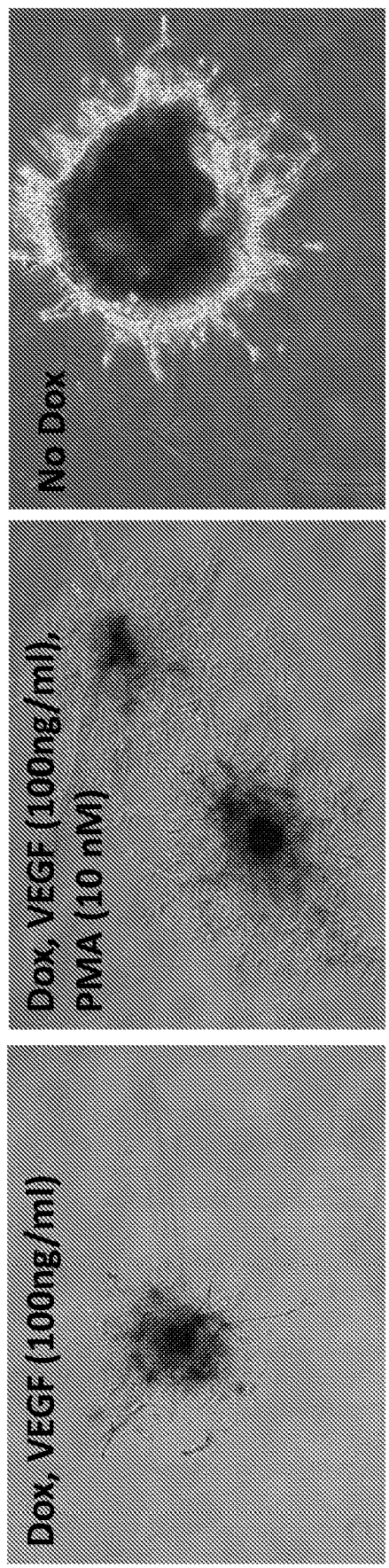
FIG. 37 depicts vascular sprouting in 10 days, cultured in matrigel using cerebral organoid culture conditions with and without doxycycline, VEGF or PMA.

FIG. 37 shows vascular sprouting in 10 days-cultured in matrigel using cerebral organoid culture conditions. By adding 10 nM PMA, a PKC-alpha activator, vascular sprouting was dramatically increased. However, PKC also mediates neurite outgrowth, and may interfere with cerebral organoid development.

Example 11

100% ETV2 Inducible Cells Generate Vascular Plexus

Figure 38:
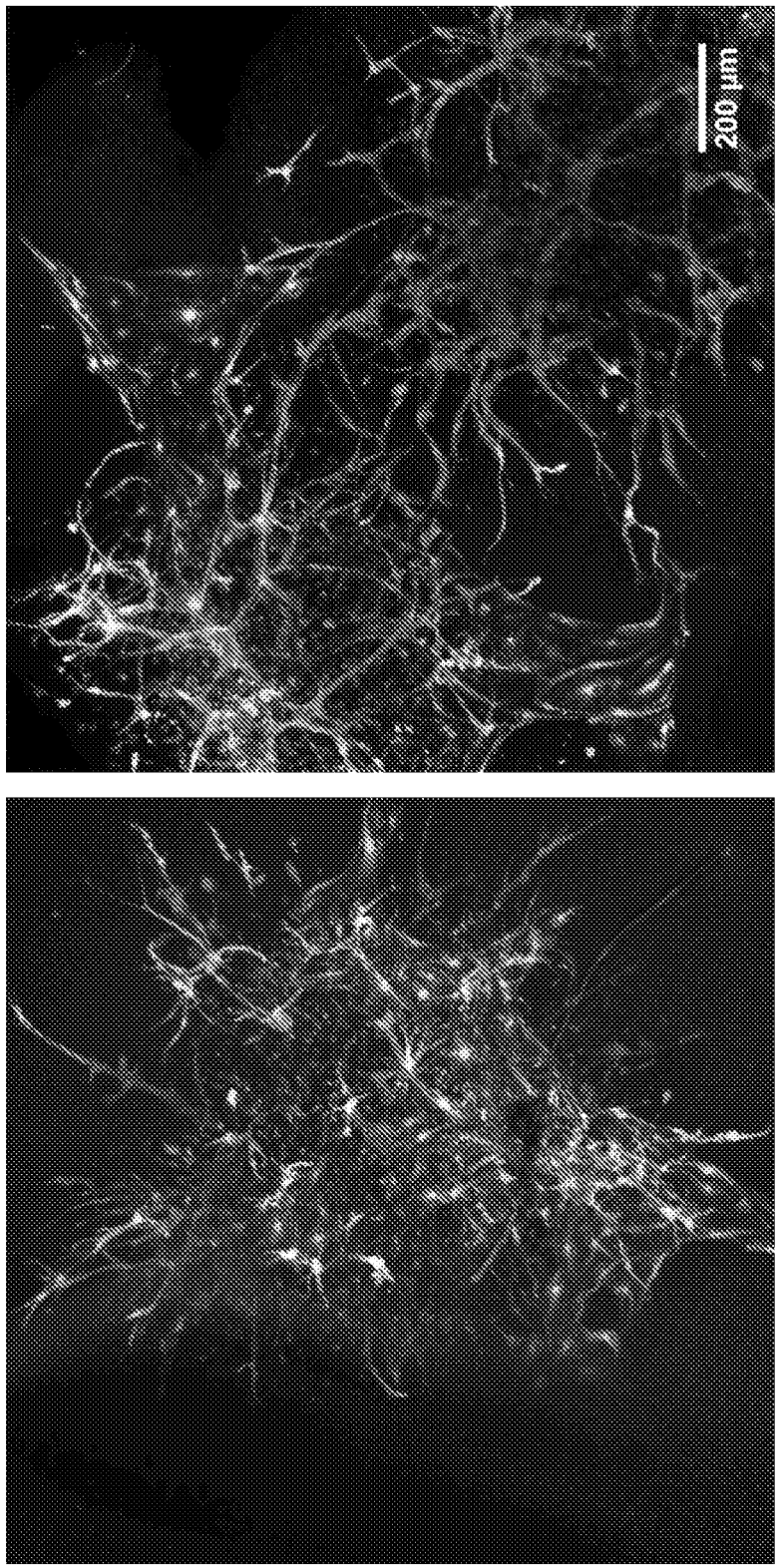
FIG. 38 shows embryoid bodies formed using a suspension of doxycycline inducible ETV2 expressing iPSCs prepared in Matrigel as described in Example 10.

FIG. 38 shows embryoid bodies formed using a suspension of doxycycline inducible ETV2 expressing iPSCs prepared in Matrigel as described in Example 10. NIM, and NDM1 media were used as described in Example 3 but supplemented with 500 ng/ml doxycycline. On day 11, embryoid bodies were fixed and stained using standard immunofluorescence protocols.

Referring to FIG. 38, the images demonstrate the development of a sprouting vascular plexus as indicated by the positive staining of VE-Cadherin (red cells) with no discernable neural progenitor cells found (as indicated by the absence of Sox 1 expressing cells).

Example 12

Long-Term Cerebral Organoid Culture

Figure 39:
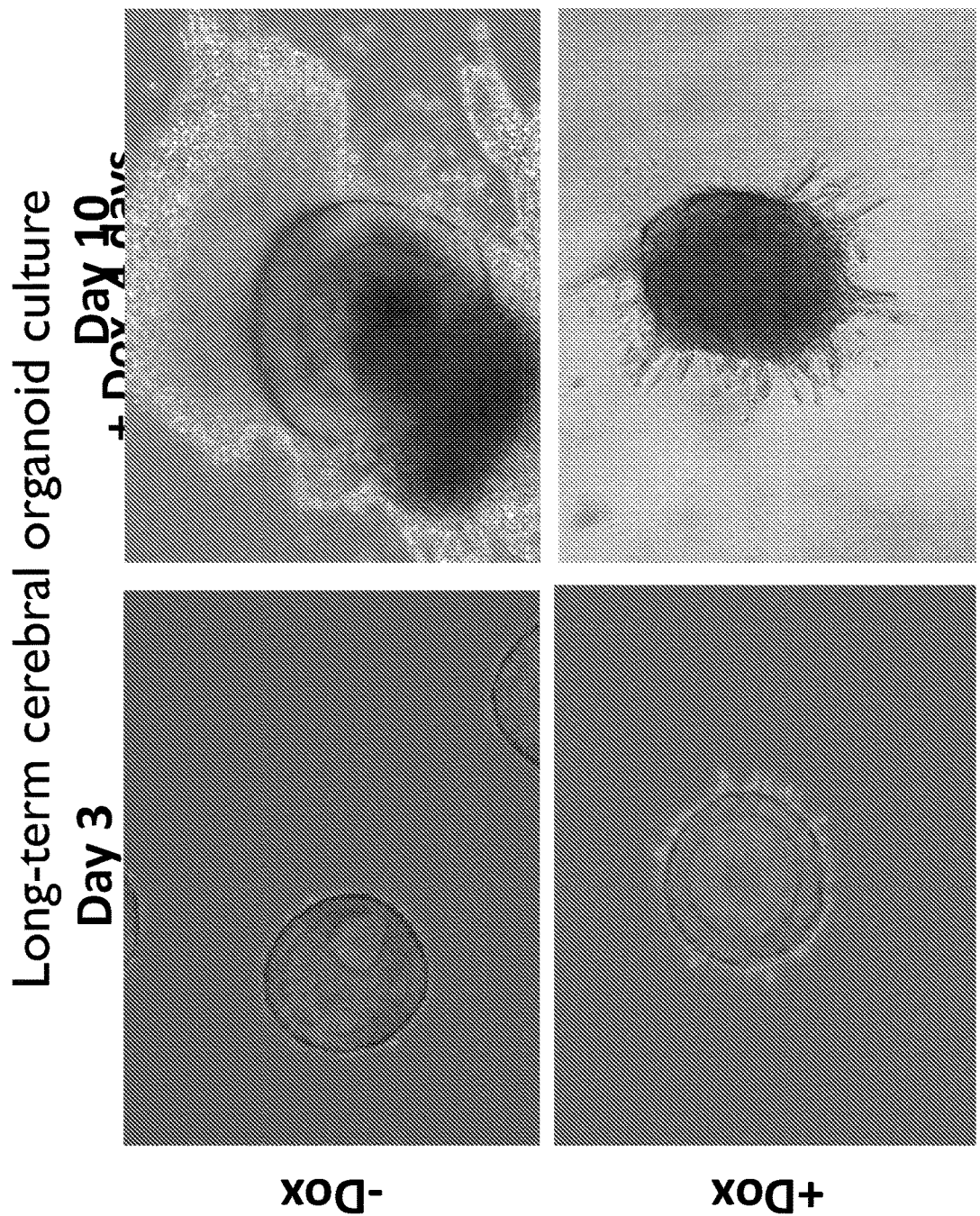
FIG. 39 shows embryoid bodies formed using a suspension of doxycycline inducible ETV2 expressing iPSCs.

FIG. 39 shows embryoid bodies formed using a suspension of doxycycline inducible ETV2 expressing iPSCs prepared as described in Example 10, except that on day 1, embryoid bodies were harvested and mixed into 2 mg/ml of rat tail collagen, type I, in AW medium and neutralized with sodium hydroxide. The collagen solution containing embryoid bodies was then pipetted into 6-well plates, and incubated at 37° C. to enable formation of collagen fibrils. Next, 2 ml of AW medium was pipetted on top of the gel. On day 3, embryoid bodies were transferred into NIM without doxycycline (top row) or with doxycycline (bottom row), and cultured for 5 days. On day 8, the NIM medium was replaced with NDM1 with (bottom row) or without (top row) doxycycline. By day 10, phase contrast imaging displayed a clear phenotypic difference between embryoid bodies cultured with or without doxycycline. The embryoid bodies that were cultured without doxycycline had large neuroepithelial regions (arrows) visible in phase contrast. Those that were cultured with doxycycline exhibited a sprouting endothelial phenotype.

Example 13

Titrating Percentage of Wildtype vs. ETV2 Inducible Cells

Embryoid bodies were formed as described in Example 3, except that before seeding the cells into Aggrewell™ plates, a mixed suspension of wild-type iPSCs and drug inducible ETV2 cells were mixed at a ratio of 4:1 (wild-type:ETV2). In addition, doxycycline was added to NIM, NDM1 and NDM2 at 500 ng/ml, and cerebral organoids were not embedded in Matrigel and were cultured in suspension culture, without the use of the spinning flask. At day 14, the resulting vascularized cerebral organoid was fixed and stained using standard immunofluorescence protocols.

Figure 40:
FIG. 40 shows an immunofluorescence stained vascularized cerebral organoid.

FIG. 40 shows an immunofluorescence stained vascularized cerebral organoid. In this organoid, there are clear regions of neural progenitor cells, as highlighted by Sox 1 expression (purple), followed by an outer layer of neural cells that arise from the underlying layer of neural stem cells, as indicated by neuron-specific βIII-tubulin expression (green). Furthermore, the organoid was surrounded by a vascular plexus, as indicated by a positive staining for VE-cadherin (red).

Example 14

Embedding Mixed Organoids in Matrigel Between Perfusable Channels

Figure 41:
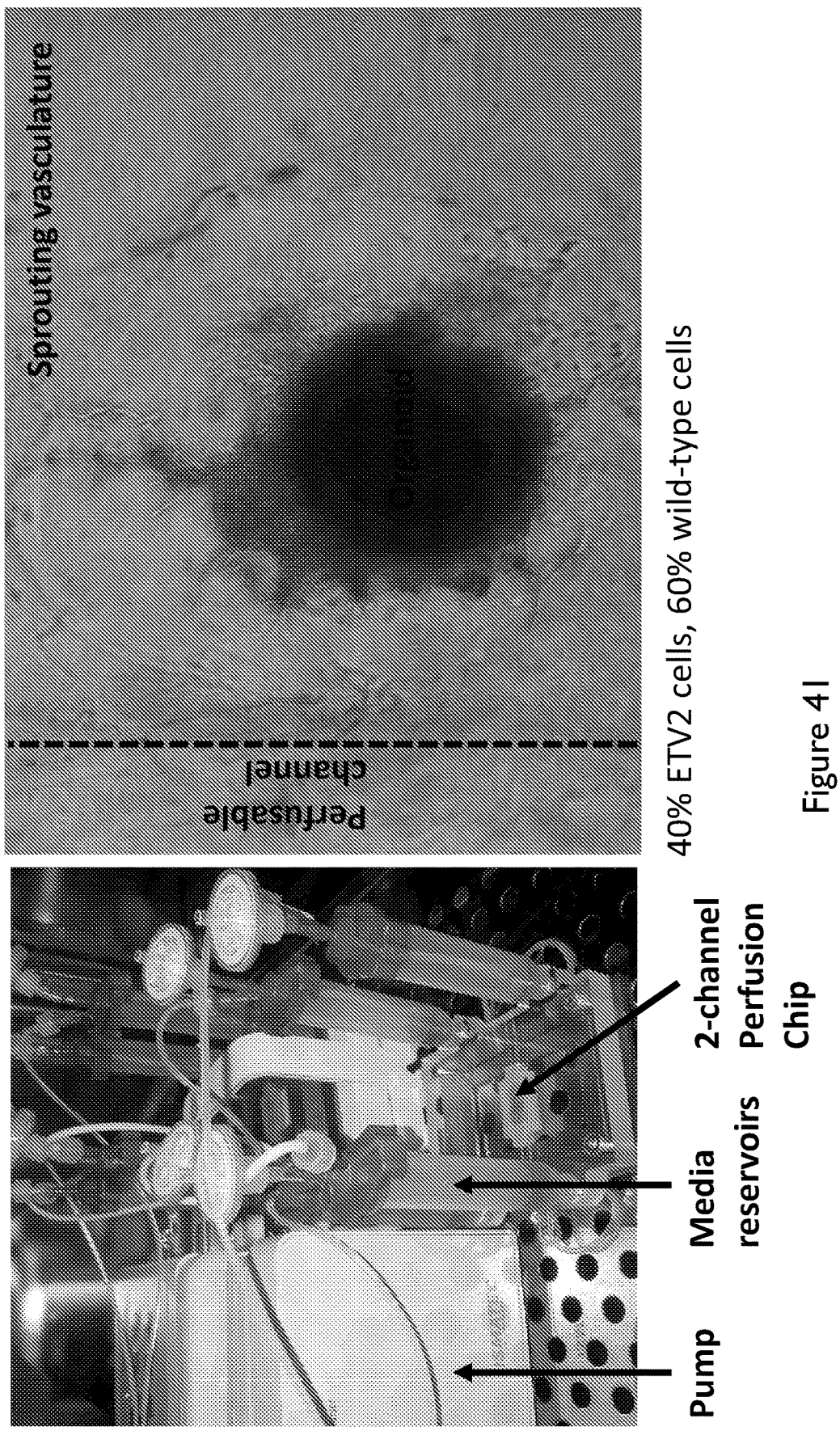
FIG. 41 depicts a 3D printing apparatus (left) used to create an organoid with vascular sprouts (right).

FIG. 41 shows an organoid that underwent the following procedure.

Embryoid bodies were formed according to the process outlined in Example 3, except that a mixture of wildtype (60%) and drug-inducible ETV2 cells (40%) were used to seed the Aggrewells™.

On day 1 after seeding in Aggrewell™ plates, embryoid bodies were harvested and placed in ultra-low adhesion plates in AW for 2 d.

On day 3, the media was changed to NIM containing 500 ng/ml doxycycline.

On day 5, an embryoid body was injected into a Matrigel droplet, using a method outlined in Example 10.

After gelation in an incubator for 10 minutes at 37° C., the Matrigel droplet was added to a collagen gel containing two linear perfusable channels. The Matrigel was positioned such that they organoid lay between the two channels. Next, the external channels were connected to fluid reservoirs which were allowed to gravity-feed through the channels via hydrostatic pressure, and which was recirculated continuously via a peristaltic pump. The organoid was grown in neural induction medium with doxycycline for a total of 8 days and the phase contrast image was taken on day 11. Referring to FIG. 41, vascular sprouts can be seen emerging from the central, dense organoid and the sprouts are approaching the adjacent perfusable channel.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. An in vitro method of generating functional human tissue, the method comprising:
   (a) embedding an embryoid body or organoid in an in vitro tissue construct, the tissue construct comprising:
      (i) a first vascular network comprising one or more interconnected vascular channels, and
      (ii) a second vascular network comprising one or more interconnected vascular channels;
   (b) exposing the embedded embryoid body or organoid to one or more of a biological agent gradient, a pressure gradient, and/or an oxygen tension gradient, thereby inducing angiogenesis of capillary vessels to and/or from the embryoid body or organoid via delivery of the gradient by at least one of the first and the second vascular networks; and
   (c) wherein exposing the embedded embryoid body or organoid to one or more of a biological agent gradient, a pressure gradient, and/or an oxygen tension gradient promotes vascularizing the embryoid body or organoid, the capillary vessels connecting the first vascular network to the second vascular network, thereby creating functional human tissue having a single vascular network and a perfusable tissue structure.

2. The method of claim 1, wherein the biological agent gradient includes one or more of the following: growth factors, morphogens, small molecules, drugs, hormones, DNA, shRNA, siRNA, nanoparticles, mRNA, modified mRNA.

3. The method of claim 1, wherein the one or more interconnected vascular channels are formed by a manufacturing process or by a biological developmental process that includes at least one of vasculogenesis, angiogenesis, or tubulogenesis.

4. The method of claim 1, wherein the one or more of biological agent gradient, the pressure gradient, and/or the oxygen tension gradient further direct development, differentiation, and/or functioning of the embryoid body or organoid.

5. The method of claim 1, wherein the first vascular network and the second vascular network are independently addressable.

6. The method of claim 1, wherein the first vascular network and the second vascular network are not in contact with each other prior to the vascularizing step (c).

7. The method of claim 1, wherein the first vascular network comprises an arterial plexus and the second vascular network comprises a venous plexus.

8. The method of claim 1, wherein the single vascular network comprises at least one of an interpenetrating vascular network or a branched interpenetrating vascular network.

9. The method of claim 1, wherein the single vascular network comprises interconnected arterial and venous channels.

10. The method of claim 1, wherein the embryoid body or organoid is created by culturing at least one of: pluripotent stem cells, multipotent stem cells, progenitor cells, terminally differentiated cells, endothelial cells, endothelial progenitor cells, immortalized cell lines, or primary cells.

11. The method of claim 1, wherein, prior to, during and/or after the embedding, the embryoid body or organoid is further differentiated into a tissue containing at least one of pluripotent stem cells, multipotent stem cells, progenitor cells, terminally differentiated cells, endothelial cells, endothelial progenitor cells, immortalized cell lines, or primary cells.

12. The method of claim 1, wherein the embryoid body or organoid is selected from the group consisting of: cerebral organoid, thyroid organoid, intestinal or gut organoid, hepatic organoid, pancreatic organoid, gastric organoid, kidney organoid, retinal organoid, cardiac organoid, bone organoid, and epithelial organoid.

13. The method of claim 1, wherein the embryoid body or organoid is exposed to the biological agent gradient by at least one of:
   diffusion of one or more biological agents within the tissue construct;
   localized deposition of materials loaded with one or more biological agents within the tissue construct;
   localized de-novo production of growth factors by localized protein translation; or
   perfusion of one or both of the first and second vascular networks with one or more biological agents.

14. The method of claim 1, wherein only one of the first and second vascular networks is exposed to a biological agent gradient prior to the vascularizing step (c).

15. The method of claim 1, wherein both the first and second vascular networks are exposed to a biological agent gradient, and wherein the biological agent concentration in the first vascular network is different than the biological agent concentration in the second vascular network.

16. The method of claim 1, wherein both the first and second vascular networks are exposed to a biological agent gradient, and wherein the biological agent concentration in the first vascular network is the same as the biological agent concentration in the second vascular network.

17. The method of claim 1, wherein the biological agent in the biological agent gradient comprises is one or more of: vascular endothelial growth factor (VEGF), basic fibroblast growth factor (bFGF), sphingosine-1-phosphate (S1P), phorbol myristate acetate (PMA), hepatocyte growth factor (HGF), monocyte chemotactic protein-1 (MCP-1), the angiopoietin ANG-1, the angiopoietin ANG-2, transforming growth factor beta (TGF-β), epidermal growth factor (EGF), human growth factor, matrix metalloproteinases (MMP's), or histamine.

18. The method of claim 1, wherein an oxygen partial pressure gradient is introduced to one or both of the first and second vascular networks during the exposing step.

19. The method of claim 18, wherein the oxygen partial pressure gradient is formed by introducing deoxygenated media into one of the first and second vascular networks, and by introducing oxygenated media into the other of the first and second vascular networks.

20. The method of claim 13, wherein one or both of the first and second vascular networks are subjected to a transmural pressure during the perfusion.

21. The method of claim 1, wherein, prior to embedding the embryoid body or organoid in the tissue construct, the embryoid body or organoid is encapsulated in an extracellular matrix material comprising a gel.

22. The method of claim 1, wherein the embryoid body or organoid comprises a first population of embryoid body or organoid cells and a second population of embryoid body or organoid cells.

23. The method of claim 22, wherein the embryoid body or organoid comprises at least two of: pluripotent stem cells, multipotent stem cells, progenitor cells, terminally differentiated cells, endothelial cells, endothelial progenitor cells, immortalized cell lines, neural cells, primary cells, or a combination thereof.

24. The method of claim 1, wherein the embryoid body or organoid is created by:
   culturing a wild-type population of cells and a genetically-engineered inducible population of cells in a medium;
   inducing direct differentiation and/or transdifferentiation of the genetically-engineered inducible population of cells into a first population of the embryoid body or organoid cells;
   inducing differentiation of the wild-type population of cells into a second population of the embryoid body or organoid cells; and
   thereby forming the embryoid body or organoid comprising at least the first population of the embryoid body or organoid cells and the second population of embryoid body or organoid cells.

25. The method of claim 24, wherein the embryoid body or organoid is selected from the group consisting of: cerebral organoid, thyroid organoid, intestinal or gut organoid, hepatic organoid, pancreatic organoid, gastric organoid, kidney organoid, retinal organoid, cardiac organoid, bone organoid, and epithelial organoid.

26. The method of claim 24, wherein the genetically-engineered inducible population of cells is created by introducing a DNA delivery element comprising at least one of constitutive promoter, small molecule inducible promoter, cell-autonomous promoter, cell non-autonomous promoter, selection marker, or a combination thereof.

27. The method of claim 24, wherein the first population of the embryoid body or organoid cells comprises pluripotent stem cells, multipotent stem cells, progenitor cells, terminally differentiated cells, endothelial cells, endothelial progenitor cells, immortalized cell lines, or primary cells.

28. The method of claim 24, wherein the step of inducing direct differentiation and/or transdifferentiation of the genetically-engineered inducible population of cells comprises introducing at least one cue selected from the group consisting of transcription factors, drugs, small molecules, growth factors, morphogens, hormones, DNA, shRNA, siRNA, nanoparticles, mRNA, modified mRNA, heat, light, and mechanical force.

29. The method of claim 24, wherein the induced direct differentiation and or transdifferentiation is accompanied by a secondary gene induction.

30. The method of claim 24, wherein the step of culturing is in a differentiation medium, and wherein the differentiation medium comprises doxycycline (DOX).

31. The method of claim 24, wherein the wild-type population of cells comprises induced pluripotent stem cells (iPSCs) or iPSCs-derived patient-specific cell lines.

32. The method of claim 1, wherein one or both of the first and second vascular networks comprise microfluidic channels.

33. The method of claim 1, wherein a plurality of the embryoid bodies or organoids are embedded in the tissue construct.

34. The method of claim 33, wherein the embryoid bodies or organoids comprise different phenotypes.

35. The method of claim 33, wherein the embryoid bodies or organoids comprise the same phenotype.

36. The method of claim 1, wherein the tissue construct comprises an array of the tissue constructs, wherein the embedding, exposing and vascularizing is carried out in each tissue construct.

37. An implantable, functional human tissue formed by the in vitro method of claim 1, wherein the embryoid body or organoid is prepared for an immunofluorescence protocol.

* * * * *

UNITED STATES PATENT AND TRADEMARK OFFICE
CERTIFICATE OF CORRECTION

Page 1 of 1

PATENT NO. : 11,214,768 B2
APPLICATION NO. : 15/554963
DATED : January 4, 2022
INVENTOR(S) : Lewis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 211 days.

Signed and Sealed this
Tenth Day of January, 2023

Katherine Kelly Vidal
*Director of the United States Patent and Trademark Office*